United States Patent [19]

Machida et al.

[11] Patent Number: 4,546,176
[45] Date of Patent: Oct. 8, 1985

[54] 7-CARBOXYMETHOXY-PHENYLACETAMIDO-3-CEPHEM DERIVATIVES AND ANTIBACTERIAL PREPARATIONS CONTAINING THE SAME

[75] Inventors: Yoshimasa Machida; Shigeto Negi; Seiichiro Nomoto; Takashi Kamiya; Kyosuke Kitoh; Isao Saito, all of Ibaraki, Japan

[73] Assignee: Eisai Co., Ltd., Tokyo, Japan

[21] Appl. No.: 544,406

[22] Filed: Oct. 20, 1983

[30] Foreign Application Priority Data

Dec. 14, 1982 [JP] Japan .................................. 57-217726
Mar. 7, 1983 [JP] Japan .................................. 58-36017

[51] Int. Cl.⁴ .................. C07D 501/00; C07D 501/14; A61K 31/54
[52] U.S. Cl. ...................................... 544/21; 544/25; 544/27; 544/28; 514/338; 514/434
[58] Field of Search ............................ 544/21, 25, 28; 424/246; 260/239.1

[56] References Cited

U.S. PATENT DOCUMENTS 4,015,000  3/1977  Kocsis et al. ........................ 544/24
4,338,439  7/1982  Herron et al. ....................... 544/28
4,344,944  8/1982  Machida et al. ..................... 544/21

Primary Examiner—Donald G. Daus
Assistant Examiner—Cecilia Shen
Attorney, Agent, or Firm—Wenderoth, Lind & Ponack

[57] ABSTRACT

7-Carboxymethoxyphenylacetamido-3-cephem derivatives represented by the formula

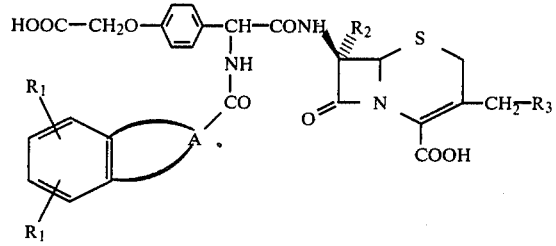

wherein $R_1$ means hydroxy, $C_1$–$C_4$ alkanoyloxy or $C_1$–$C_4$ alkoxycarbonyloxy, $R_2$ is hydrogen or methoxy, $R_3$ denotes $C_1$–$C_4$ alkanoyloxy, substituted or unsubstituted nitrogen-containing heterocyclic-thio or substituted or unsubstituted pyridinium with a proviso that, when $R_3$ denotes the substituted or unsubstituted pyridinium, $R_3$ forms an intramolecular salt with the carboxy at the 4-position of the cephem nucleus, and A is a group of the following formula:

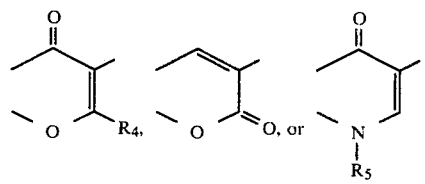

in which $R_4$ and $R_5$ are individually hydrogen or $C_1$–$C_4$ alkyl, and their pharmaceutically acceptable salts, exhibit excellent anti-bacterial activities against Gram-negative bacteria, particularly, Pseud. aeruginosa, Kleb. pneumoniae, Ser. marcescens and the like.

14 Claims, No Drawings

7-CARBOXYMETHOXYPHENYLACETAMIDO-3-CEPHEM DERIVATIVES AND ANTIBACTERIAL PREPARATIONS CONTAINING THE SAME

BACKGROUND OF THE INVENTION (a) Field of the Invention

This invention relates to novel 7-carboxymethoxyphenylacetamido-3-cephem derivatives represented by the formula:

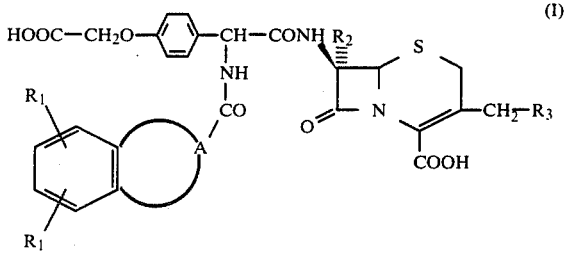

wherein $R_1$ means hydroxy, $C_1$–$C_4$ alkanoyloxy or $C_1$–$C_4$ alkoxycarbonyloxy, $R_2$ is hydrogen or methoxy, $R_3$ denotes $C_1$–$C_4$ alkanoyloxy, substituted or unsubstituted nitrogen-containing hetrocyclic-thio or substituted or unsubstituted pyridinium with a proviso that, when $R_3$ denotes the substituted or unsubstituted pyridinium, $R_3$ forms an intramolecular salt with the carboxy at the 4-position of the cephem nucleus, and A is a group of the following formula:

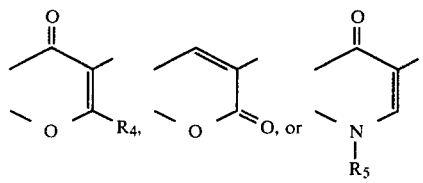

in which $R_4$ and $R_5$ are individually hydrogen or $C_1$–$C_4$ alkyl, or a pharmaceutically acceptable salt thereof, processes for the preparation thereof, and antibacterial preparations containing the same.

In the above formula (I), acetoxy, propionyloxy, butyryloxy, isobutyryloxy, etc. may be mentioned as exemplary $C_1$–$C_4$ alkanoyloxy groups represented by $R_1$ and $R_3$ while methyl, ethyl, propyl, isopropyl, butyl, isobutyl, sec-butyl, tert-butyl and the like many be mentioned as illustrative $C_1$–$C_4$ alkyl groups represented by $R_4$ and $R_5$. As exemplary $C_1$–$C_4$ alkoxycarbonyloxy groups represented by $R_1$, may be mentioned ethoxycarbonyloxy and methoxycarbonyloxy groups.

The term "substituted or unsubstituted nitrogen-containing heterocyclic-thio" represented by $R_3$ in the formula (I) means substituted or unsubstituted heterocyclic-thio containing one or more nitrogen atoms as hetero atom or atoms of the heterocyclic nucleus. The group may be a mono- or polycyclic-thio group, and may optionally contain one or more sulfur and/or oxygen atoms in the heterocyclic nucleus, in addition to the nitrogen atom or atoms. Illustrative nitrogen-containing heterocyclic nuclei of the heterocyclic-thio may include such as pyrrolyl, pyridyl and the N-oxide thereof, imidazolyl, parazolyl, pyrimidinyl, pyridazinyl, tetrazolo[4,5-b]pyridazinyl, 1H-1,2,4-triazolyl, 4H-1,2,4-triazolyl, 1H-1,2,3-triazolyl, 2H-1,2,3-triazolyl, 1,2,5,6-tetrahydro-5,6-dioxo-as-triazinyl, 1H-tetrazolyl, 2H-tetrazolyl, thiazolyl, 1,2,3-thiadiazolyl, 1,2,4-thiadiazolyl, 1,3,4-thiadiazolyl, oxazolyl, 1,3,4-oxadiazolyl, 1,2,5-oxadiazolyl, morpholino, benzothiazolyl, benzoxazolyl, etc. These heterocyclic nuclei and the pyridinium group may each contain one or more substituents selected from $C_1$–$C_4$ alkyl groups such as methyl ethyl, propyl, isopropyl, butyl, isobutyl, sec-butyl, tert-butyl and the like; carboxyalkyl groups such as carboxymethyl, carboxyethyl and the like; sulfoalkyl groups such as sulfomethyl, sulfoethyl, etc.; amino groups; N,N-dialkylaminoalkyl groups such as N,N-dimethylaminomethyl, N,N-diethylaminoethyl, N,N-dimethylaminoethyl; carbamoyl groups; N-alkylcarbamoyl groups such as N-ethylcarbamoyl, N-methylcarbamoyl, etc.; alkoxycarbonyl groups such as methoxycarbonyl, ethoxycarbonyl and the like; carboxyl group; sulfo group; cyano group; N-hydroxycarbamoyl group; N-hydroxycarbamoylalkyl groups such as N-hydroxycarbamoyl methyl, N-hydroxycarbamoylethyl and the like; carbamoylalkyl groups such as carbamoylethyl, carbamoylmethyl, etc.; N,N-dialkylcarbamoyl groups such as N,N-dimethylcarbamoyl, N,N-diethylcarbamoyl, etc.; N-hydroxy-N-alkylcarbamoyl groups such as N-hydroxy-N-methylcarbamoyl, N-hydroxy-N-ethylcarbamoyl and the like; hydroxyl group; hydroxyalkyl groups such as hydroxymethyl, hydroxyethyl and the like; and alkoxycarbonylalkyl groups such as methoxycarbonylmethyl, methoxycarbonylethyl and the like.

As specific groups represented by $R_3$, may for example be mentioned acetoxy, (1-methyl-5-tetrazolyl)thio, (1-carboxymethyl-5-tetrazolyl)thio, [5-methyl-2-(1,3,4-thiadiazolyl)]thio, [1-(2-N,N-dimethylaminoethyl)-5-tetrazolyl]thio, [5-carboxymethyl-2-(1,3,4-thiadiazolyl]thio, [5-carboxymethyl-2-(1,3,4-oxadiazolyl)]thio, pyridinium, 4-carbamoylpyridinium, 4-(2-sulfoethyl)pyridinium, 3-carboxymethylpyridinium, 3-carboxypyridinium, 4-carboxypyridinium, 4-cyanopyridinium, 4-sulfopyridinium, 3-carbamoylpyridinium, 4-N-hydroxycarbamoylpyridinium, 4-N-hydroxy-N-methylcarbamoylpyridinium and 4-(2-N,N-dimethylaminoethyl)-pyridinium.

Furthermore, the following groups may for example be mentioned as specific groups represented by A in the formula (I):

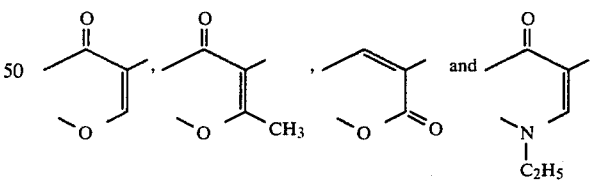

As the pharmaceutically acceptable salts of the compounds of the general formula (I), may be mentioned those commonly employed for cephalosporin derivatives. They may for example be the sodium, potassium, calcium, ammonium, triethylamine, dicyclohexylamine and procaine salts.

(b) Description of the Prior Art

7-Phenylacetamido-3-cephem derivatives containing benzopyran or quinoline have been proposed in recent years, as disclosed in Japanese Patent Application Laid-open Nos. 136292/1980, 5487/1981, 73087/1981, 122384/1981, 18689/1982, 165389/1982, 165390/1981, the corresponding U.S. Pat. Nos. 4285939, 4285941, 4285940, 4344944, 4344944, 4468394, 4468394, respectively, etc. These compounds have strong antibacterial activities against Gram-negative bacteria, notably, *Pseud. aeruginosa, Kleb. pneumoniae, Ser. marcescens* and the like and are very effective against a variety of infectious diseases. However, each of these compounds is primarily excreted into bile when administered in animals and its excretion rate into urine does not reach even 1% when administered in mice by the subcutaneous route. These compounds are still effective, even at such a low excretion rate into urine as mentioned above, against infections of the urinary tract owing to their very strong antibacterial activities. However, there is a standing demand for the development of 7-phenylacetamido-3-cephem derivatives having higher excretion rates into urine.

SUMMARY OF THE INVENTION

The object of this invention is to provide novel compounds exhibiting excellent therapeutic effects against infectious diseases. The object has been achieved by introducing a carboxymethoxy group to the para-position of the phenyl group of each of the above-described prior art 7-phenylacetamido-3-cephem derivatives, which para-position is either unsubstituted or substituted by a hydroxyl group. Owing to the introduction of the carboxymethoxy group, each of the compounds according to this invention shows a great improvement of the excretion rate into urine. Furthermore, these compounds were found to retain antibacterial activities as strong as the above-described prior art compounds and to exhibit excellent antibacterial activities against gram-negative bacteria, notably, *Pseud. aeruginosa, Kleb. pneumoniae, Ser. marcescens* and the like. Although the above-described known compounds generally have low solubility in water and the solubility of the most water-soluble one of such known compounds is still as low as somewhat over 10%, the water-solubility of each of the compounds according to this invention has also been improved. This is advantageous particularly for the production of preparation for injection.

DETAILED DESCRIPTION OF THE INVENTION

The compounds according to this invention may be prepared in accordance with the following processes:

Preparation Process (1)

The compound of the formula (I) or the pharmaceutically acceptable salt thereof is obtained by reacting a compound represented by the formula:

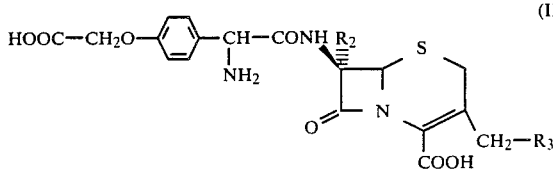
(II)

wherein $R_2$ and $R_3$ have the same meanings as defined above with a proviso that, when $R_3$ denotes substituted or unsubstituted pyridinium, $R_3$ forms an intramolecular salt with the carboxy at the 4-position of the cephem nucleus or salt thereof with a compound represented by the formula:

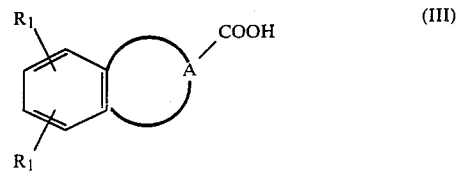
(III)

wherein $R_1$ and A have the same meanings as defined above or a reactive derivative thereof.

It is preferable to carry out the above reaction in the presence of a condensing agent such as, for example, N,N'-dicyclohexylcarbodiimide, N,N'-diethylcarbodiimide, N-cyclohexyl-N'-(2-morpholinoethyl)carbodiimide, ethyl phosphite, phosphorus oxychloride, oxalyl chloride or the like where the compound of the formula (III) is used as it is. When using a reactive derivative of the compound of the formula (III) which derivative has been obtained by modifying the carboxyl group, the reactive derivative may be an acid halide such as the acid chloride or acid bromide; a symmetric acid anhydride; a mixed-acid anhydride with a chlorocarbonic acid ester, trimethylacetic acid, diphenylacetic acid or the like; and active ester with 2-mercaptopyridine, cyanomethanol, p-nitrophenol, 2,4-dinitrophenol, pentachlorophenol, N-hydroxysuccinimide, 1-hydroxybenzotriazol or the like; or an active acid amide such as N-acylsaccharin, N-acylphthalimide or the like.

The above reaction may be carried out in an inert solvent, in the presence or absence of a basic reagent or a silylating agent, and at a temperature of $-50°$ C. to $+50°$ C., preferably $-20°$ C. to $+30°$ C.

As the inert solvent, may for example be mentioned acetone, tetrahydrofuran, dimethylacetamide, dimethylformamide, dioxane, dichloromethane, chloroform, benzene, toluene, ethyl acetate, acetonitrile or a mixed solvent thereof.

Illustrative basic reagents may include alkali metal hydroxides such as sodium hydroxide and potassium hydroxide; alkali metal carbonate such as sodium carbonate and potassium carbonate; alkali metal hydrogencarbonates such as sodium hydrogencarbonate and potassium hydrogencarbonate; and amines such as triethylamine, pyridine, dimethylaniline and N-methylmorpholine.

Exemplary silylating agents may embrace N,O-bis(-trimethylsilyl)acetamide, hexamethyldisilazane, N-trimethylsilylacetamide.

Preparation Process (2)

A compound represented by the formula:

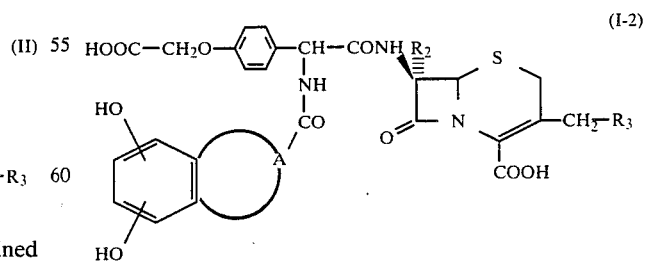
(I-2)

wherein A, $R_2$ and $R_3$ have the same meanings as defined above with a proviso that, when $R_3$ denotes substituted or unsubstituted pyridinium, $R_3$ forms an intramolecular salt with the carboxy at the 4-position of the cephem nucleus or a pharmaceutically acceptable salt thereof is obtained by hydrolyzing a compound represented by the formula:

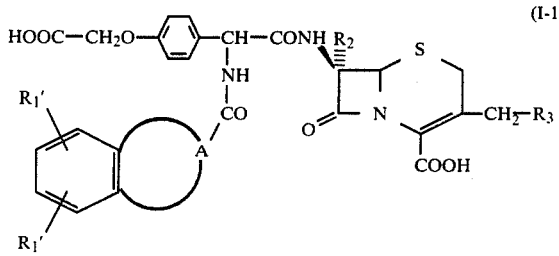 (I-1)

wherein A, $R_2$ and $R_3$ have the same meanings as defined above and $R_1'$ means $C_1$–$C_4$ alkanoyloxy or $C_1$–$C_4$ alkanoylcarbonyloxy or a salt thereof in the presence of a base.

The above hydrolysis reaction may be carried out in accordance with a method commonly employed in hydrolyses of esters. As the base may for example be mentioned an alkali metal hydroxide such as sodium hydroxide or potassium hydroxide, an alkali metal hydrogencarbonate such as sodium hydrogencarbonate or potassium hydrogencarbonate, or an alkali metal carbonate such as sodium carbonate or potassium carbonate.

Preparation Process (3)

A compound represented by the formula:

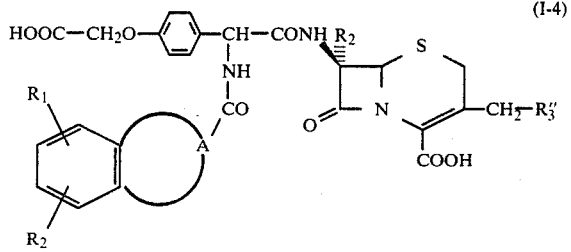 (I-4)

wherein $R_1$, $R_2$ and A have the same meanings as defined above and $R_3''$ is substituted or unsubstituted nitrogen-containing heterocyclic-thio or substituted or unsubstituted pyridinium with a proviso that, when $R_3''$ denotes the substituted or unsubstituted pyridinium, $R_3''$ forms an intramolecular salt with the carboxy at the 4-position of the cephem nucleus or a pharmaceutically acceptable salt thereof is obtained by reacting a compound represented by the formula:

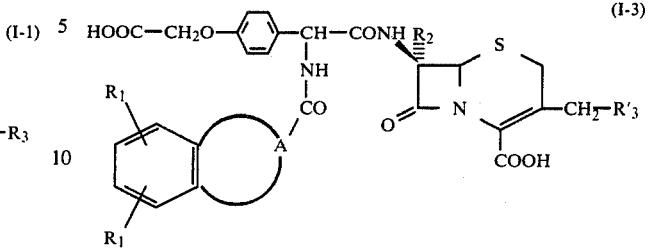 (I-3)

where $R_1$, $R_2$ and A have the same meanings as defined above and $R_3'$ denotes $C_1$–$C_4$ alkanoyloxy or a salt thereof with a substituted or unsubstituted nitrogen-containing heterocyclic-thio or a substituted or unsubstituted pyridine.

In the preparation of the compound of the formula (I-4) wherein $R_3''$ denotes substituted or unsubstituted nitrogen-containing heterocyclic-thio, the above reaction may be carried out in a manner known per se in the art, as disclosed in Japanese Patent Application Laid-open Nos. 5487/1981, 122384/1981, 130689/1978, the corresponding U.S. Pat. Nos. 4285941, 4344944, and 4,144,391 respectively, etc. It may for example be conducted in a solvent such as water or a buffer, in the presence of sodium hydrogencarbonate, sodium hydroxide or the like, and at a temperature range of 50° C.–70° C.

In the preparation of the compound of the formula (I-4) wherein $R_3''$ denotes substituted or unsubstituted pyridinium, it is desirable to carry out the reaction in the presence of an alkali metal salt. As exemplary alkali metal salts, may be mentioned sodium iodide, potassium iodide, sodium bromide, potassium bromide, potassium thiocyanate, sodium thiocyanate, potassium nitrate, sodium nitrate and the like. As the solvent, may be mentioned an aquous solvent such as water or buffer, a hydrophilic solvent such as formamide, tetrahydrofuran, methanol, dimethylformamide, acetonitrile or dioxane, or a mixture thereof. The reaction temperature may suitably range from 30° C. to 90° C.

Preparation Process (4)

A compound represented by the formula:

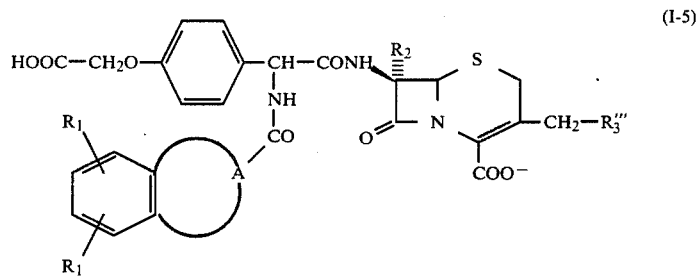 (I-5)

wherein $R_1$, $R_2$ and A have the same meanings as defined above and $R_3'''$ is substituted or unsubstituted pyridinium or a pharmaceutically acceptable salt thereof is obtained by reacting a compound represented by the formula:

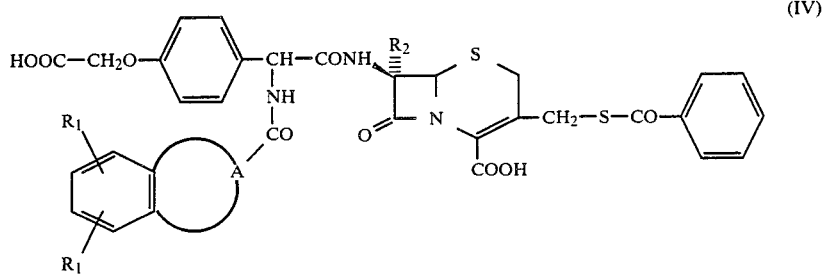

wherein $R_1$, $R_2$ and A have the same meanings as defined above or a salt thereof with a substituted or unsubstituted pyridine.

The above reaction may be carried out in accordance with the method disclosed for example in U.S. Pat. No. 4015000. For example, the reaction may be conducted for example in an inert solvent such as dioxane, tetrahydrofuran or dimethoxyethane, in the presence of mercuric perchlorate or the like, and at a temperature range of 30° C.–90° C.

The pharmaceutically acceptable salt of the compound of the formula (I) may be obtained from the isolated compound of the formula (I) in accordance with the usual salt-forming reaction. In each of the above preparation processes (1)-(4), each resultant compound may be subjected, after completion of the reaction, directly to the subsequent salt-forming reaction without isolation thereof, followed by isolation of the compound of the formula (I) as a pharmaceutically acceptable salt thereof.

The compound of the general formula (II), which is a starting compound in the present invention, may be obtained in accordance with the following reaction scheme:

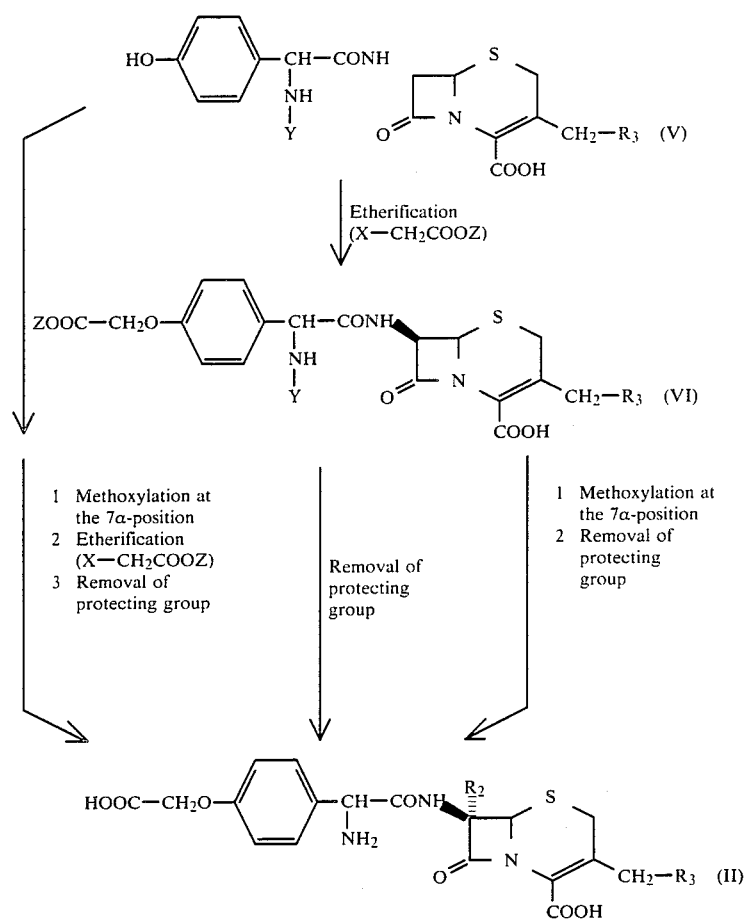

wherein $R_2$ and $R_3$ have the same meanings as defined above, X means a halogen atom, Y stands for a protecting group for amino group, and Z is a protecting group for carboxyl group with a proviso that, when $R_3$ denotes substituted or unsubstituted pyridinium, $R_3$ forms an intramolecular salt with the carboxy at the 4-position of the cephem nucleus.

The compound of the formula (II) may also be obtained in accordance with the following reaction scheme:

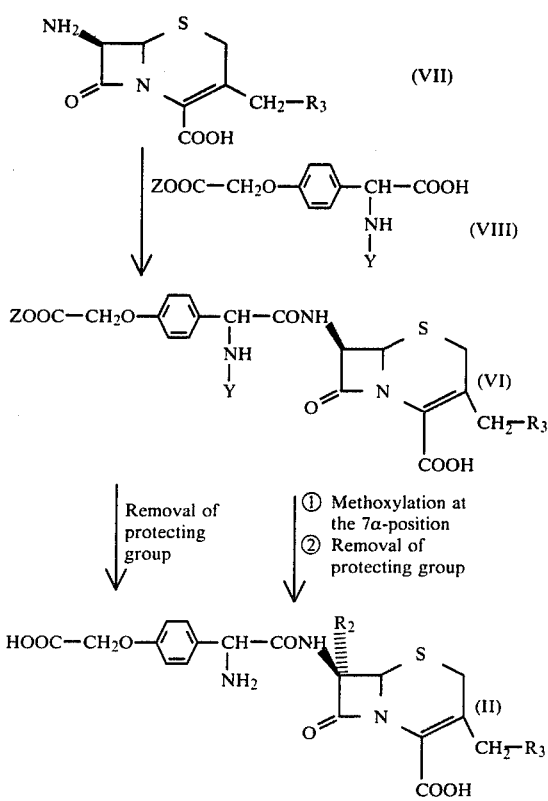

ps wherein $R_2$, $R_3$, X, Y and Z have the same meanings as defined above with a proviso that, when $R_3$ denotes substituted or unsubstituted pyridinium, $R_3$ forms an intramolecular salt with the carboxy at the 4-position of the cephem nucleus.

The compound of the formula (II) wherein $R_3$ is substituted or unsubstituted nitrogen-containing heterocyclic-thio or substituted or unsubstituted pyridinium also may be prepared as follows;

1. The compound of the formula (VI) wherein $R_3$ is $C_1$–$C_4$ alkanoyloxy is obtained as shown in the schemes;
2. The $C_1$–$C_4$ alkanoyloxy is converted to substituted or unsubstituted nitrogen-containing heterocyclic-thio or substituted or unsubstituted pyridinium by a similar method as employed in the preparation process (3); and
3. The compound of the formula (II) is obtained as shown in the schemes.

As specific compounds according to this invention, may for example be mentioned the following compounds and pharmaceutically acceptable salts thereof, especially the sodium salts thereof:

7β-[D-2-(4-Carboxymethoxyphenyl)-2-(6,7-dihydroxy-2-methyl-4-oxo-4H-1-benzopyran-3-carboxamido)-acetamido]-7α-methoxy-3-(1-carboxymethyl-5-tetrazolyl)thiomethyl-3-cephem-4-carboxylic acid;

7β-[D-2-(4-Carboxymethoxyphenyl)-2-(7,8-dihydroxy-2-methyl-4-oxo-4H-1-benzopyran-3-carboxamido)-acetamido]-7α-methoxy-3-(1-carboxymethyl-5-tetrazolyl)thiomethyl-3-cephem-4-carboxylic acid;

7β-[D-2-(4-Carboxymethoxyphenyl)-2-(6,7-dihydroxy-2-methyl-4-oxo-4H-1-benzopyran-3-carboxamido)acetamido]-3-(1-carboxymethyl-5-tetrazolyl)thiomethyl-3-cephem-4-carboxylic acid;

7β-[D-2-(4-Carboxymethoxyphenyl)-2-(7,8-dihydroxy-2-methyl-4-oxo-4H-1-benzopyran-3-carboxamido)-acetamido]-3-(1-carboxymethyl-5-tetrazolyl)thiomethyl-3-cephem-4-carboxylic acid;

7β-[D-2-(4-Carboxymethoxyphenyl)-2-(6,7-dihydroxy-4-oxo-4H-1-benzopyran-3-carboxamido)acetamido]-7α-methoxy-3-(1-carboxymethyl-5-tetrazolyl)thiomethyl-3-cephem-4-carboxylic acid;

7β-[D-2-(4-Carboxymethoxyphenyl)-2-(7,8-dihydroxy-4-oxo-4H-1-benzopyran-3-carboxamido)acetamido]-7α-methoxy-3-(1-carboxymethyl-5-tetrazolyl)thiomethyl-3-cephem-4-carboxylic acid;

7β-[D-2-(4-Carboxymethoxyphenyl)-2-(6,7-dihydroxy-4-oxo-4H-1-benzopyran-3-carboxamido)acetamido]-3-(1-carboxymethyl-5-tetrazolyl)thiomethyl-3-cephem-4-carboxylic acid;

7β-[D-2-(4-Carboxymethoxyphenyl)-2-(7,8-dihydroxy-4-oxo-4H-1-benzopyran-3-carboxyamido)acetamido]-3-(1-carboxymethyl-5-tetrazolyl)thiomehtyl-3-cephem-4-carboxylic acid;

7β-[D-2-(4-Carboxymethoxyphenyl)-2-(6,7-dihydroxy-2-propyl-4-oxo-4H-1-benzopyran-3-carboxamido)acetamido]-7α-methoxy-3-(1-carboxymethyl-5-tetrazolyl)thiomethyl-3-cephem-4-carboxylic acid;

7β-[D-2-(4-Carboxymethoxyphenyl)-2-(6,7-dihydroxy-2-ethyl-4-oxo-4H-1-benzopyran-3-carboxamido)acetamido]-7α-methoxy-3-(1-carboxymethyl-5-tetrazolyl)thiomethyl-3-cephem-4-carboxylic acid;

7β-[D-2-(4-Carboxymethoxyphenyl)-2-(6,7-dihydroxy-2-oxo-2H-1-benzopyran-3-carboxamido)acetamido]-7α-methoxy-3-(1-carboxymethyl-5-tetrazolyl)thiomethyl-3-cephem-4-carboxylic acid;

7β-[D-2-(4-Carboxymethoxyphenyl)-2-(7,8-dihydroxy-2-oxo-2H-1-benzopyran-3-carboxamido)acetamido]-7α-methoxy-3-(1-carboxymethyl-5-tetrazolyl)thiomethyl-3-cephem-4-carboxylic acid;

7β-[D-2-(4-Carboxymethoxyphenyl)-2-(6,7-dihydroxy-2-oxo-2H-1-benzopyran-3-carboxamido)acetamido]-3-(1-carboxymethyl-5-tetrazolyl)thiomethyl-3-cephem-4-carboxylic acid;

7β-[D-2-(4-Carboxymethoxyphenyl)-2-(6,7-dihydroxy-1-ethyl-1,4-dihydro-4-oxoquinolin-3-carboxamido)acetamido]-7α-methoxy-3-(1-carboxymethyl-5-tetrazolyl)thiomethyl-3-cephem-4-carboxylic acid;

7β-[D-2-(4-Carboxymethoxyphenyl)-2-(6,7-dihydroxy-1-ethyl-1,4-dihydro-4-oxoquinolin-3-carboxamido)-acetamido]-3-(1-carboxymethyl-5-tetrazolyl)-thiomethyl-3-cephem-4-carboxylic acid;

7β-[D-2-(4-Carboxymethoxyphenyl)-2-(7,8-dihydroxy-1-ethyl-1,4-dihydro-4-oxoquinolin-3-carboxamido)-acetamido]-7α-methoxy-3-(1-carboxymethyl-5-tetrazolyl)thiomethyl-3-cephem-4-carboxylic acid;

7β-[D-2-(4-Carboxymethoxyphenyl)-2-(6,7-dihydroxy-2-methyl-4-oxo-4H-1-benzopyran-3-carboxamido)-acetamido]-7α-methoxy-3-acetoxymethyl-3-cephem-4-carboxylic acid;

7β-[D-2-(Carboxymethoxyphenyl)-2-(7,8-dihydroxy-2-methyl-4-oxo-4H-1-benzopyran-3-carboxamido)-acetamido]-7α-methoxy-3-acetoxymethyl-3-cephem-4-carboxylic acid;

7β-[D-2-(4-Carboxymethoxyphenyl)-2-(6,7-dihydroxy-2-methyl-4-oxo-4H-1-benzopyran-3-carboxamido)-acetamido]-3-acetoxymethyl-3-cephem-4-carboxylic acid;

7β-[D-2-(4-Carboxymethoxyphenyl)-2-(7,8-dihydroxy-2-methyl-4-oxo-4H-1-benzopyran-3-carboxamido)-acetamido]-3-acetoxymethyl-3-cephem-4-carboxylic acid;

7β-[D-2-(4-Carboxymethoxyphenyl)-2-(6,7-dihydroxy-4-oxo-4H-1-benzopyran-3-carboxamido)acetamido]-7α-methoxy-3-acetoxymethyl-3-cephem-4-carboxylic acid;

7β-[D-2-(4-Carboxymethoxyphenyl)-2-(7,8-dihydroxy-4-oxo-4H-1-benzopyran-3-carboxamido)acetamido]-7α-methoxy-3-acetoxymethyl-3-cephem-4-carboxylic acid;

7β-[D-2-(4-Carboxymethoxyphenyl)-2-(6,7-dihydroxy-4-oxo-4H-1-benzopyran-3-carboxamido)acetamido]-3-acetoxymethyl-3-cephem-4-carboxylic acid;

7β-[D-2-(4-Carboxymethoxyphenyl)-2-(7,8-dihydroxy-4-oxo-4H-1-benzopyran-3-carboxamido)acetamido]-3-acetoxymethyl-3-cephem-4-carboxylic acid;

7β-[D-2-(4-Carboxymethoxyphenyl)-2-(6,7-dihydroxy-2-oxo-2H-1-benzopyran-3-carboxamido)acetamido]-7α-methoxy-3-acetoxymethyl-3-cephem-4-carboxylic acid;

7β-[D-2-(4-Carboxymethoxyphenyl)-2-(6,7-dihydroxy-2-oxo-2H-1-benzopyran-3-carboxamido)acetamido]-3-acetoxymethyl-3-cephem-4-carboxylic acid;

7β-[D-2-(4-Carboxymethoxyphenyl)-2-(6,7-dihydroxy-1-ethyl-1,4-dihydro-4-oxoquinolin-3-carboxamido)-acetamido]-7α-methoxy-3-acetoxymethyl-3-cephem-4-carboxylic acid;

7β-[D-2-(4-Carboxymethoxyphenyl)-2-(6,7-dihydroxy-1-ethyl-1,4-dihydro-4-oxoquinolin-3-carboxamido)-acetamido]-3-acetoxymethyl-3-cephem-4-carboxylic acid;

7β-[D-2-(4-Carboxymethoxyphenyl)-2-(6,7-dihydroxy-2-methyl-4-oxo-4H-1-benzopyran-3-carboxamido)-acetamido]-7α-methoxy-3-(1-methyl-5-tetrazolyl)thiomethyl-3-cephem-4-carboxylic acid;

7β-[D-2-(4-Carboxymethoxyphenyl)-2-(7,8-dihydroxy-2-methyl-4-oxo-4H-1-benzopyran-3-carboxamido)-acetamido]-7α-methoxy-3-(1-methyl-5-tetrazolyl)-thiomethyl-3-cephem-4-carboxylic acid;

7β-[D-2-(4-Carboxymethoxyphenyl)-2-(6,7-dihydroxy-2-methyl-4-oxo-4H-1-benzopyran-3-carboxamido)-acetamido]-3-(1-methyl-5-tetrazolyl)thiomethyl-3-cephem-4-carboxylic acid;

7β-[D-2-(4-Carboxymethoxyphenyl)-2-(6,7-dihydroxy-4-oxo-4H-1-benzopyran-3-carboxamido)acetamido]-7α-methoxy-3-(1-methyl-5-tetrazolyl)thiomethyl-3-cephem-4-carboxylic acid;

7β-[D-2-(4-Carboxymethoxyphenyl)-2-(6,7-dihydroxy-4-oxo-4H-1-benzopyran-3-carboxamido)acetamido]-3-(1-methyl-5-tetrazolyl)thiomethyl-3-cephem-4-carboxylic acid;

7β-[D-2-(4-Carboxymethoxyphenyl)-2-(7,8-dihydroxy-4-oxo-4H-1-benzopyran-3-carboxamido)acetamido]-3-(1-methyl-5-tetrazolyl)thiomethyl-3-cephem-4-carboxylic acid;

7β-[D-2-(4-Carboxymethoxyphenyl)-2-(6,7-dihydroxy-2-oxo-2H-1-benzopyran-3-carboxamido)acetamido]-3-(1-methyl-5-tetrazolyl)thiomethyl-3-cephem-4-carboxylic acid;

7β-[D-2-(4-Carboxymethoxyphenyl)-2-(6,7-dihydroxy-1-ethyl-1,4-dihydro-4-oxoquinolin-3-carboxamido)-acetamido]-7α-methoxy-3-(1methyl-5-tetrazolyl)-thiomethyl-3-cephem-4-carboxylic acid;

7β-[D-2-(4-Carboxymethoxyphenyl)-2-(6,7-dihydroxy-1-ethyl-1,4-dihydro-4-oxoquinolin-3-carboxamido)-acetamido]-3-(1-methyl-5-tetrazolyl)thiomethyl-3-cephem-4-carboxylic acid;

7β-[D-2-(4-Carboxymethoxyphenyl)-2-(6,7-dihydroxy-2-methyl-4-oxo-4H-1-benzopyran-3-carboxamido)-acetamido]-7α-methoxy-3-[1-(2-N,N-dimethylaminoethyl)-5-tetrazolyl]thiomethyl-3-cephem-4-carboxylic acid;

7β-[D-2-(4-Carboxymethoxyphenyl)-2-(6,7-dihydroxy-2-methyl-4-oxo-4H-1-benzopyran-3-carboxamido)-acetamido]-3-[1-(2-N,N-dimethylaminoethyl)-5-tetrazolyl]-thiomethyl-3-cephem-4-carboxylic acid;

7β-[D-2-(4-Carboxymethoxyphenyl)-2-(6,7-dihydroxy-4-oxo-4H-1-benzopyran-3-carboxamido)acetamido]-7α-methoxy-3[1-(2-N,N-dimethylaminoethyl)-5-tetrazolyl]-thiomethyl-3-cephem-4-carboxylic acid;

7β-[D-2-(4-Carboxymethoxyphenyl)-2(6,7-dihydroxy-4-oxo-4H-1-benzopyran-3-carboxamido)acetamido]-3-[1-(2-N,N-dimethylaminoethyl)-5-tetrazolyl]thiomethyl-3-cephem-4-carboxylic acid;

7β-[D-2-(4-Carboxymethoxyphenyl)-2-(6,7-dihydroxy-2-methyl-4-oxo-4H-1-benzopyran-3-carboxamido)-acetamido]-7α-methoxy-3-[5-methyl-2-(1,3,4-thiadiazolyl)]thiomethyl-3-cephem-4-carboxylic acid;

7β-[D-2-(4-Carboxymethoxyphenyl)-2-(6,7-dihydroxy-2-methyl-4-oxo-4H-1-benzopyran-3-carboxamido)-acetamido]-3-[5-methyl-2-(1,3,4-thiadiazolyl)]thiomethyl-3-cephem-4-carboxylic acid;

7β-[D-2-(4-Carboxymethoxyphenyl)-2-(6,7-dihydroxy-4-oxo-4H-1-benzopyran-3-carboxamido)acetamido]-7α-methoxy-3-[5-methyl-2-(1,3,4-thiadiazolyl)]thiomethyl-3-cephem-4-carboxylic acid;

7β-[D-2-(4-Carboxymethoxyphenyl)-2-(6,7-dihydroxy-4-oxo-4H-1-benzopyran-3-carboxamido)acetamido]-3-[5-methyl-2-(1,3,4-thiadiazolyl)]thiomethyl-3-cephem-4-carboxylic acid;

7β-[D-2-(4-Carboxymethoxyphenyl)-2-(6,7-dihydroxy-2-methyl-4-oxo-4H-1-benzopyran-3-carboxamido)-acetamido]-7α-methoxy-3-[5-carboxymethyl-2-(1,3,4-thiadiazolyl)]thiomethyl-3-cephem-4-carboxylic acid;

7β-[D-2-(4-Carboxymethoxyphenyl)-2-(6,7-dihydroxy-2-methyl-4-oxo-4H-1-benzopyran-3-carboxamido)-acetamido]-3-[5-carboxymethyl-2-(1,3,4-thiadiazolyl)]-thiomethyl-3-cephem-4-carboxylic acid;

7β-[D-2-(4-Carboxymethoxyphenyl)-2-(6,7-dihydroxy-4-oxo-4H-1-benzopyran-3-carboxamido)acetamido]-7α-methoxy-3-[5-carboxymethyl-2-(1,3,4-thiadiazolyl)]-thiomethyl-3-cephem-4-carboxylic acid;

7β-[D-2-(4-Carboxymethoxyphenyl)-2-(6,7-dihydroxy-4-oxo-4H-1-benzopyran-3-carboxamido)acetamido]-3-[5-carboxymethyl-2-(1,3,4-thiadiazolyl)]thiomethyl-3-cephem-4-carboxylic acid;

7β-[D-2-(4-Carboxymethoxyphenyl)-2-(6,7-dihydroxy-2-methyl-4-oxo-4H-1-benzopyran-3-carboxamido)-acetamido]-7α-methoxy-3-[1-(2-sulfoethyl)-5-tetrazolyl]thiomethyl-3-cephem-4-carboxylic acid;

7β-[D-2-(4-Carboxymethoxyphenyl)-2-(6,7-diacetoxy-2-methyl-4-oxo-4H-1-benzopyran-3-carboxamido)-acetamido]-7α-methoxy-3-(1-carboxymethyl-5-tetrazolyl)thiomethyl-3-cephem-4-carboxylic acid;

7β-[D-2-(4-Carboxymethoxyphenyl)-2-(7,8-diacetoxy-2-methyl-4-oxo-4H-1-benzopyran-3-carboxamido)-acetamido]-7α-methoxy-3-(1-carboxymethyl-5-tetrazolyl)thiomethyl-3-cephem-4-carboxylic acid;

7β-[D-2-(4-Carboxymethoxyphenyl)-2-(6,7-diacetoxy-2-methyl-4-oxo-4H-1-benzopyran-3-carboxamido)-acetamido]-3-(1-carboxymethyl-5-tetrazolyl)thiomethyl-3-cephem-4-carboxylic acid;

7β-[D-2-(4-Carboxymethoxyphenyl)-2-(7,8-diacetoxy-2-methyl-4-oxo-4H-1-benzopyran-3-carboxamido)- acetamido]-3-(1-carboxymethyl-5-tetrazolyl)thiomethyl-3-cephem-4-carboxylic acid;

7β-[D-2-(4-Carboxymethoxyphenyl)-2-(6,7-diacetoxy-4-oxo-4H-1-benzopyran-3-carboxamido)acetamido]-7-methoxy-3-(1-carboxymethyl-5-tetrazolyl)thiomethyl-3-cephem-4-carboxylic acid;

7β-[D-2-(4-Carboxymethoxyphenyl)-2-(7,8-diacetoxy-4-oxo-4H-1-benzopyran-3-carboxamido)acetamido]-7α-methoxy-3-(1-carboxymethyl-5-tetrazolyl)thiomethyl-3-cephem-4-carboxlic acid;

7β-[D-2-(4-Carboxymethoxyphenyl)-2-(6,7-diacetoxy-4-oxo-4H-1-benzopyran-3-carboxamido)acetamido]-3-(1-carboxymethyl-5-tetrazolyl)thiomethyl-3-cephem-4-carboxylic acid;

7β-[D-2-(4-Carboxymethoxyphenyl)-2-(7,8-diacetoxy-4-oxo-4H-b 1-benzopyran-3-carboxamido)acetamido]-3-(1-carboxymethyl-5-tetrazolyl)thiomethyl-3-cephem-4-carboxylic acid;

7β-[D-2-(4-Carboxymethoxyphenyl)-2-(6,7-diacetoxy-2-oxo-2H-1-benzopyran-3-carboxamido)acetamido]-7α-methoxy-3-(1-carboxymethyl-5-tetrazolyl)thiomethyl-3-cephem-4-carboxylic acid;

7β-[D-2-(4-Carboxymethoxyphenyl)-2-(6,7-diacetoxy-2-oxo-2H-1-benzopyran-3-carboxamido)acetamido]-3-(1-carboxymethyl-5-tetrazolyl)thiomethyl-3-cephem-4-carboxylic acid;

7β-[D-2-(4-Carboxymethoxyphenyl)-2-(6,7-diacetoxy-1-ethyl-1,4-dihydro-4-oxoquinolin-3-carboxamido)acetamido]-7α-methoxy-3-(1-carboxymethyl-5-tetrazolyl)thiomethyl-3-cephem-4-carboxylic acid;

7β-[D-2-(4-Carboxymethoxyphenyl)-2-(6,7-diacetoxy-1-ethyl-1,4-dihydro-4-oxoquinolin-3-carboxamido)acetamido]-3-(1-carboxymethyl-5-tetrazolyl)thiomethyl-3-cephem-4-carboxylic acid;

7β-[D-2-(4-Carboxymethoxyphenyl)-2-(7,8-diacetoxy-1-methyl-1,4-dihydro-4-oxoquinolin-3-carboxamido)acetamido]-7α-methoxy-3-(1-carboxymethyl-5-tetrazolyl)thiomethyl-3-cephem-4-carboxylic acid;

7β-[D-2-(4-Carboxymethoxyphenyl)-2-(6,7-diacetoxy-2-methyl-4-oxo-4H-1-benzopyran-3-carboxamido)acetamido]-7α-methoxy-3-acetoxymethyl-3-cephem-4-carboxylic acid;

7β-[D-2-(4-Carboxymethoxyphenyl)-2-(7,8-diacetoxy-2-methyl-4-oxo-4H-1-benzopyran-3-carboxamido)acetamido]-7α-methoxy-3-acetoxymethyl-3-cephem-4-carboxylic acid;

7β-[D-2-(4-Carboxymethoxyphenyl)-2-(6,7-diacetoxy-2-methyl-4-oxo-4H-1-benzopyran-3-carboxamido)acetamido]-3-acetoxymethyl-3-cephem-4-carboxylic acid;

7β-[D-2-(4-Carboxymethoxyphenyl)-2-(7,8-diacetoxy-2-methyl-4-oxo-4H-1-benzopyran-3-carboxamido)acetamido]-3-acetoxymethyl-3-cephem-4-carboxylic acid;

7β-[D-2-(4-Carboxymethoxyphenyl)-2-(6,7-diacetoxy-4-oxo-4H-1-benzopyran-3-carboxamido)acetamido]-7α-methoxy-3-acetoxymethyl-3-cephem-4-carboxylic acid;

7β-[D-2-(4-Carboxymethoxyphenyl)-2-(7,8-diacetoxy-4-oxo-4H-1-benzopyran-3-carboxamido)acetamido]-7α-methoxy-3-acetoxymethyl-3-cephem-4-carboxylic acid;

7β-[D-2-(4-Carboxymethoxyphenyl)-2-(6,7-diacetoxy-4-oxo-4H-1-benzopyran-3-carboxamido)acetamido]-3-acetoxymethyl-3-cephem-4-carboxylic acid;

7β-[D-2-(4-Carboxymethoxyphenyl)-2-(7,8-diacetoxy-4-oxo-4H-1-benzopyran-3-carboxamido)acetamido]-3-acetoxymethyl-3-cephem-4-carboxylic acid;

7β-[D-2-(4-Carboxymethoxyphenyl)-2-(6,7-diacetoxy-2-oxo-2H-1-benzopyran-3-carboxamido)acetamido]-7α-methoxy-3-acetoxyemthyl-3-cephem-4-carboxylic acid;

7β-[D-2-(4-Carboxymethoxyphenyl)-2-(6,7-diacetoxy-1-ethyl-1,4-dihydro-4-oxoquinolin-3-carboxamido)-acetamido]-7α-methoxy-3-acetoxymethyl-3-cephem-4-carboxylic acid;

7β-[D-2-(4-Carboxymethoxyphenyl)-2-(6,7-diacetoxy-1-ethyl-1,4-dihydro-4-oxoquinolin-3-carboxamido)-acetamido]-3-acetoxymethyl-3-cephem-4-carboxylic acid;

7β-[D-2-(4-Carboxymethoxyphenyl)-2-(6,7-diacetoxy-2-methyl-4-oxo-4H-1-benzopyran-3-carboxamido)-acetamido]-7α-methoxy-3-(1-methyl-5-tetrazolyl)-thiomethyl-3-cephem-4-carboxylic acid;

7β-[D-2-(4-Carboxymethoxyphenyl)-2-(6,7-diacetoxy-4-oxo-4H-1-benzopyran-3-carboxamido)acetamido]-7α-methoxy-3-(1-methyl-5-tetrazolyl)thiomethyl-3-cephem-4-carboxylic acid;

7β-[D-2-(4-Carboxymethoxyphenyl)-2-(6,7-diacetoxy-4-oxo-4H-1-benzopyran-3-carboxamido)acetamido]-3-(1-methyl-5-tetrazolyl)thiomethyl-3-cephem-4-carboxylic acid;

7β-[D-2-(4-Carboxymethoxyphenyl)-2-(6,7-diacetoxy-1-ethyl-1,4-dihydro-4-oxoquinolin-3-carboxamido)-acetamido]-7α-methoxy-3-(1-methyl-5-tetrazolyl)-thiomethyl-3-cephem-4-carboxylic acid;

7β-[D-2-(4-Carboxymethoxyphenyl)-2-(6,7-diacetoxy-1-ethyl-1,4-dihydro-4-oxoquinolin-3-carboxamido)-acetamido]-3-(1-methyl-5-tetrazolyl)thiomethyl-3-cephem-4-carboxylic acid;

7β-[D-2-(4-Carboxymethoxyphenyl)-2-(6,7-diacetoxy-2-methyl-4-oxo-4H-1-benzopyran-3-carboxamido)-acetamido]-7α-methoxy-3-[5-methyl-2-(1,3,4-thiadiazolyl)]thiomethyl-3-cephem-4-carboxylic acid;

7β-[D-2-(4-Carboxymethoxyphenyl)-2-(6,7-diacetoxy--2-methyl-4-oxo-4H-1-benzopyran-3-carboxamido)acetamido]-7α-methoxy-3-[5-carboxymethyl-2-(1,3,4-thiadiazolyl)]-thiomethyl-3-cephem-4-carboxylic acid;

7β-[D-2-(4-Carboxymethoxyphenyl)-2-[6,7-bis(ethoxycarbonyloxy)-2-methyl-4-oxo-4H-1-benzopyran-3-carboxamido]acetamido]-3-acetoxymethyl-3-cephem-4-carboxylic acid;

7β-[D-2-(4-Carboxymethoxyphenyl)-2-[6,7-bis(ethoxycarbonyloxy)-2-methyl-4-oxo-4H-1-benzopyran-3-carboxamido]acetamido]3-(1-carboxymethyl-5-tetrazolyl)thiomethyl-3-cephem-4-carboxylic acid;

7β-[D-2-(4-Carboxymethoxyphenyl)-2-(6,7-dihydroxy-2-methyl-4-oxo-4H-1-benzopyran-3-carboxamido)-acetamido]-3-(4-carbamoylpyridinium)methyl-3-cephem-4-carboxylate;

7β-[D-2-(4-Carboxymethoxyphenyl)-2-(6,7-dihydroxy-4-oxo-4H-1-benzopyran-3-carboxamido)acetamido]-3-(4-carbamoylpyridinium)methyl-3-cephem-4-carboxylate;

7β-[D-2-(4-Carboxymethoxyphenyl)-2-(7,8-dihydroxy-2-methyl-4-oxo-4H-1-benzopyran-3-carboxamido)-acetamido]-3-(4-carbamoylpyridinium)methyl-3-cephem-4-carboxylate;

7β-[D-2-(4-Carboxymethoxyphenyl)-2-(7,8-dihydroxy-4-oxo-4H-1-benzopyran-3-carboxamido)acetamido]-3-(4-carbamoylpyridinium)methyl-3-cephem-4-carboxylate;

7β-[D-2-(4-Carboxymethoxyphenyl)-2-(6,7-dihydroxy-2-methyl-4-oxo-4H-1-benzopyran-3-carboxamido)- acetamido]-3-[4-(2-sulfoethyl)pyridinium]methyl-3-cephem-4-carboxylate;

7β-[D-2-(4-Carboxymethoxyphenyl)-2-(6,7-dihydroxy-4-oxo-4H-1-benzopyran-3-carboxamido)acetamido]-3-[4-(2-sulfoethyl)pyridinium]methyl-3-cephem-4-carboxylate;

7β-[D-2-(4-Carboxymethoxyphenyl)-2-(7,8-dihydroxy-2-methyl-4-oxo-4H-1-benzopyran-3-carboxamido)acetamido]-3-[4-(2-sulfoethyl)pyridinium]methyl-3-cephem-4-carboxylate;

7β-[D-2-(4-Carboxymethoxyphenyl)-2-(7,8-dihydroxy-4-oxo-4-H-1-benzopyran-3-carboxamido)acetamido]-3-[4-(2-sulfoethyl)pyridinium]methyl-3-cephem-4-carboxylate;

7β-[D-2-(4-Carboxymethoxyphenyl)-2-(6,7-dihydroxy-2-methyl-4-oxo-4H-1-benzopyran-3-carboxamido)acetamido]-3-(3-carboxymethylpyridinium)methyl-3-cephem-4-carboxylate;

7β-[D-2-(4-Carboxymethoxyphenyl)-2-(6,7-dihydroxy-4-oxo-4H-1-benzopyran-3-carboxamido)acetamido]-3-(3-carboxymethylpyridinium)methyl-3-cephem-4-carboxylate;

7β-[D-2-(4-Carboxymethoxyphenyl)-2-(7,8-dihydroxy-2-methyl-4-oxo-4H-1-benzopyran-3-carboxamido)acetamido]-3-(3-carboxymethylpyridinium)methyl-3-cephem-4-carboxylate;

7β-[D-2-(4-Carboxymethoxyphenyl)-2-(7,8-dihydroxy-4-oxo-4H-1-benzopyran-3-carboxamido)acetamido]-3-(3-carboxymethylpyridinium)methyl-3-cephem-4-carboxylate;

7β-[D-2-(4-Carboxymethoxyphenyl)-2-(6,7-dihydroxy-2-methyl-4-oxo-4H-1-benzopyran-3-carboxamido)acetamido]-3-pyridinium-methyl-3-cephem-4-carboxylate;

7β-[D-2-(4-Carboxymethoxyphenyl)-2-(6,7-dihydroxy-4-oxo-4H-1-benzopyran-3-carboxamido)acetamido]-3-pyridiniummethyl-3-cephem-4-carboxylate;

7β-[D-2-(4-Carboxymethoxyphenyl)-2-(7,8-dihydroxy-2-methyl-4-oxo-4H-1-benzopyran-3-carboxamido)acetamido]-3-pyridiniummethyl-3-cephem-4-carboxylate;

7β-[D-2-(4-Carboxymethoxyphenyl)-2-(7,8-dihydroxy-4-oxo-4H-1-benzopyran-3-carboxamido)acetamdo]-3-pyridiniummethyl-3-cephem-4-carboxylate;

7β-[D-2-(4-Carboxymethoxyphenyl)-2-(6,7-dihydroxy-2-methyl-4-oxo-4H-1-benzopyran-3-caboxamido)acetamido]-3-(4-N-hydroxycarbamoylpyridinium)-methyl-3-cephem-4-carboxylate;

7β-[D-2-(4-Carboxymethoxyphenyl)-2-(6,7-dihydroxy-4-oxo-4H-1-benzopyran-3-carboxamido)acetamido]-3-(4-N-hydroxycarbamoylpyridinium)methyl-3-cephem-4-carboxylate;

7β-[D-2-(4-Carboxymethoxyphenyl)-2-(7,8-dihydroxy-2-methyl-4-oxo-4H-1-benzopyran-3-carboxamido)acetamido]-3-(4-N-hydroxycarbamoylpyridinium)-methyl-3-cephem-4-carboxylate;

7β-[D-2-(4-Carboxymethoxyphenyl)-2-(7,8-dihydroxy-4-oxo-4H-1-benzopyran-3-carboxamido)acetamido]-3-(4-N-hydroxycarbamoylpyridinium)methyl-3-cephem-4-carboxylate;

7β-[D-2-(4-Carboxymethoxyphenyl)-2-(6,7-dihydroxy-2-methyl-4-oxo-4H-1-benzopyran-3-carboxamido)acetamido]-3-(4-cyanopyridinium)methyl-3-cephem-4caboxylate;

7β-[D-2-(4-Carboxymethoxyphenyl)-2-(6,7-dihydroxy-4-oxo-4H-1-benzopyran-3-carboxamido)acetamido]-3-(4-cyanopyridinium)methyl-3-cephem-4-carboxylate;

7β-[D-2-(4-Carboxymethoxyphenyl)-2-(7,8-dihydroxy-2-methyl-4-oxo-4H-1-benzopyran-3-carboxamido)acetamido]-3-(4-cyanopyridinium)methyl-3-cephem-4-carboxylate;

7β-[D-2-(4-Carboxymethoxyphenyl)-2-(7,8-dihydroxy-4-oxo-4H-1-benzopyran-3-carboxamido)acetamido]-3-(4-cyanopyridinium)methyl-3-cephem-4-carboxylate;

7β-[D-2-(4-Carboxymethoxyphenyl)-2-(6,7-dihydroxy-2-methyl-4-oxo-4H-1-benzopyran-3-carboxamido)acetamido]-3-[4-(2-N,N-dimethylaminoethyl)-pyridinium]-methyl-3-cephem-4-carboxylate;

7β-[D-2-(4-Carboxymethoxyphenyl)-2-(6,7-dihydroxy-4-oxo-4H-1-benzopyran-3-carboxamido)acetamido]-3-[4-(2-N,N-dimethylaminoethyl)pyridinium]methyl-3-cephem-4-carboxylate;

7β-[D-2-(4-Carboxymethoxyphenyl)-2-(7,8-dihydroxy-2-methyl-4-oxo-4H-1-benzopyran-3-carboxamido)acetamido]-3-[4-(2-N,N-dimethylaminoethyl)-pyridinium]-methyl-3-cephem-4-carboxylate;

7β-[D-2-(4-Carboxymethoxyphenyl)-2-(7,8-dihydroxy-4-oxo-4H-1-benzopyran-3-carboxamido)acetamido]-3-[4-(2-N,N-dimethylaminoethyl)pyridinium]methyl-3-cephem-4-carboxylate;

7β-[D-2-(4-Carboxymethoxyphenyl)-2-(6,7-dihydroxy-2-methyl-4-oxo-4H-1-benzopyran-3-carboxamido)acetamido]-3-(4-sulfopyridinium)methyl-3-cephem-4-carboxylate;

7β-[D-2-(4-Carboxymethoxyphenyl)-2-(6,7-dihydroxy-4-oxo-4-H-1-benzopyran-3-carboxamido)acetamido]-3-(4-sulfopyridinium)methyl-3-cephem-4-carboxylate;

7β-[D-2-(4-Carboxymethoxyphenyl)-2-(6,7-dihydroxy-2-methyl-4-oxo-4H-1-benzopyran-3-caboxamido)acetamido]-3-(3-carboxypyridinium)methyl-3-cephem-4-carboxylate;

7β-[D-2-(4-Carboxymethoxyphenyl)-2-(6,7-dihydroxy-4-oxo-4H-1-benzopyran-3-carboxamido)acetamido]-3-(3-carboxypyridinium)methyl-3-cephem-4-carboxylate;

7β-[D-2-(4-Carboxymethoxyphenyl)-2-(6,7-dihydroxy-1-ethyl-1,4-dihydro-4-oxoquinoline-3-carboxamido)acetamido]-3-(4-carbamoylpyridinium)methyl-3-cephem-4-carboxylate;

7β-[D-2-(4-Carboxymethoxyphenyl)-2-(6,7-dihydroxy-1,4-dihydro-4-oxoquinoline-3-carboxamido)acetamido]-3-(4-carbamoylpyridinium)methyl-3-cephem-4-carboxylate;

7β-[D-2-(4-Carboxymethoxyphenyl)-2-(7,8-dihydroxy-1-ethyl-1,4-dihydro-4-oxoquinoline-3-carboxamido)acetamido]-3-(4-carbamoylpyridinium)methyl-3-cephem-4-carboxylate;

7β-[D-2-(4-Carboxymethoxyphenyl)-2-(6,7-dihydroxy-1-ethyl-1,4-dihydro-4-oxoquinoline-3-carboxamido)acetamido]-3-[4-(2-sulfoethyl)pyridinium]methyl-3-cephem-4-carboxylate;

7β-[D-2-(4-Carboxymethoxyphenyl)-2-(6,7-dihydroxy-1-ethyl-1,4-dihydro-4-oxoquinoline-3-carboxamido)acetamido]-3-(3-carboxymethylpyridinium)methyl-3-cephem-4-carboxylate;

7β-[D-2-(4-Carboxymethoxyphenyl)-2-(6,7-dihydroxy-2-methyl-4-oxo-4H-1-benzopyran-3-carboxamido)acetamido]-7α-methoxy-3-(4-carbamoylpyridinium)methyl-3-cephem-4-carboxylate;

7β-[D-2-(4-Carboxymethoxyphenyl)-2-(6,7-dihydroxy-4-oxo-4H-1-benzopyran-3-carboxamido)acetamido]-7α-methoxy-3-(4-carbamoylpyridinium)methyl-3-cephem-4-carboxylate;

7β-[D-2-(4-Carboxymethoxyphenyl)-2-(7,8-dihydroxy-2-methyl-4-oxo-4H-1-benzopyran-3-carboxamido)-acetamido]-7α-methoxy-3-(4-carbamoylpyridinium)-methyl-3-cephem-4-carboxylate;

7β-[D-2-(4-Carboxymethoxyphenyl)-2-(7,8-dihydroxy-4-oxo-4H-1-benzopyran-3-carboxamido)acetamido]-7α-methoxy-3-(4-carbamoylpyridinium)methyl-3-cephem-4-carboxylate;

7β-[D-2-(4-Carboxymethoxyphenyl)-2-(6,7-dihydroxy-2-methyl-4-oxo-4H-1-benzopyran-3-carboxamido)-acetamido]-7α-methoxy-3-[4-(2-sulfoethyl)pyridinium]-methyl-3-cephem-4-carboxylate;

7β-[D-2-(4-Carboxymethoxyphenyl)-2-(6,7-dihydroxy-4-oxo-4H-1-benzopyran-3-carboxamido)acetamido]-7α-methoxy-3-[4-(2-sulfoethyl)pyridinium]methyl-3-cephem-4-carboxylate;

7β-[D-2-(4-Carboxymethoxyphenyl)-2-(7,8-dihydroxy-2-methyl-4-oxo-4H-1-benzopyran-3-carboxamido)-acetamido]-7α-methoxy-3-[4-(2-sulfoethyl)pyridinium]-methyl-3-cephem-4-carboxylate;

7β-[D-2-(4-Carboxymethoxyphenyl)-2-(7,8-dihydroxy-4-oxo-4H-1-benzopyran-3-carboxamido)acetamido]-7α-methoxy-3-[4-(2-sulfoethyl)pyridinium]methyl-3-cephem-4-carboxylate;

7β-[D-2-(4-Carboxymethoxyphenyl)-2-(6,7-dihydroxy-2-methyl-4-oxo-4H-1-benzopyran-3-carboxamido)-acetamido]-7α-methoxy-3-(3-carboxymethylpyridinium)-methyl-3-cephem-4-carboxylate;

7β-[D-2-(4-Carboxymethoxyphenyl)-2-(6,7-dihydroxy-4-oxo-4H-1-benzopyran-3-carboxamido)acetamido]-7α-methoxy-3-(3-carboxymethylpyridinium)methyl-3-cephem-4-carboxylate;

7β-[D-2-(4-Carboxymethoxyphenyl)-2-(7,8-dihydroxy-2-methyl-4-oxo-4H-1-benzopyran-3-carboxamido)-acetamido]-7α-methoxy-3-(3-carboxymethylpyridinium)-methyl-3-cephem-4-carboxylate;

7β-[D-2-(4-Carboxymethoxyphenyl)-2-(7,8-dihydroxy-4-oxo-4H-1-benzopyran-3-carboxamido)acetamido]-7α-methoxy-3-(3-(carboxymethylpyridinium)methyl-3-cephem-4-carboxylate;

7β-[D-2-(4-Carboxymethoxyphenyl)-2-(6,7-dihydroxy-2-methyl-4-oxo-4H-1-benzopyran-3-carboxamido)-acetamido]-7α-methoxy-3-pyridiniummethyl-3-cephem-4carboxylate;

7β-[D-2-(4-Carboxymethoxyphenyl)-2-(6,7-dihydroxy-4-oxo-4H-1-benzopyran-3-carboxamido)acetamido]-7α-methoxy-3-pyridiniummethyl-3-cephem-4-carboxylate;

7β-[D-2-(4-Carboxymethoxyphenyl)-2-(7,8-dihydroxy-2-methyl-4-oxo-4H-1-benzopyran-3-carboxamido)-acetamido]-7α-methoxy-3-pyridiniummethyl-3-cephem-4-carboxylate;

7β-[D-2-(4-Carboxymethoxyphenyl)-2-(7,8-dihydroxy-4-oxo-4H-1-benzopyran-3-carboxamido)acetamido]-7α-methoxy-3-pyridiniummethyl-3-cephem-4-carboxylate;

7β-[D-2-(4-Carboxymethoxyphenyl)-2-(6,7-dihydroxy-2-methyl-4-oxo-4H-1-benzopyran-3-carboxamido)-acetamido]-7α-methoxy-3-(4-N-hydroxycarbamoylpyridinium)methyl-3-cephem-4-carboxylate;

7β-[D-2-(4-Carboxymethoxyphenyl)-2-(6,7-dihydroxy-4-oxo-4H-1-benzopyran-3-carboxamido)acetamido]-7α-methoxy-3-(4-N-hydroxycarbamoylpyridinium)-methyl-3-cephem-4-carboxylate;

7β-[D-2-(4-Carboxymethoxyphenyl)-2-(7,8-dihydroxy-2-methyl-4-oxo-4H-1-benzopyran-3-carboxamido)-acetamido]-7α-methoxy-3-(4-N-hydroxycarbamoylpyridinium)methyl-3-cephem-4-carboxylate;

7β-[D-2-(4Carboxymethoxyphenyl)-2-(7,8-dihydroxy-4-oxo-4H-1-benzopyran-3-carboxamido)acetamido]-7α-methoxy-3-(4-N-hydroxycarbamoylpyridinium)-methyl-3-cephem-4-carboxylate;

7β-[D-2-(4-Carboxymethoxyphenyl)-2-(6,7-dihydroxy-2-methyl-4-oxo-4H-1-benzopyran-3-carboxamido)-acetamido]-7α-methoxy-3-(4-cyanopyridinium)methyl-3-cephem-4-carboxylate;

7β-[D-2-(4-Carboxymethoxyphenyl)-2-(6,7-dihydroxy-4-oxo-4H-1-benzopyran-3-carboxamido)acetamido]-7α-methoxy-3-(4-cyanopyridinium)methyl-3-cephem-4-carboxylate;

7β-[D-2-(4-Carboxymethoxyphenyl)-2-(7,8-dihydroxy-2-methyl-4-oxo-4H-1-benzopyran-3-carboxamido)-acetamido]-7α-methoxy-3-(4-cyanopyridinium)methyl-3-cephem-4-carboxylate;

7β-[D-2-(4-Carboxymethoxyphenyl)-2-(7,8-dihydroxy-4-oxo-4H-1-benzopyran-3-carboxamido)acetamido]-7α-methoxy-3-(4-cyanopyridinium)methyl-3-cephem-4-carboxylate;

7β-[D-2-(4-Carboxymethoxyphenyl)-2-(6,7-dihydroxy-y-2-methyl-4-oxo-4H-1-benzopyran-3-carboxamido)-acetamido]-7α-methoxy-3-[4-(2-N,N-dimethylaminoethyl)-pyridinium]methyl-3-cephem-4-carboxylate;

7β-[D-2-(4-Carboxymethoxyphenyl)-2-(6,7-dihydroxy-4-oxo-4H-1-benzopyran-3-carboxamido)acetamido]-7α-methoxy-3-[4-(2-N,N-dimethylaminoethyl)-pyridinium]-methyl-3-cephem-4-carboxylate;

7β-[D-2-(4-Carboxymethoxyphenyl)-2-(7,8-dihydroxy-y-2-methyl-4-oxo-4H-1-benzopyran-3-carboxamido)-acetamido]-7α-methoxy-3-[4-(2-N,N-dimethylaminoethyl)-pyridinium]methyl-3-cephem-4-carboxylate;

7β-[D-2-(4-Carboxymethoxyphenyl)-2-(7,8-dihydroxy-4-oxo-4H-1-benzopyran-3-carboxamido)acetamido]-7α-methoxy-3-[4-(2-N,N-dimethylaminoethyl)-pyridinium]-methyl-3-cephem-4-carboxylate;

7β-[D-2-(4-Carboxymethoxyphenyl)-2-(6,7-dihydroxy-2-methyl-4-oxo-4H-1-benzopyran-3-carboxamido)-acetamido]-7α-methoxy-3-(4-sulfopyridinium)methyl-3-cephem-4-carboxylate;

7β-[D-2-(4-Carboxymethoxyphenyl)-2-(6,7-dihydroxy-4-oxo-4H-1-benzopyran-3-carboxamido)acetamido]-7α-methoxy-3-(4-sulfopyridinium)methyl-3-cephem-4-carboxylate;

7β-[D-2-(4-Carboxymethoxyphenyl)-2-(6,7-dihydroxy-2-methyl-4-oxo-4H-1-benzopyran-3-carboxamido)-acetamido]-7α-methoxy-3-(3-carboxypyridinium)-methyl-3-cephem-4-carboxylate;

7β-[D-2-(4-Carboxymethoxyphenyl)-2-(6,7-dihydroxy-4-oxo-4H-1-benzopyran-3-carboxamido)acetamido]-7α-methoxy-3-(3-carboxypyridinium)methyl-3-cephem-4-carboxylate;

7β-[D-2-(4-Carboxymethoxyphenyl)-2-(6,7-dihydroxy-1-ethyl-1,4-dihydro-4-oxoquinoline-3-carboxamido)-acetamido]-7α-methoxy-3-(4-carbamoylpyridinium)-methyl-3-cephem-4-carboxylate;

7β-[D-2-(4-Carboxymethoxyphenyl)-2-(6,7-dihydroxy-1,4-dihydro-4-oxoquinoline-3-carboxamido)acetamido]-7α-methoxy-3-(4-carbamoylpyridinium)methyl-3-cephem-4-caboxylate;

7β-[D-2-(4-Carboxymethoxyphenyl)-2-(7,8-dihydroxy-1-ethyl-1,4-dihydro-4-oxoquinoline-3-carboxamido)-acetamido]-7α-methoxy-3-(4-carbamoylpyridinium)-methyl-3-cephem-4-carboxylate;

7β-[D-2-(4-Carboxymethoxyphenyl)-2-(6,7-dihydroxy-1-ethyl-1,4-dihydro-4-oxoquinoline-3-carboxamido)acetamido]-7α-methoxy-3-[4-(2-sulfoethyl)pyridinium]-methyl-3-cephem-4-carboxylate;

7β-[D-2-(4-Carboxymethoxyphenyl)-2-(6,7-dihydroxy-1-ethyl-1,4-dihydro-4-oxoquinoline-3-carboxamido)-acetamido]-7α-methoxy-3-(3-carboxymethylpyridinium)-methyl-3-cephem-4-carboxylate;

7β-[D-2-(4-Carboxymethoxyphenyl)-2-(6,7-dihydroxy-2-methyl-4-oxo-4H-1-benzopyran-3-carboxyamido)acetamido]-3-(4-carboxypyridimium)-methyl-3-cephem-4-carboxylate;

7β-[D-2-(4-Carboxymethoxyphenyl)-2-(6,7-dihydroxy-2-methyl-4-oxo-4H-1-benzopyran-3-carboxamido)acetamido]-3-(3-carbamoylpyridinum)-methyl-3-cephem-4-carboxylate; and 7β-[D-2-(4-Carboxymethoxyphenyl)-2-(6,7-dihydroxy-2-methyl-4-oxo-4H-1-benzopyran-3-carboxamido)acetamido]-3-(4-N-hydroxy-N-methyl-carbmoylpyridinum)methyl-3-cephem-4-carboxylate.

The compounds according to this invention exhibit strong antibacterial activities especially against gram-negative bacteria such as *Pseud. aeruginosa, Kleb. pneumoniae*, and *Ser. marcescens*. The acute toxicity values [LD$_{50}$(mouse, oral)] of the following compounds were each 4 g/kg or greater;

Sodium 7β-[D-2-(4-carboxymethoxyphenyl)-2-(6,7-dihydroxy-2-methyl-4-oxo-4H-1-benzopyran-3-carboxamido)acetamido]-7α-methoxy-3-(1-carboxymethyl-5-tetrazolyl)thiomethyl-3-cephem-4-carboxylate;

Trisodium 7β-[D-2-(4-carboxymethoxyphenyl)-2-(6,7-dihydroxy-2-methyl-4-oxo-4H-1-benzopyran-3-carboxamido)acetamido]-3-(1-carboxymethyl-5-tetrazolyl)thiomethyl-3-cephem-4-carboxylate;

Trisodium 7β-[D-2-(4-carboxymethoxyphenyl)-2-(6,7-dihydroxy-4-oxo-4H-1-benzopyran-3-carboxamido)-acetamido]-7α-methoxy-3-(1-carboxymethyl-5-tetrazolyl)thiomethyl-3-cephem-4-carboxylate;

7β-[D-2-(4-Carboxymethoxyphenyl)-2-(6,7-diacetoxy-1-ethyl-1,4-dihydro-4-oxoquinolin-3-carboxamido)-acetamido]-3-(1-methyl-5-tetrazolyl)thiomethyl-3-cephem-4-carboxylic acid;

Sodium 7β-[D-2-(4-carboxymethoxyphenyl)-2-(6,7-dihydroxy-2-methyl-4-oxo-4H-1-benzopyran-3-carboxamido)acetamido]-3-(4-carbamoylpyridinium)-methyl-3-cephem-4-carboxylate;

Disodium 7β-[D-2-(4-carboxymethoxyphenyl)-2-(6,7-dihydroxy-2-methyl-4-oxo-4H-1-benzopyran-3-carboxamido)acetamido]-3-[4-(2-sulfoethyl)-pyridinium]methyl-3-cephem-4-carboxylate;

Disodium 7β-[D-2-(4-carboxymethoxyphenyl)-2-(6,7-dihydroxy-2-methyl-4-oxo-4H-1-benzopyran-3-carboxamido)acetamido]-3-(3-carboxymethylpyridinium)-methyl-3-cephem-4-carboxylate;

Sodium 7β-[D-2-(4-carboxymethoxyphenyl)-2-(6,7-dihydroxy-1-ethyl-1,4-dihydro-4-oxoquinoline-3-carboxamido)acetamido]-3-(4-carbamonylpyridinium)-methyl-3-cephem-4-carboxylate;

Sodium 7β-[D-2-(4-carboxymethoxyphenyl)-2-(6,7-dihydroxy-2-methyl-4-oxo-4H-1-benzopyran-3-carboxamido)acetamido]-7α-methoxy-3-pyridinium-methyl-3-cephem-4-carboxylate;

Sodium 7β-[D-2-(4-carboxymethoxyphenyl)-2-(6,7-dihydroxy-2-methyl-4-oxo-4H-1-benzopyran-3-carboxamido)acetamido]-7α-methoxy-3-(4-carbamoylpyridinium)methyl-3-cephem-4-carboxylate;

7β-[D-2-(4-Carboxymethoxyphenyl)-2-(6,7-dihydroxy-2-methyl-4-oxo-4H-1-benzopyran-3-carboxamido)acetamido]-3-(4-carbamoylpyridinum)-methyl-3-cephem-4-carboxylate; and 7β-[D-2-(4-Carboxymethoxyphenyl)-2-(6,7-dihydroxy-2-methyl-4-oxo-4H-1-benzopyran-3-carboxamido)acetamido-3-(4-carboxypyridinum)-methyl-3-cephem-4-carboxylate disodium salt.

Thus, the compounds according to this invention are useful as antibacterial agents. When using the compounds of this invention as antibacterial agents, their dosages may generally be 2–300 mg/kg/day with 10–100 mg/kg/day being preferred. The antibacterial agents according to this invention may each be administered by the oral route in the form of powder, granules, capsules or tablets or by the parenteral routes in the form of injectable preparations or suppositories. These preparations may be produced by methods commonly known in the art, using a therapeutically effective amount of a compound of this invention and a pharmaceutically acceptable carrier.

The following examples illustrate this invention, but are not to be construed as limiting the scope thereof.

EXAMPLE 1

7β-[D-2-(4-Carboxymethoxyphenyl)-2-(6,7-dihydroxy-4-oxo-4H-1-benzopyran-3-carboxamido)-acetamido]-3-acetoxymethyl-3-cephem-4-carboxylic acid (a) p-Methoxybenzyl bromoacetate:

Bromoacetyl bromide (24 g) was dissolved in dichloromethane (200 ml), followed by a dropwise addition of the dichloromethane solution (200 ml) of p-methoxy benzyl alcohol (16.4 g) and pyridine (9.41 g) with stirring at 0° C. The resultant mixture was stirred for further 30 minutes. After washing the liquid reaction mixture with water, it was dried with anhydrous magnesium sulfate and the solvent was evaporated. The residue was purified by silica gel column chromatography (hexane: benzene=2:3) to obtain the desired product (27.15 g).

(b) 7β-[D-2-(4-Hydroxyphenyl)-2-(p-methoxybenzyloxycarbonylamino)acetamido]-3-acetoxymethyl-3-cephem-4-carboxylic acid:

A mixture of triethylamine (10.45 ml) and water (70 ml) was continuously stirred with ice-cooling, to which 7β-[D-2-(4-hydroxyphenyl)-2-aminoacetamido]-3-acetoxymethyl-3-cephem-4-carboxylic acid (21.1 g) was added and dissolved. To the resulting solution, a dimethylformamide solution (75 ml) of p-methoxybenzyl-S-(4,6-dimethylpyridin-2-yl)thiocarbonate (15.2 g) was added dropwise over 15 minutes with ice-cooling. After stirring the thus-obtained mixture at the same temperature for 20 minutes, it was stirred at room temperature for further 1 hour and 30 minutes. Water (300 ml) was added to the liquid reaction mixture, followed by washing the resulting aqueous solution with ethyl acetate. Ethyl acetate (200 ml) was then added to the water layer, followed by an addition, with stirring at 0° C., of 1N-hydrochloric acid (60 ml). The ethyl acetate layer and water layer were separated from each other. The water layer was extracted three times with ethyl acetate (200 ml in total) and the resulting ethyl acetate solution was combined with the above ethyl acetate layer. After drying the thus-obtained ethyl acetate solution over anhydrous magnesium sulfate, the solvent was evaporated. The residue was suspended in a 2:1 mixed solvent of ethyl ether and hexane and then stirred. The resulting solid was collected by filtration to obtain the desired product (25.86 g).

Infrared absorption spectrum[cm$^{-1}$, Nujol(trademark)]: 1780, 1720, 1665, 1610.

NMR spectrum(δ, DMSO-d$_6$): 2.01(3H, s), 3,34(1H, d, J=18 Hz), 3.54(1H, d, J=18 Hz), 3.73(3H, s), 4.63(1H, d, J=12 Hz), 4.85–5.1(4H, m), 5.26(1H, d, J=8 Hz), 5.68(1H, dd, J=8 Hz, 5 Hz), 6.65(2H, d, J=8 Hz), 6.88(2H, d, J=8 Hz), 7.20(2H, d, J=8 Hz), 7.27(2H, d, J=8 Hz), 7.73(1H, d, J=8 Hz), 9.06(1H, d, J=8 Hz).

(c) 7β-[D-2-[4-(p-Methoxybenzyloxycarbonylmethoxy)phenyl]-2-(p-methoxybenzyloxycarbonylamino)acetamido]-3-acetoxymethyl-3-cephem-4-carboxylic acid:

To a suspension of 55% sodium hydride (44 mg, 1 millimole) in a 1:1 mixture of dimethylformamide and tetrahydrofuran (4 ml), was added dropwise, with stirring and with cooling in dry ice-acetone bath a solution of the compound obtained in the above procedure (b) (293 mg) in a 1:1 mixture of dimethylformamide and tetrahydrofuran (4 ml). After stirring the resulting mixture for 5 minutes while cooling it in the same temperature, a solution of p-methoxybenzyl bromoacetate (130 mg) in tetrahydrofuran (1 ml) was added dropwise with stirring. The resulting mixture was stirred for further 20 minutes while cooling it in the same temperature and then for further 2 hours at room temperature. The liquid reaction mixture was poured in ethyl acetate (100 ml) and was washed successively with 0.2N-hydrochloric acid, water and a saturated aqueous solution of sodium chloride. After drying the thus-washed liquid reaction mixture over anhydrous magnesium sulfate, the solvent was evaporated. The residue was purified by thin-layer silica gel chromatography to obtain the desired product (149 mg).

Infrared absorption spectrum[cm$^{-1}$, Nujol(trade mark)]: 1755, 1720, 1650, 1610.

NMR spectrum(δ, DMSO-d$_6$-D$_2$O): 2.01(3H, s), 3.28(1H, d, J=17 Hz), 3.52(1H, d, J=17 Hz), 3.73(6H, s), 4.65(1H, d, J=13 Hz), 4.8–5.03(4H, m), 5.10(2H, s), 5.28(1H, s), 5.64(1H, d, J=4.5 Hz), 6.7–7.0(6H, m), 7.1–7.45(6H, m).

(d) Trifluoroacetic acid salt of 7β-[D-2-amino-2-(4-carboxymethoxyphenyl)acetamido]-3-acetoxymethyl-3-cephem-4-carboxylic acid:

The compound obtained in the above procedure (c) (125 mg) was added, with stirring at 0° C., to a 2.5:1 liquid mixture of trifluoroacetic acid and anisole (1.5 ml). After stirring the resulting mixture at 0° C. for 2 hours and 30 minutes, a 2:1 mixture of ethyl ether and hexane (15 ml) was added. The resulting precipitate was collected by filtration and then washed with ethyl ether to obtain the desired product (90 mg).

Infrared absorption spectrum[cm$^{-1}$, Nujol(trade mark)]: 1765, 1720, 1660–1710, 1605.

NMR spectrum(δ, DMSO-d$_6$-D$_2$O): 2.00(3H, s), 3.30(1H, d, J=18 Hz), 3.54(1H, d, J=18 Hz), 4.64(1H, d, J=12 Hz), 4.69(2H, s), 4.8–5.1(3H, m), 5.51(1H, d, J=5 Hz), 6.96(2H, d, J=8 Hz), 7.40(2H, d, J=8 Hz).

(e) 7β-[D-2-(4-Carboxymethoxyphenyl)-2-(6,7-dihydroxy-4-oxo-4H-1-benzopyran-3-carboxamido)acetamido]-3-acetoxymethyl-3-cephem-4-carboxylic acid:

The compound obtained in the above procedure (d) (59 mg) was suspended in tetrahydrofuran, followed by an addition of N,O-bis(trimethylsilyl)acetamide (111 μl). The resulting mixture was cooled to 0° C., to which 6,7-dihydroxy-4-oxo-4H-1-benzopyran-3-carbonyl chloride (26 mg) was added. Thereafter, the resulting mixture was stirred for 2 hours. After adding ethyl acetate (60 ml) to the liquid reaction mixture, the resulting mixture was washed successively with 0.2N-hydrochloric acid, water and a saturated aqueous solution of sodium chloride. The thus-washed mixture was then dried over anhydrous magnesium sulfate and the solvent was evaporated. The residue was dissolved in tetrahydrofuran (2 ml) and then added dropwise with stirring to ethyl ether (30 ml). The resulting precipitate was collected by filtration and washed with ethyl ether to obtain the desired product (50 mg).

Infrared absorption spectrum[cm$^{-1}$, Nujol(trade mark)]: 1750–1780, 1710–1740, 1655, 1605.

NMR spectrum(δ, DMSO-d$_6$): 2.01(3H, s), 4.65(1H, d, J=12 Hz), 4.66(2H, s), 4.98(1H, d, J=12 Hz), 5.03(1H, d, J=5 Hz), 5.65–5.85(2H, m), 6.89(2H, d, J=8.5 Hz), 6.97(1H, s), 7.36(2H, d, J=8.5 Hz), 7.41(1H, s), 8.83(1H, s), 9.40(1H, d, J=8 Hz), 10.30(1H, d, J=8 Hz).

EXAMPLE 2

Disodium 7β-[D-2-(4-carboxymethoxyphenyl)-2-(6,7-dihydroxy-4-oxo-4H-1-benzopyran-3-carboxamido]-3-acetoxymethyl-3-cephem-4-carboxylate A 1M-solution of sodium acetate in methanol (277 μl) was added to a mixture of 7β-[D-2-(4-carboxymethoxyphenyl)-2-(6,7-dihydroxy-4-oxo-4H-1-benzopyran-3-carboxamido)acetoamido]-3-acetoxymethyl-3-cephem-4-carboxylic acid (90 mg) and methanol (5 ml), followed by an addition of methanol (10 ml). The insoluble matter was removed by filtration and the filtrate was concentrated. The residue was washed first with ethanol and then with ethyl ether to obtain the desired product (84 mg).

Infrared absorption spectrum[cm$^{-1}$, Nujol(trade mark)]: 1740–1770, 1660, 1600.

NMR spectrum(δ, DMSO-d$_6$): 2.00(3H, s), 3.17(1H, d, J=17 Hz), 3.42(1H, d, J=17 Hz), 4.31(2H, s), 4.75(1H, d, J=12 Hz), 4.82(1H, d, J=5 Hz), 5.02(1H, d, J=12 Hz), 5.58(1H, dd, J=8 Hz, 5 Hz), 5.80(1H, d, J=8 Hz), 6.77(1H, s), 6.84(2H, d, J=8 Hz), 7.27(1H, s), 7.34(2H, d, J=8 Hz), 8.76(1H, s).

Solubility (in distilled water at 25° C.): 20% or higher.

EXAMPLE 3

7β-[D-2-(4-Carboxymethoxyphenyl)-2-(6,7-dihydroxy-4-oxo-4H-1-benzopyran-3-carboxamido)acetamido]-3-(1-methyl-5-tetrazolyl)thiomethyl-3-cephem-4-carboxylic acid (a) 7β-[D-2-[4-p-Methoxybenzyloxycarbonylmethoxy)phenyl]-2-(p-methoxybenzyloxycarbonylamino)acetamido]-3-(1-methyl-5-tetrazolyl)thiomethyl-3-cephem-4-carboxylic acid:

A mixture of 7β-[D-2-[4-(p-methoxybenzyloxycarbonylmethoxy)phenyl]-2-(p-methoxybenzyloxycarbonylamino)acetamido]-3-acetoxymethyl-3-cephem-4-carboxylic acid (1.528 g), 1-methyl-5-mercaptotetrazole (1.16 g) and acetonitrile (60 ml) was heated under reflux for 9 hours and the solvent was then evaporated. The residue was taken up in tetrahydrofuran (10 ml), followed by a dropwise addition with stirring of the resulting solution to ethyl ether (150 ml). The precipitate was collected by filtration and then purified by silica gel column chromatography (ethyl acetate:methanol:formic acid=990:10:1) to obtain the desired product (755 mg).

Infrared absorption spectrum[cm$^{-1}$, Nujol(trade mark)]: 1780, 1720, 1660, 1605.

NMR spectrum(δ, DMSO-d₆): 3.47(1H, d, J=18 Hz), 3.68(1H, d, J=18 Hz), 3.71(3H, s), 3.72(3H, s), 3.90(3H, s), 4.17(1H, d, J=13 Hz), 4.33(1H, d, J=13 Hz), 4.77(2H, s), 4.93(2H, s), 4.96(1H, d, J=5 Hz), 5.08(2H, s), 5.32(1H, d, J=8 Hz), 5.65(1H, dd, J=8 Hz, 5 Hz), 6.7-7.0(6H, m), 7.05-7.4(6H, m).

(b) Trifluoroacetic acid salt of 7β-[D-2-amino-2-(4-carboxymethoxyphenyl)acetamido]-3-(1-methyl-5-tetrazolyl)-thiomethyl-3-cephem-4-carboxylic acid:

The compound obtained in the above procedure (a) (328 mg) was added with stirring at 0° C. to a 2.5:1 liquid mixture of trifluoracetic acid and anisole (4 ml). The resulting mixture was stirred at the same temperature for 5 hours, to which a 3:1 liquid mixture of ethyl ether and hexane (30 ml) was added. The precipitate was collected by filtration and then washed with ethyl ether to obtain the desired product (230 mg).

Infrared absorption spectrum[cm⁻¹, Nujol(trade mark)]: 1750-1780, 1660-1710, 1605.

NMR spectrum(δ, DMSO-d₆): 3.44(1H, d, J=18 Hz), 3.64(1H, d, J=18 Hz), 3.90(3H, s), 4.24(2H, brs.), 4.67(2H, s), 4.95(1H, s), 4.98(1H, d, J=5 Hz), 5.71(1H, m), 6.94(2H, d, J=9 Hz), 7.39(2H, d, J=9 Hz).

(c) 7β-[D-2-(4-carboxymethoxyphenyl)-2-(6,7-dihydroxy-4-oxo-4H-1-benzopyran-3-carboxamido)acetamido]-3-(1-methyl-5-tetrazolyl)thiomethyl-3-cephem-4-carboxylic acid:

The compound obtained in the above procedure (b) (130 mg) was suspended in tetrahydrofuran (5 ml), followed by an addition of N,O-bis(trimethylsilyl)acetamide (198 μl). The resulting mixture was cooled in an ice bath. To the mixture was added with stirring 6,7-dihydroxy-4-oxo-4H-1-benzopyran-3-carbonyl chloride (53 mg) and the mixture was stirred at 0° C. for further 2 hours. Ethyl acetate (100 ml) was added to the liquid reaction mixture, followed by its washing succesively with 0.2N-hydrochloric acid, water and a saturated aqueous solution of sodium chloride. Anhydrous magnesium sulfate was added to the thus-treated reaction mixture to dry the same and the solvent was then evaporated. The residue was dissolved in tetrahydrofuran (5 ml) and the resulting solution was added with stirring to ethyl ether (50 ml). The resulting precipitate was collected by filtration and then dried to obtain the desired product (114 mg).

Infrared absorption spectrum[cm⁻¹, Nujol(trade mark)]: 1760, 1655, 1605.

NMR spectrum(δ, DMSO-d₆): 3.52(1H, d, J=18 Hz), 3.72(1H, d, J=18 Hz), 3.93(3H, s), 4.21(1H, d, J=13 Hz), 4.37(1H, d, J=13 Hz), 4.67(2H, s), 5.02(1H, d, J=5 Hz), 5.65-5.85(2H, m), 6.90(2H, d, J=8 Hz), 6.99(1H, s), 7.37(2H, d, J=8 Hz), 7.43(1H, s), 8.86(1H, s), 8.45(1H, d, J=8 Hz), 10.32(1H, d, J=8 Hz).

EXAMPLE 4

Disodium 7β-[D-2-(4-carboxymethoxyphenyl)-2-(6,7-dihydroxy-4-oxo-4H-1-benzopyran-3-carboxamido)-acetamido]-3-(1-methyl-5-tetrazolyl)thiomethyl-3-cephem-4-carboxylate 7β-[D-2-(4-Carboxymethoxyphenyl)-2-(6,7-dihydroxy-4-oxo-4H-1-benzopyran-3-carboxamido)acetamido]-3-(1-methyl-5-tetrazolyl)thiomethyl-3-cephem-4-carboxylic acid (90 mg) was suspended in methanol (3 ml), followed by an addition with stirring of a 1M-solution of sodium acetate in methanol (256 μl). Methanol (12 ml) was added further and, after removal of the insoluble matter by filtration, the filtrate was concentrated. The residue was washed first with ethanol and then with ethyl ether, and then dried in vacuo to obtain the desired product (88 mg).

Infrared absorption spectrum[cm⁻¹, Nujol(trade mark)]: 1740-1780, 1655, 1605.

NMR spectrum(δ, DMSO-d₆-D₂O): 3.27(1H, d, J=18 Hz), 3.50(1H, d, J=18 Hz), 3.88(3H, s), 4.14(1H, d, J=13 Hz), 4.21(3H, s), 4.32(1H, d, J=13 Hz), 4.83(1H, d, J=5 Hz), 5.64(1H, d, J=5 Hz), 5.69(1H, s), 6.80(2H, d, J=8 Hz), 6.87(1H, s), 7.30(2H, d, J=8 Hz), 7.35(1H, s), 8.77(1H, s).

Solubility(in distilled water at 25° C.): 20% or higher.

EXAMPLE 5

7β-[D-2-(4-Carboxymethoxyphenyl)-2-(6,7-dihydroxy-4-oxo-4H-1-benzopyran-3-carboxamido)acetamido]-3-[5-methyl-2-(1,3,4-thiazolyl)]thiomethyl-3-cephem-4-carboxylic acid (a) 7β-[D-2-[4-(p-Methoxybenzyloxycarbonylmethoxy)phenyl]-2-(p-methoxybenzyloxycarbonylamino)acetamido]-3-[5-methyl-2-(1,3,4-thiadiazolyl)]thiomethyl-3-cephem-4-carboxylic acid:

A mixture of 7β-[D-2-[4-(p-methoxybenzyloxycarbonylmethoxy)phenyl]-2-(p-methoxybenzyloxycarbonylamino)acetamido]-3-acetoxymethyl-3-cephem-4-carboxylic acid (1.528 g), 2-mercapto-5-methyl-1,3,4-thiadiazole (1.32 g) and acetonitrile (60 ml) was heated under reflux for 10 hours and the solvent was thereafter evaporated. The residue was dissolved with heating in acetonitrile (about 15 ml) and then allowed to stand at room temperature. Precipitated crystals were removed by filtration and the filtrate was concentrated. The residue was dissolved in a small amount of tetrahydrofuran and then added with stirring to 10% liquid mixture of tetrahydrofuran and ethyl ether. The resulting precipitate was collected by filtration. It was purified by column chromatography packed with silica gel (100 g). Fractions containing the desired product were collected and the solvent was evaporated. The residue was dissolved in a small amount of tetrahydrofuran and added with stirring to 5% liquid mixture of tetrahydrofuran and ethylether. The resulting precipitate was collected by filtration and then dried in vacuo to obtain the desired product (482 mg).

Infrared absorption spectrum[cm⁻¹, Nujol(trade mark)]: 1780, 1740, 1720, 1680, 1650, 1610.

NMR spectrum(δ, DMSO-D₆): 2.66(3H, s), 3.44(1H, d, J=18 Hz), 3.68(1H, d, J=18 Hz), 3.72(3H, s), 3.73(3H, s), 4.17(1H, d, J=13 Hz), 4.47(1H, d, J=13 Hz), 4.77(2H, s), 4.95(2H, s), 4.98(1H, d, J=5 Hz), 5.09(2H, s), 5.33(1H, d, J=8 Hz), 5.66(1H, dd, J=8 Hz, 5 Hz), 6.75-7.00(6H, m), 7.15-7.45(6H, m), 7.84(1H, d, J=8 Hz), 9.12(1H, d, J=8 Hz).

(b) Trifluoroacetic acid salt of 7β-[D-2-amino-2-(4-carboxymethoxy)phenyl]acetamido-3-[5-methyl-2-(1,3,4-thiadiazolyl)]thiomethyl-3-cephem-4-carboxylic acid:

The compound obtained in the above procedure (a) (350 mg) was added with stirring at 0° C. to a 2.5:1 liquid mixture of trifluoroacetic acid and anisole and the resulting mixture was stirred at the same temperature for 4 hours, to which a 3:1 liquid mixture of ethyl ether and hexane (30 ml) was added. The resulting precipitate was collected by filtration, washed with ethyl ether, and then dried to obtain the desired product (159 mg).

Infrared absorption spectrum[cm⁻¹, Nujol(trade mark)]: 1760-1780, 1660-1690, 1605.

NMR spectrum(δ, DMSO-d$_6$): 2.67(3H, s), 3.43(1H, d, J=18 Hz), 3.68(1H, d, J=18 Hz), 4.19(1H, d, J=13 Hz), 4.47(1H, d, J=13 Hz), 4.69(2H, s), 4.96(1H, br.s), 5.02(1H, d, J=5 Hz), 5.74(1H, dd, J=8 Hz, 5 Hz), 6.96(2H, d, J=8.5 Hz), 7.41(2H, d, J=8.5 Hz), 9.46(1H, d, J=8 Hz).

(c) 7β-[D-2-(4-Carboxymethoxyphenyl)-2-(6,7-dihydroxy-4-oxo-4H-1-benzopyran-3-carboxamido)acetamido]-3-[5-methyl-2-(1,3,4-thiadiazolyl)]-thiomethyl-3-cephem-4-carboxylic acid:

The compound obtained in the above procedure (b) (133 mg) was dissolved in tetrahydrofuran (5 ml) and, after an addition of N,O-bis(trimethylsilyl)acetamide (198 μl), cooled in an ice bath. To the thus-cooled liquid mixture, 6,7-dihydroxy-4-oxo-4H-1-benzopyran-3-carbonyl chloride (53 mg) was added with stirring and the resulting mixture was stirred at 0° C. for 2 hours. The liquid reaction mixture was diluted with ethyl acetate (100 ml) and then washed successively with 0.2N-hydrochloric acid (20 ml), water (20 ml×4) and a saturated aqueous solution of sodium chloride (20 ml). After adding anhydrous magnesium sulfate to the thus-washed solution to dry the same, the solvent was evaporated. The residue was dissolved in tetrahydrofuran (5 ml) and added with stirring to ethyl ether. The resulting precipitate was collected by filtration and dried in vacuo to obtain the desired product (111 mg).

Infrared absorption spectrum[cm$^{-1}$, Nujol(trade mark)]: 1760, 1720, 1655, 1605.

NMR spectrum(δ, DMSO-d$_6$): 2.67(3H, s), 3.46(1H, d, J=18 Hz), 3.70(1H, d, J=18 Hz), 4.18(1H, d, J=13 Hz), 4.50(1H, d, J=13 Hz), 4.65(2H, s), 5.02(1H, d, J=5 Hz), 5.6-5.85(2H, m), 6.89(2H, d, J=8.5 Hz), 6.98(1H, s), 7.35(2H, d, J=8.5 Hz), 7.42(1H, s), 8.94(1H, s), 9.43(1H, d, J=8 Hz), 10.32(1H, d, J=8 Hz).

EXAMPLE 6

Disodium
7β-[D-2-(4-carboxymethoxyphenyl)-2-(6,7-dihydroxy-4-oxo-4H-1-benzopyran-3-carboxamido)-acetamido]-3-[5-methyl-2-(1,3,4-thiadiazolyl)]-thiomethyl-3-cephem-4-carboxylate 7β-[D-2-(4-Carboxymethoxyphenyl)-2-(6,7-dihydroxy-4-oxo-4H-1-benzopyran-3-carboxamido)acetamido]-3-[5-methyl-2-(1,3,4-thiadiazolyl)]-thiomethyl-3-cephem-4-carboxylic acid (90 mg) was stirred in a mixture of methanol (5 ml) and a 1M-solution of sodium acetate in methanol (250 μl) and the insoluble matter was removed by filtration. The filtrate was concentrated and ethanol was added to the residue. The resulting precipitate was collected by filtration, washed with ethyl ehter and then dried to obtain the desired product (85 mg).

Infrared absorption spectrum[cm$^{-1}$, Nujol(trade mark)]: 1760, 1660, 1605.

NMR spectrum(δ, DMSO-d$_6$): 2.66(3H, s), 3.48(1H, d, J=18 Hz), 3.52(1H, d, J=18 Hz), 4.18(1H, d, J=13 Hz), 4.32(2H, br.s), 4.52(1H, d, J=13 Hz), 4.90(1H, d, J=5 Hz), 5.56(1H, dd, J=8 Hz, 5 Hz), 5.86(1H, d, J=8 Hz), 6.72(1H, s), 6.83(2H, d, J=8.5 Hz), 7.25(1H, s), 7.32(2H, d, J=8.5 Hz), 8.73(1H, s), 9.32(1H, d, J=8 Hz), 10.50(1H, d, J=8 Hz).

EXAMPLE 7

7β-[D-2-(4-Carboxymethoxyphenyl)-2-(6,7-dihydroxy-4-oxo-4H-1-benzopyran-3-carboxamido)acetamido]-3-(1-carboxymethyl-5-tetrazolyl)thiomethyl-3-cephem-4-carboxylic acid (a) 7β-[D-2-(4-tert-Butoxycarbonylmethoxyphenyl)-2-(p-methoxybenzyloxycarbonylamino)acetamido]-3-(1-carboxymethyl-5-tetrazolyl)thiomethyl-3-cephem-4-carboxylic acid:

A dimethylformamide solution (45 ml) of D-2-(4-tert-butoxycarbonylmethoxphenyl)-2-(p-methoxybenzyloxycarbonylamino)acetic acid (11.65 g) was stirred at −40° to 45° C., to which ethyl chloroformate (2.57 ml) and N-methylmorpholine (2.97 ml) were successively added dropwise. The resulting mixture was stirred at the same temperature for further 30 minutes to obtain a cloudy solution.

7β-Amino-3-(1-carboxymethyl-5-tetrazolyl)thiomethyl-3-cephem-4-carboxylic acid (10.05 g) was added to a dimethylformamide solution (80 ml) of N-trimethylsilylacetamide (20.20 g) and methanesulfonic acid (0.622 g). The resulting mixture was stirred at room temperature for 30 minutes. The thus-obtained solution was cooled to −40° C. and then added with stirring to the above-prepared cloudy solution. The thus-obtained solution was stirred for 1 hour at −45° to −20° C. After adding methanol (2 ml) to the liquid reaction mixture, 0.5N-hydrochloric acid (300 ml) and ethyl acetate (200 ml) which had been ice-cooled were added and the resulting mixture was stirred. The ethyl acetate layer was separated, while the water layer was extracted further with ethyl acetate. Both ethyl acetate layers were combined together and, after being washed twice with ice water (200 ml in total), dried over anhydrous magnesium sulfate. The resulting solution was concentrated under reduced pressure and the thus-formed residue was purified by silica gel chromatography. The residue was charged using chloroform and the column was eluted successively with a 975:25:2 mixed solvent of chloroform, methanol and formic acid, a 970:30:2 mixed solvent of the same solvents and a 960:40:2 mixed solvent of the same solvents. Fractions containing the desired product were combined together and then concentrated under reduced pressure. The residue was dissolved in tetrahydrofuran (10 ml) and then filtered. The filtrate was added dropwise with stirring to a 1:2 mixture of ethyl ether and petroleum ether (300 ml). The resulting precipitate was collected by filtration, washed with petroleum ether, and then dried under reduced pressure to obtain the desired product as yellowish white powder (6.02 g).

Infrared absorption spectrum[(cm$^{-1}$, Nujol(trade mark)]: 1770, 1700, 1600.

NMR spectrum(δ, DMSO-d$_6$): 1.40(9H, s), 3.72(3H, s), 4.16(1H, d, J=13 Hz), 4.38(1H, d, J=13 Hz), 4.60(2H, s), 4.93(2H, s), 4.94(1H, d, J=5 Hz), 5.22(2H, s), 5.30(1H, d, J=8 Hz), 5.64(1H, dd, J=8 Hz, 5 Hz), 6.80(2H, d, J=8 Hz), 6.87(2H, d, J=8 Hz), 7.26(2H, d, J=8 Hz), 7.32(2H, d, J=8 Hz), 7.88(1H, d, J=8 Hz), 9.11(1H, d, J=8 Hz).

(b) Trifluoroacetic acid salt of 7β-[D-2-amino-2-(4-carboxymethoxyphenyl)acetamido]-3-(1-carboxymethyl-5-tetrazolyl)thiomethyl-3-cephem-4-carboxylic acid:

The compound obtained in the above procedure (a) (3.8 g) was added with stirring at 0° C. to a 2.5:1 liquid mixture of trifluoroacetic acid and anisole (49 ml), and the resulting mixture was stirred at the same temperature for 4.5 hours. Added to the resulting mixture was a 1:1 mixture of ethyl ether and petroleum ether (250 ml). The resulting precipitate was collected by filtration and washed with ethyl ether to obtain the desired product (2.668 g)

Infrared absorption spectrum[cm$^{-1}$, Nujol(trade mark)]: 1770, 1680, 1605.

NMR spectrum($\delta$, DMSO-d$_6$): 4.21(2H, brs.), 4.65(2H, s), 4.8–5.2(4H, m), 5.69(1H, dd, J=8 Hz, 5 Hz), 6.92(2H, d, J=8.5 Hz), 7.36(2H, d, J=8.5 Hz), 9.45(1H, d, J=8 Hz).

(c) 7$\beta$-[D-2-(4-Carboxymethoxyphenyl)-2-(6,7-dihydroxy-4-oxo-4H-1-benzopyran-3-carboxamido)acetamido]-3-(1-carboxymethyl-5-tetrazolyl)thiomethyl-3-cephem-4-carboxylic acid:

The compound obtained in the above procedure (b) (110 mg) was suspended in tetrahydrofuran (5 ml). N,O-Bis(trimethylsilyl)acetamide (197 $\mu$l) was added to the resulting suspension, followed by cooling the resulting mixture in an ice bath. Then, 6,7-dihydroxy-4-oxo-4H-1-benzopyran-3-carbonyl chloride (42.1 mg) was added with stirring to the mixture and the resulting mixture was stirred at 0° C. for 2 hours. The liquid reaction mixture was added to ethyl acetate (150 ml) and then washed successively with 0.2N-hydrochloric acid (50 ml), water (40 ml×4) and a saturated aqueous solution of sodium chloride (40 ml). After drying the organic layer over anhydrous magnesium sulfate, the solvent was evaporated. The residue was dissolved in a small amount of tetrahydrofuran and the resulting solution was added with stirring to ethyl ether. The precipitate was collected by filtration to obtain the desired product (100 mg).

Infrared absorption spectrum[cm$^{-1}$, Nujol(trade mark)]: 1760, 1730, 1655, 1605.

NMR spectrum($\delta$, DMSO-d$_6$): 4.18(1H, d, J=13 Hz), 4.44(1H, d, J=13 Hz), 4.64(2H, s), 4.97(1H, d, J=5 Hz), 5.28(2H, s), 5.6–5.8(2H, m), 6.87(2H, d, J=8.5 Hz), 6.94(1H, s), 7.33(2H, d, J=8.5 Hz), 7.40(1H, s), 8.81(1H, s), 9.40(1H, d, J=8 Hz), 10.29(1H, d, J=8 Hz).

EXAMPLE 8

Trisodium 7$\beta$-[D-2-(4-carboxymethoxyphenyl)-2-(6,7-dihydroxy-4-oxo-4H-1-benzopyran-3-carboxamido)-acetamido]-3-(1-carboxymethyl-5-tetrazolyl)thiomethyl-3-cephem-4-carboxylate 7$\beta$-[D-2-(4-carboxymethoxyphenyl)-2-(6,7-dihydroxy-4-oxo-4H-1-benzopyran-3-carboxamido)acetamido]-3-(1-carboxymethyl-5-tetrazolyl)thiomethyl-3-cephem-4-carboxylic acid (90 mg) was dissolved in a liquid mixture of methanol (2 ml) and dimethylformamide (0.3 ml), followed by an addition of a 1M-solution of sodium acetate in methanol (460 $\mu$l). After converting the resulting mixture to a clear solution by an addition of dimethylformamide (0.3 ml), methanol was evaporated. Ethyl ether was added to the residue and the resulting precipitate (95 mg) was collected by filtration. An 88 mg portion of the precipitate was separated and dissolved in methanol (6 ml). After an addition of acetic acid (5.3 $\mu$l), the solvent was evaporated and the residue was washed first with ethanol and then with ethyl ether to obtain the desired product (80 mg).

Infrared absorption spectrum[cm$^{-1}$, Nujol(trade mark)]: 1730–1770, 1680, 1670, 1630–1660.

NMR spectrum($\delta$, DMSO-d$_6$): 4.10(1H, d, J=13 Hz), 4.22(2H, s), 4.33(1H, d, J=13 Hz), 4.57(2H, s), 4.86(1H, d, J=5 Hz), 5.51(1H, dd, J=8 Hz, 5 Hz), 5.71(1H, d, J=8 Hz), 6.32(1H, s), 6.80(2H, d, J=8.5 Hz), 7.07(1H, s), 7.29(2H, d, J=8.5 Hz), 8.59(1H, s).

Solubility(in distrilled water at 25° C.): 30% or higher.

EXAMPLE 9

7$\beta$-[D-2-(4-Carboxymethoxyphenyl)-2-(7,8-dihydroxy-4-oxo-4H-1-benzopyran-3-carboxamido)acetamido]-3-(1-methyl-5-tetrazolyl)thiomethyl-3-cephem-4-carboxylic acid Thionyl chloride (10 ml) was added to 7,8-dihydroxy-4-oxo-4H-1-benzopyran-3-carboxylic acid (22.2 mg) and the resulting mixture was refluxed for 3 hours. Thionyl chloride was then evaporated. Benzene (5 ml) was added to the residue and the solvent was evaporated again. The thus-formed residue was dried under reduced pressure to obtain the acid chloride.

Trifluoroacetic acid salt of 7$\beta$-[D-2-amino-2-(4-carboxymethoxyphenyl)acetamido]-3-(1-methyl-5-tetrazolyl)thiomethyl-3-cephem-4-carboxylic acid (65 mg) was suspended in tetrahydrofuran (3 ml). After adding N,O-bis(trimethylsilyl)acetamide (99 $\mu$l) to the suspension, the resulting mixture was ice-cooled. To the mixture, the entire portion of the above acid chloride was added together with tetrahydrofuran (2 ml). The resulting mixture was stirred with ice-cooling for 2 hours. After adding ethyl acetate (100 ml) to the liquid reaction mixture, the resulting mixture was washed successively with 0.5N-hydrochloric acid (20 ml), water (20 ml×4) and a saturated aqueous solution of sodium chloride (20 ml). After drying the liquid reaction mixture by an addition of anhydrous magnesium sulfate, the solvent was evaporated. The residue was dissolved in tetrahydrofuran (2.5 ml) and the thus-formed solution was added with stirring to ethyl ether (25 ml). The resulting precipitate was collected by filtration and then dried to obtain the desired product (50 mg).

Infrared absorption spectrum[cm$^{-1}$, Nujol(trade mark)]: 1750–1785, 1720, 1660, 1610.

NMR spectrum($\delta$, DMSO-d$_6$): 3.52(1H, d, J=18 Hz), 3.72(1H, d, J=18 Hz), 3.94(3H, s), 4.20(1H, d, J=13 Hz), 4.37(1H, d, J=13 Hz), 4.67(2H, s), 5.02(1H, d, J=4.5 Hz), 5.65–5.85(2H, m), 6.91(2H, d, J=8.5 Hz), 7.07(1H, d, J=8.5 Hz), 7.39(2H, d, J=8.5 Hz), 7.57(1H, d, J=8.5 Hz), 8.92(1H, s).

EXAMPLE 10

7$\beta$-[D-2-(4-Carboxymethoxyphenyl)-2-(7,8-dihydroxyphenyl)-2-(7,8-dihydroxy-2-oxo-2H-1-benzopyran-3-carboxamido)acetamido]-3-(1-methyl-5-tetrazolyl)-thiomethyl-3-cephem-4-carboxylic acid Similarly to Example 9, 7,8-dihydroxy-2-oxo-2H-1-benzopyran-3-carboxylic acid (22.2 mg) was converted to the acid chloride by thionyl chloride. The entire portion of this acid chloride and trifluoroacetic acid salt of 7$\beta$-[D-2-amino-2-(4-carboxymethoxyphenyl)acetamido]-3-(1-methyl-5-tetrazolyl)-thiomethyl-3-cephem-4-carboxylate (65 mg) were reacted with each other to obtain the desired product (38 mg).

Infrared absorption spectrum[cm$^{-1}$, Nujol(trade mark)]: 1760–1780, 1705, 1665, 1620, 1605

NMR spectrum($\delta$, DMSO-d$_6$): 3.52(1H, d, J=18 Hz), 3.72(1H, d, J=18 Hz), 3.94(3H, s), 4.21(1H, d, J=13 Hz), 4.38(1H, d, J=13 Hz), 4.67(2H, s), 5.03(1H, d, J=4.5 Hz), 5.65–5.85(2H, m), 6.91(3H, d, J=8.5 Hz), 7.34(1H, d, J=8.5 Hz), 7.36(2H, d, J=8.5 Hz), 8.76(1H, s).

EXAMPLE 11

7β-[D-2-(4-Carboxymethoxyphenyl)-2-(6,7-diacetoxy-1,4-dihydro-1-ethyl-4-oxoquinolin-3-carboxamidoacetamido]-3-(1-methyl-5-tetrazolyl)thiomethyl-3-cephem-4-carboxylic acid After stirring trifluoroacetic acid salt of 7β-[D-2-amino-2-(4-carboxymethoxyphenyl)acetamido]-3-(1-methyl-5-tetrazolyl)-thiomethyl-3-cephem-4-carboxylic acid (93 mg), N,O-bis(trimethylsilyl)acetamide (150 μl) and ethyl acetate (20 ml) for 20 minutes, 6,7-diacetoxy-1,4-dihydro-1-ethyl-4-oxoquinolin-3-carbonyl chloride (52 mg) was added. After stirring the resulting mixture for 1 hour, the liquid reaction mixture was washed successively with 1N-hydrochloric acid (20 ml), water (20 ml), and a saturated aqueous solution of sodium chloride (20 ml). It was then dried over anhydrous magnesium sulfate, and the solvent was evaporated. The residue was thereafter solidified by an addition of ethyl alcohol and then collected by filtration to obtain th desired product (72 mg).

Infrared absorption spectrum[cm$^{-1}$, Nujol(trade mark)]: 1760, 1640, 1600.

NMR spectrum(δ, DMSO-d$_6$): 1.35(3H, t, J=7 Hz), 2.32(3H, s), 2.35(3H, s), 3.89(3H, s), 4.60(2H, s), 4.96(1H, d, J=5 Hz), 5.79(1H, dd, J=10 Hz, 5 Hz), 6.83(2H, d, J=8 Hz), 7.32(2H, d, J=8 Hz), 7.88(1H, s), 8.12(1H, s), 8.79(1H, s).

EXAMPLE 12

7β-[D-2-(4-Carboxymethoxyphenyl)-2-(6,7-dihydroxy-1,4-dihydro-1-ethyl-4-oxoquinolin-3-carboxamido)-acetamido]-3-(1-methyl-5-tetrazolyl)thiomethyl-3-cephem-4-carboxylic acid 7β-[D-2-(4-Carboxymethoxyphenyl)-2-(6,7-diacetoxy-1,4-dihydro-1-ethyl-4-oxoquinolin-3-carboxamido)acetamido]-3-(1-methyl-5-tetrazolyl)thiomethyl-3-cephem-4-carboxylic acid (37 mg), sodium hydrogencarbonate (20 mg), ethanol (2 ml) and water (2 ml) were stirred at 50° C. for 2 and a half hours. After making the liquid reaction mixture acidic with dilute hydrochloric acid, the resulting mixture was extracted by adding ethyl acetate (20 ml). The ethyl acetate solution was washed with water and then dried over anhydrous magnesium sulfate. The solution was concentrated under reduced pressure. A mixed solvent of ethyl ether and hexane was added to the residue and the resulting precipitate was collected by filtration to obtain the desired product (9 mg).

Infrared absorption spectrum[cm$^{-1}$, Nujol(trade mark)]: 1760, 1640, 1600.

NMR spectrum(δ, DMSO-d$_6$): 1.38(3H, t, J=8 Hz), 3.97(3H, s), 4.68(2H, s), 5.03(1H, d, J=5 Hz), 5.60–5.92(1H, m), 6.92(2H, d, J=8 Hz), 7.12(1H, s), 7.40(2H, d, J=8 Hz), 7.67(1H, s), 8.63(1H, s).

EXAMPLE 13

7β-[D-2-(4-Carboxymethoxyphenyl)-2-(6,7-dihydroxy-4-oxo-4H-1-benzopyran-3-carboxamido)acetamido]-3-[1-(2-N,N-dimethylaminoethyl)-5-tetrazolyl]thiomethyl-3-cephem-4-carboxylic acid 7β-[D-2-(6,7-Dihydroxy-4-oxo-4H-1-benzopyran-3-carboxamido]-3-acetoxymethyl-4-carboxylic acid (293 mg).

1-(2-N,N-dimethylaminoethyl)-5-mercaptotetrazole (277 mg) and sodium hydrogencarbonate (34 mg) were dissolved in a phosphate buffer (pH 6.4; 10 ml). The resulting solution was agitated at 65° C. for 6 hours. The liquid reaction mixture was ice-cooled and its pH was adjusted to 2.0 by an addition of 1N-hydrochloric acid.

The resulting precipitate was collected by filtration, washed with water, and then dried to obtain the desired product (185 mg).

NMR spectrum(δ, DMSO-d$_6$-D$_2$O): 2.18(3H, s), 3.00(2H, m), 4.24(2H, m), 4.63(2H, m), 4.93(1H, d, J=4.5 Hz), 5.64(1H, d, J=4.5 Hz), 5.66(1H, s), 6.77(2H, d, J=8 Hz), 6.98(1H, s), 7.35(2H, d, J=8 Hz), 7.42(1H, s), 8.82(1H, s).

EXAMPLE 14

Disodium 7β-[D-2-(4-carboxymethoxyphenyl)-2-(6,7-dihydroxy-4-oxo-4H-1-benzopyran-3-carboxamido)-acetamido]-3-[1-(2-N,N-dimethylaminoethyl)-5-tetrazolyl]-thiomethyl-3-cephem-4-carboxylate 7β-[D-2-(4-Carboxymethoxyphenyl)-2-(6,7-dihydroxy-4-oxo-4H-1-benzopyran-3-carboxamido)acetamido]-3-[1-(2-N,N-dimethylaminoethyl)-5-tetrazolyl]thiomethyl-3-cephem-4-carboxylic acid (168 mg) was dissolved in water (1.6 ml), followed by an addition of sodium acetate (45 mg). After ice-cooling, ethanol (4.8 ml) was added dropwise and the resulting precipitate was collected by filtration. The precipitate was washed with ethyl ether and then dried to obtain the desired product (117 mg).

Infrared absorption spectrum[cm$^{-1}$, Nujol(trade mark)]: 1760, 1660, 1605.

NMR spectrum(δ, DMSO-d$_6$-D$_2$O): 2.18(6H, s), 2.76(2H, m), 3.40(2H, m), 4.34(4H, m), 4.82(1H, d, J=4.5 Hz), 5.52(1H, d, J=4.5 Hz), 5.70(1H, s), 6.80(2H, d, J=8 Hz), 6.90(1H, s), 7.30(2H, d, J=8 Hz), 7.36(1H, s), 8.76(1H, s).

EXAMPLE 15

Trisodium 7β-[D-2-(4-carboxymethoxyphenyl)-2-(6,7-dihydroxy-2-methyl-4-oxo-4H-1-benzopyran-3-carboxamido)acetamido]-3-(1-carboxymethyl-5-tetrazolyl)thiomethyl-3-cephem-4-carboxylate (a) 6,7-Dihydroxy-2-methyl-4-oxo-4H-1-benzopyran-3-carbonyl chlorode:

A mixture of 6,7-dihydroxy-2-methyl-4-oxo-4H-1-benzopyran-3-carboxylic acid (150 mg), thionyl chloride (2.5 ml) and dimethylformamide (one droplet) was refluxed for 1 hour. The liquid reaction mixture was concentrated under reduced pressure to obtain the desired product.

(b) Trisodium 7β-[D-2-(4-carboxymethoxyphenyl)-2-(6,7-dihydroxy-2-methyl-4-oxo-4H-1-benzopyran-3-carboxamido)-acetamido]-3-(1-carboxymethyl-5-tetrazolyl)thiomethyl-3-cephem-4-carboxylate:

Trifluoroacetic acid salt of 7β-[D-2-amino-2-(4-carboxymethoxyphenyl)acetamido]-3-(1-carboxymethyl-5-tetrazolyl)thiomethyl-3-cephem-4-carboxylic acid (0.416 g) was added to a mixture of ethyl acetate (25 ml), N,N-dimethylacetamide (0.4 ml) and N-trimethylsilylacetamide (0.6 g). The resulting mixture was stirred at room temperature for 10 minutes. The thus-obtained solution was ice-cooled, to which the entire portion of the acid chloride obtained in the above procedure (a) was added with stirring as an ethyl acetate solution (1 ml). The resulting mixture was stirred at the same temperature for 30 minutes and an aqueous solution (1.8 ml) of sodium acetate (147 mg) was added to the liquid reaction mixture to extract the same. The water layer was separated, to which ethanol (10 ml) was added. The resulting precipitate was collected by filtration and, after washing it successively with ethanol and ethyl ether, dried to obtain the desired product (106 mg).

Infrared absorption spectrum[$cm^{-1}$, Nujol(trade mark)]: 1750, 1650, 1600.

NMR spectrum($\delta$, DMSO-$d_6$-$D_2O$): 2.60(3H, s), 3.44(2H, m), 4.20(4H, m), 4.63(2H, m), 4.87(1H, d, J=5 Hz), 5.58(2H, m), 6.65(1H, s), 6.85(2H, d, J=8 Hz), 7.09(1H, s), 7.34(2H, d, J=8 Hz).

Solubility(in distilled water at 25° C.): 30% or higher.

EXAMPLE 16

7β-[D-2-(4-carboxymethoxyphenyl)-2-(7,8-diacetoxy-4-oxo-4H-1-benzopyran-3-carboxamido)acetamido]-3-(1-carboxymethyl-5-tetrazolyl)thiomethyl-3-cephem-4-carboxylic acid An ethyl acetate solution (1 ml) of N-trimethylsilylacetamide (1.88 g) was added with stirring to a mixture of trifluoroacetic acid salt of 7β-[D-2-amino-2-(4-carboxymethoxyphenyl)-acetamido]-3-(1-carboxymethyl-5-tetrazolyl)thiomethyl-3-cephem-4-carboxylic acid (0.988 g), ethyl acetate (30 ml) and N,N-dimethylacetamide (1.5 ml), at room temperature. The resulting mixture was stirred at the same temperature for further 30 minutes. The thus-obtained solution was ice-cooled, followed by an addition with stirring of 6,7-diacetoxy-4-oxo-4H-1-benzopyran-3-carbonyl chloride (0.464 g). The resulting mixture was agitated at the same temperature for 30 minutes. To the liquid reaction mixture, were added 1N-hydrochloric acid (10 ml), ethyl acetate (40 ml) and ethanol (10 ml). The resulting mixture was stirred and then separated into aqueous and organic layers. The organic layer was washed three times with water (30 ml in total) and then dried over anhydrous magnesium sulfate. The solvent was evaporated and ethyl ether was added to the residue to solidify the same. The resulting solid was collected by filtration and, after being washed with ethyl ether, dried to obtain the desired product (1.059 g).

Infrared absorption spectrum[$cm^{-1}$, Nujol(trade mark)]: 1780, 1730, 1660, 1605.

NMR spectrum($\delta$, DMSO-$d_6$-$D_2O$): 2.36(3H, s), 2.42(3H, s), 3.60(2H, m), 4.18(1H, d, J=13 Hz), 4.36 (1H, d, J=13 Hz), 4.64(2H, s), 4.96(1H, d, J=5 Hz), 5.20(2H, s), 5.69(1H, d, J=5 Hz), 5.71(1H, s), 6.88(2H, d, J=8 Hz), 7.36(2H, d, J=8 Hz), 7.53 (1H, d, J=9 Hz), 8.12(1H, d, J=9 Hz), 8.93(1H, s).

EXAMPLE 17

7β-[D-2-(4-Carboxymethoxyphenyl)-2-(7,8-diacetoxy-4-oxo-4H-1-benzopyran-3-carboxamido)acetamido]-3-acetoxymethyl-3-cephem-4-carboxylic acid An ethyl acetate solution (5 ml) of N-trimethylsilylacetamide (8.0 g) was added with stirring at room temperature to a mixture of trifluoroacetic acid salt of 7β-[D-2-amino-2-(4-carboxymethoxyphenyl)acetamido]-3-acetoxymethyl-3-cephem-4-carboxylic acid (6.12 g), ethyl acetate (200 ml) and N,N-dimethylacetamide (10 ml). The thus-obtained solution was cooled to 10° C., to which 6,7-diacetoxy-4-oxo-4H-1-benzopyran-3-carbonyl chloride (3.25 g) was added with stirring. After stirring the resulting mixture at the same temperature for 30 minutes, 0.5N-hydrochloric acid (40 ml), ethyl acetate (200 ml) and methanol (20 ml) were added and the resulting mixture was stirred. The organic layer was separated and washed three times with a 5:1 liquid mixture of water and methanol (120 ml in total), followed by an addition of anhydrous magnesium sulfate to dry the solution. The solvent was evaporated and methanol was added to the residue to solidify the same. The resulting solid was collected by filtration. The solvent was evaporated from the mother liquor and methanol was added to the residue to solidify the same. The thus-formed solid was also collected by filtration. Both of the thus-collected solids were combined together and, after successively washed with methanol and ethyl ether, dried to obtain the desired product (5.00 g).

Infrared absorption spectrum[$cm^{-1}$, Nujol(trade mark)]: 1780, 1730, 1660, 1610.

NMR spectrum($\delta$, DMSO-$d_6$-$D_2O$): 2.00(3H, s), 2.36(3H, s), 2.41 (3H, s), 3.44(2Hk m) 4.64(2H, s), 4.67(1H, d, J=13 Hz), 4.92(1H, d, J=13 Hz), 4.99(1H, d, J=5 Hz), 5.70 (1H, d, J=5 Hz), 5.72(1H, s), 6.84(2H, d, J=8 Hz), 7.36(2H, d, J=8 Hz), 7.53(1H, d, J=9 Hz), A8.13(1H, d, J=9 Hz), 8.94(1H, s).

EXAMPLE 18

7β-[D-2-(4-Carboxymethoxyphenyl)-2-(7,8-dihydroxy-4-oxo-4H-1-benzopyran-3-carboxamido)acetamido]-3-acetoxymethyl-3-cephem-4-carboxylic acid To a liquid mixture of a 0.5N aqueous solution of sodium hydrogencarbonate (52 ml) and ethanol (22 ml), was added with stirring at room temperature 7β-[D-2-(4-carboxymethoxyphenyl)-2-(7,8-diacetoxy-4-oxo-4H-1-benzopyran-3-carboxamido)acetamido]-3-acetoxymethyl-3-cephem-4-carboxylic acid (5.00 g). The thus-obtained solution was heated to 45° C. and stirred for 30 minutes. The liquid reaction mixture was ice-cooled, to which 1N-hydrochloric acid was added with stirring to adjust its pH to 2.0. The resulting precipitate was collected by filtration, washed with water and then dried to obtain the desired product (4.21 g).

Infrared absorption spectrum[$cm^{-1}$, Nujol(trade mark)]: 1760, 1710, 1660, 1605.

NMR spectrum($\delta$, DMSO-$d_6$-$D_2O$): 2.01(3H, s), 3.46(2H, m), 4.64(2H, s), 4.66(1H, d, J=13 Hz), 4.92(1H, d, J=13 Hz), 4.99(1H, d, J=5 Hz), 5.70(1H, d, J=5 Hz), 5.72(1H, s), 6.88(2H, d, J=8 Hz), 7.04(1H, d, J=8 Hz), 7.36(2H, d, J=8 Hz), 7.54(1H, d, J=8 Hz), 8.88(1H, s).

EXAMPLE 19

Disodium
7β-[D-2-(4-carboxymethoxyphenyl)-2-(7,8-dihydroxy-4-oxo-4H-1-benzopyran-3-carboxamido)-acetamido]-3-acetoxymethyl-3-cephem-4-carboxylate 7β-[D-2-(4-Carboxymethoxyphenyl)-2-(7,8-dihydroxy-4-oxo-4H-1-benzopyran-3-carboxamido)acetamido]-3-acetoxymethyl-3-cephem-4-carboxylic acid (4.020 g) was dissolved in a 6:1 mixed solvent of ethyl acetate and ethanol (700 ml), followed by an addition of an aqueous solution of sodium acetate (1 g) in water (100 ml). The water layer was separated, to which ethanol (400 ml) was added with stirring. The resulting solution was ice-cooled. The resulting precipitate was collected by filtration and, after washing the precipitate successively with ethanol and ethyl ether, dried to obtain the desired product (2.0 g).

Infrared spectrum[cm$^{-1}$, Nujol(trade mark)]: 1755, 1650, 1600.

NMR spectrum($\delta$, DMSO-d$_6$-D$_2$O): 1.97(3H, s), 3.34(2H, m), 4.18(2H, s), 4.72(1H, d, J=13 Hz), 4.86(1H, d, J=5 Hz), 4.92(1H, d, J=13 Hz), 5.53(1H, d, J=5 Hz), 5.78(1H, s), 6.76(2H, d, J=9 Hz), 6.92(1H, d, J=9 Hz), 7.27(2H, d, J=9 Hz), 7.44(1H, d, J=9 Hz), 8.80(1H, s).

EXAMPLE 20

Trisodium
7β-[D-2-(4-carboxymethoxyphenyl)-2-(7,8-dihydroxy-4-oxo-4H-1-benzopyran-3-carboxamido)-acetamido]-3-(1-carboxymethyl-5-tetrazolyl)thiomethyl-3-cephem-4-carboxylate 7β-[D-2-(4-Carboxymethoxyphenyl)-2-(7,8-diacetoxy-4-oxo-4H-1-benzopyran-3-carboxamido)acetamido]-3-(1-carboxymethyl-5-tetrazolyl)thiomethyl-3-cephem-4-carboxylic acid (1.041 g) was added with stirring at room temperature to a liquid mixture of ethanol (4 ml) and a 0.5N aqueous sodium hydrogencarbonate solution (12 ml). The resulting solution was heated to 45° C. and stirred for 30 minutes. After cooling the liquid reaction mixture with ice and adding ethyl acetate (25 ml) thereto, 1N-hydrochloric acid was added to adjust is pH to 2.0. The organic layer was separated and then washed successively twice with a 10:1 mixture of water and ethanol (21 ml, in total), twice with water (20 ml in total) and once with a 10:1 mixture of water and ethanol (11 ml in total). An aqueous solution of sodium acetate (295 mg) in water (10 ml) was then added to the thus-washed organic layer and the water layer was separated. Isopropanol (10 ml) and ethanol (30 ml) were thereafter added with stirring to the water layer and the resulting mixture was ice-cooled. The resulting precipitate was collected by filtration and, after washing it successively with ethanol and ethyl ether, dried to obtain the desired product (0.540 g).

Infrared absorption spectrum[cm$^{-1}$, Nujol(trade mark)]: 1755, 1650, 1600.

NMR spectrum($\delta$, DMSO-d$_6$-D$_2$O): 3.44(2H, m), 4.16(1H, d, J=13 Hz), 4.17(2H, s), 4.28(1H, d, J=13 Hz), 4.60(2H, s), 4.86(1H, d, J=4.5 Hz), 5.54(1H, d, J=4.5 Hz), 5.72(1H, s), 6.81(2H, d, J=9 Hz), 6.95(1H, d, J=9 Hz), 7.30(2H, d, J=9 Hz), 7.48(1H, d, J=9 Hz), 8.84(1H, s).

EXAMPLE 21

7β-[D-2-(4-Carboxymethoxyphenyl)-2(6,7-diacetoxy-2-methyl-4-oxo-4H-1-benzopyran-3-carboxamido)-acetamido[-7α-methoxy-3-(1-carboxymethyl-5-tetrazolyl)-thiomethyl-3-cephem-4-carboxylic acid (a) 6,7-Diacetoxy-2-methyl-4-oxo-4H-1-benzopyran-3-carboxylic acid:

A mixture of 6,7-dihydroxy-2-methyl-4-oxo-4H-1-benzopyran-3-carboxylic acid (2.24 g), dimethylformamide (30 ml), ethyl acetate (10 ml), pyridine (2.3 ml) and acetic anhydride (2.3 ml) was stirred at room temperature for 3 hours. Ethyl acetate (100 ml) was added to the liquid reaction mixture. After washing the resulting mixture with 6N-hydrochloric acid and water, anhydrous magnesium sulfate was added to dry the mixture. The solvent was evaporated and ethyl ether was added to the residue to solidify the same. The solid was collected by filtration and, after being washed with a 1:1 mixture of ethyl acetate and ether, dried under reduced pressure to obtain the desired product as white crystals (1.93 g).

Infrared absorption spectrum[cm$^{-1}$, Nujol(trade mark)]: 1780, 1750, 1720, 1605.

(b) 6,7-Diacetoxy-2-methyl-4-oxo-4H-1-benzopyran-3-carbonyl chloride:

A mixture of 6,7-diacetoxy-2-methyl-4-oxo-4H-1-benzopyran-3-carboxylic acid obtained in the above procedure (a) (1.0 g), dimethylformamide (0.04 ml), thionyl chloride (0.54 ml) and benzene (100 ml) was refluxed for 1 hour. The liquid reaction mixture was concentrated under reduced pressure and n-hexane was added to the residue to solidify the same. The solid was collected by filtration and dried under reduced pressure to obtain the desired product (1.0 g).

Infrared absorption spectrum[cm$^{-1}$, Nujol(trade mark)]: 1770, 1650, 1620.

(c) 7β-[D-2-(4-tert-Butoxycarbonylmethoxyphenyl)-2-(p-methoxybenzyloxycarbonylamino)acetamido]-7α-methoxy-3-(1-carboxymethyl-5-tertrazolyl)thiomethyl-3-cephem-4-carboxylic acid:

Lithium methoxide (1.14 g) was added to methanol (24 ml). The resulting mixture was stirred at room temperature to dissolve the former. Then, a 1:1 mixture of tetrahydrofuran and dimethylformamide (90 ml) was added and the resulting mixture was cooled to $-55°$ C., to which a solution of the compound obtained in the procedure (a) in Example 7 (4.71 g) in a 1:1 mixture of tetrahydrofuran and dimethylformamide (24 ml) was added dropwise with stirring. Two minutes later, tert.-butyl hypochlorite (0.93 ml) was added dropwise and the resulting mixture was stirred at the same temperature for 15 minutes, followed by an addition of acetic acid (0.3 ml). The thus-formed solution was then diluted with ethyl acetate (600 ml) and washed with 0.5N-hydrochloric acid (300 ml). The water layer was extracted with ethyl acetate (300 ml) and the resulting ethyl acetate layer was combined with the above-obtained ethyl acetate layer. It was then washed with water and a saturated aqueous solution of sodium chloride, and then dried over anhydrous magnesium sulfate. The solvent was evaporated and the residue was dissolved in chloroform (36 ml). The thus-formed solutioon was then added dropwise to a 1:1 mixture of n-hexane and ethyl ether (600 ml). The resulting precipitate was collected by filtration, washed with a 1:1 mixture of n-hexane and ethyl ether, and then dried to obtain the desired produce as pale yellowish powder (4.0 g).

Infrared absorption spectrum[cm$^{-1}$, Nujol(trade mark)]: 1770, 1700, 1605.

NMR spectrum($\delta$, DMSO-d$_6$): 1.39(3H, s), 3.30(3H, s), 3.70(3H, s), 4.21(1H, d, J=13 Hz), 4.43(1H, d, J=13 Hz), 4.58(2H, s), 4.92(2H, s), 4.96(1H, s), 5.19(2H, s), 5.29(1H, d, J=8 Hz), 6.78(2H, d, J=8 Hz), 6.85(2H, d, J=8 Hz), 7.24(2H, d, J=8 Hz), 7.33(2H, d, J=8 Hz), 7.75(1H, d, J=8 Hz), 9.39(1H, s).

(d) Trifluoroacetic acid salt of 7$\beta$-[D-2-(4-carboxymethoxyphenyl)-acetamido]-7$\alpha$-methoxy-3-(1-carboxymethyl-5-tetrazolyl)thiomethyl-3-cephem-4-carboxylic acid:

A 1:1 mixture of trifluoroacetic acid and anisole (45.5 ml) was ice-cooled, to which the compound obtained in the above procedure (c) (3.5 g) was added with stirring. The resulting mixture was stirred at same temperature for further 3 hours. The liquid reaction mixture was added with stirring to a 1:1 mixture of petroleum ether and ethyl ether (250 ml). The resulting precipitate was collected by filtration, washed with a 1:1 mixture of petroleum ether and ethyl ether, and then dried to obtain the desired product as powder (2.95 g).

Infrared absorption spectrum[cm$^{-1}$, Nujol(trade mark)]: 1760, 1700, 1660, 1600.

NMR spectrum($\delta$, DMSO-d$_6$): 3.40(3H, s), 4.10(1H, d, J=13 Hz), 4.36(1H, d, J=13 Hz), 4.66(2H, s), 4.96(1H, s), 5.06(1H, s), 5.13(2H, s), 6.93(2H, d, J=8 Hz), 7.41(2H, d, J=8 Hz).

(e) 7$\beta$-[D-2-(4-Carboxymethoxyphenyl)-2-(6,7-diacetoxy-2-methyl-4-oxo-4H-1-benzopyran-3-carboxamido)acetamido]-7$\alpha$-methoxy-3-(1-carboxymethyl-5-tetrazolyl)thiomethyl-3-cephem-4-carboxylic acid:

An ethyl acetate solution (1 ml) of N-trimethylsilylacetamide (1.43 g) was added to a mixture of the compound obtained in the above procedure (d) (1.035 g), ethyl acetate (30 ml) and N,N-dimethylacetamide (1.5 ml). The resulting mixture was stirred for 60 minutes. The thus-obtained solution was cooled to 5° C., followed by an addition of 6,7-diacetoxy-2-methyl-4-oxo-4H-1-benzopyran-3-carbonyl chloride obtained in the above procedure (b) (484 mg). The resulting mixture was stirred at the same temperature for 30 minutes. To the liquid reaction mixture, was added ethyl acetate (30 ml), 1N-hydrochloric acid (30 ml) and methanol (1 ml). After agitating the resulting mixture, it was separated into an ethyl acetate layer and water layer. The ethyl acetate layer was washed successively with 1N-hydrochloric acid and water and then dried over anhydrous magnesium sulfate. The solvent was evaporated and the residue was purified by silica gel column chromatography (eluant: a 960:40:2 mixture of chlorofrom, methanol and formic acid). Eluate fractions, which contained the desired product, were combined and then concentrated under reduced pressure. The residue was taken up in tetrahydrofuran (2 ml), to which ethyl ether was added. The resulting precipitate was collected by filtration, washed with ethyl ether and then dried to obtain the desired product as white powder (294 mg).

Infrared absorption spectrum[cm$^{-1}$, Nujol(trade mark)]: 1760, 1650, 1620.

NMR spectrum($\delta$, DMSO-d$_6$): 2.30(3H, s), 2.32(3H, s), 2.54(3H, s), 3.40(3H, s), 3.56(2H, s), 4.10(1H, d, J=13 Hz), 4.24(1H, d, J=13 Hz), 4.62(2H, s), 4.99(1H, s), 5.20(2H, s), 5.61(1H, d, J=8 Hz), 6.86(2H, d, J=8 Hz), 7.38(2H, d, J=8 Hz), 7.68(1H, s), 7.86(1H, s), 9.36(1H, d, J=8 Hz), 9.58(1H, brs.).

EXAMPLE 22

7$\beta$-[D-2-(4-Carboxymethoxyphenyl)-2-(6,7-diacetoxy-2-methyl-4-oxo-4H-1-benzopyran-3-carboxamido)-acetamido]-3-(1-carboxymethyl-5-tetrazolyl)thiomethyl-3-cephem-4-carboxylic acid An ethyl acetate solution (0.5 ml) of N-trimethylsilylacetamide (0.40 g) was added at room temperature to a mixture of trifluoroacetic acid salt of 7$\beta$-[D-2-amino-2-(4-carboxymethoxyphenyl)acetamido]-3-(1-carboxymethyl-5-tetrazolyl)thiomethyl-3-cephem-4-carboxylic acid (0.277 g), ethyl acetate (10 ml) and N,N-dimethylacetamide (0.4 ml). The resulting mixture was stirred for 60 minutes. The thus-obtained solution was cooled to 5° C., to which 6,7-diacetoxy-2-methyl-4-oxo-4H-1-benzopyran-3-carbonyl chloride (0.135 g) was added with stirring. The resulting mixture was stirred at the same temperature for 30 minutes. Ethyl acetate (10 ml), 1N-hydrochloric acid (15 ml) and methanol (0.5 ml) were added to the liquid reaction mixture, and the resulting mixture was agitated. It was then separated into an ethyl acetate layer and water layer. The ethyl acetate layer was washed successively with 1N-hydrochloric acid and then with water. It was then dried over anhydrous magnesium sulfate. The solution was concentrated. A 2:1 mixture of ethyl acetate and ethyl ether was added to the resulting crystals. The crystals were then collected by filtration. They were washed with a 2:1 mixture of ethyl acetate and ethyl ether and then dried to obtain the desired product as light yellowish crystals (190 mg).

Infrared absorption spectrum[cm$^{-1}$, Nujol(trade mark)]: 1760, 1720, 1650, 1610.

NMR spectrum($\delta$, DMSO-d$_6$): 2.31(3H, s), 2.33(3H, s), 2.56(3H, s), 3.54(2H, m), 4.16(1H, d, J=13 Hz), 4.42(1H, d, J=13 Hz), 4.63(2H, s), 4.96(1H, d, J=5 Hz), 5.27(2H, s), 5.60-5.77(2H, m), 6.85(2H, d, J=8 Hz), 7.36(2H, d, J=8 Hz), 7.69(1H, s), 7.89(1H, s), 9.32(2H, d, J=8 Hz), 9.50(2H, d, J=8 Hz).

EXAMPLE 23

7$\beta$-[D-2-(4-Carboxymethoxyphenyl)-2-(7,8-diacetoxy-2-methyl-4-oxo-4H-1-benzopyran-3-carboxamido)-acetamido]-3-(1-carboxymethyl-5-tetrazolyl)thiomethyl-3-cephem-4-carboxylic acid Trifluoroacetic acid salt of 7$\beta$-[D-2-amino-2-(4-carboxymethoxyphenyl)acetamido]-3-(1-carboxymethyl-5-tetrazolyl)thiomethyl-3-cephem-4-carboxylic acid (0.486 g) and 7,8-diacetoxy-2-methyl-4-oxo-4H-benzopyran-3-carbonyl chloride (0.237 g) were reacted in the same manner as in Example 22 to obtain the desired product (316 mg).

Infrared absorption spectrum[cm$^{-1}$, Nujol(trade mark)]: 1765, 1655, 1635, 1610.

NMR spectrum($\delta$, DMSO-d$_6$): 2.35(3H, s), 2.42(3H, s), 2.53(3H, s), 3.56(2H, m), 4.16(1H, d, J=13 Hz), 4.42(1H, d, J=13 Hz), 4.64(2H, s), 4.95(1H, d, J=5 Hz), 5.28(2H, s), 5.62-5.78(2H, m), 6.85(2H, d, J=8 Hz), 7.28(2H, d, J=8 Hz), 7.31(1H, d, J=9 Hz), 7.97(1H, d, J=9 Hz), 9.30(1H, d, J=8 Hz), 9.44(1H, d, J=8 Hz).

EXAMPLE 24

7β-[D-2-(4-Carboxymethoxyphenyl)-2-(7,8-diacetoxy-2-methyl-4-oxo-4H-1-benzopyran-3-carboxamido)-acetamido]-7α-methoxy-3-(1-carboxymethyl-4-tetrazolyl)thiomethyl-3-cephem-4-carboxylic acid Trifluoroacetic acid salt of 7β-[D-2-amino-2-(4-carboxymethoxyphenyl)acetamido]-7α-methoxy-3-(1-carboxymethyl-5-tetrazolyl)-thiomethyl-3-cephem-4-carboxylic acid (0.506 g) and 7,8-diacetoxy-2-methyl-4-oxo-4H-1-benzopyran-3-carbonyl chloride (0.237 g) were reacted in the same manner as in Example 21 to obtain the desired product (0.143 mg).

Infrared absorption spectrum[cm$^{-1}$, Nujol(trade mark)]: 1760, 1650, 1605.

NMR spectrum(δ, DMSO-d$_6$): 2.34(3H, s), 2.42(3H, s), 2.51(3H, s), 3.52(2H, s), 4.08(1H, d, J=13 Hz), 4.46(1H, d, J=13 Hz), 4.63(2H, s), 4.99(1H, s), 5.24(2H, s), 5.61(1H, d, J=8 Hz), 6.87(2H, d, J=8 Hz), 7.39(4H, d, J=8 Hz), 7.95(1H, d, J=8 Hz), 9.30(1H, d, J=8 Hz), 9.58(1H, brs.).

EXAMPLE 25

Trisodium 7β-[D-2-(4-carboxymethoxyphenyl)-2-(6,7-dihydroxy-2-methyl-4-oxo-4H-1-benzopyran-3-carboxamido]-7α-methoxy-3-(1-carboxymethyl-5-tetrazolyl)thiomethyl-3-cephem-4-carboxylate 7β-[D-2-(4-Carboxymethoxyphenyl)-2-(6,7-diacetoxy-2-methyl-4-oxo-4H-1-benzopyran-3-carboxamido)acetamido]-7α-methoxy-3-(1-carboxymethyl-5-tetrazolyl)thiomethyl-3-cephem-4-carboxylic acid (274 mg) was dissolved in a liquid mixture of a 0.5N aqueous solution of sodium hydrogencarbonate (3 ml) and ethanol (0.7 ml). The resulting solution was stirred at 45° C. for 60 minutes. After ice-cooling the liquid reaction mixture, ethyl acetate (10 ml) was added and the resulting mixture was stirred, followed by an addition of 1N-hydrochloric acid to adjust the pH of the mixture to 2.0. The ethyl acetate layer was separated and, after adding a small amount of ethanol to the ethyl acetate layer, the ethyl acetate layer was washed with water and then filtered. A 0.3N aqueous solution of sodium acetate (3 ml) was added to the filtrate and the resulting mixture was agitated. The water layer was separated, to which ethanol was added with stirring. The resulting precipitate was collected by filtration. It was washed with ethanol and ethyl ether and then dried to obtain the desired product as light yellowish powder (123 mg).

Infrared absorption spectrum[cm$^{-1}$, Nujol(trade mark)]: 1755, 1650, 1610.

NMR spectrum(δ, DMSO-d$_6$-D$_2$O): 2.58(3H, s), 3.40(3H, s), 4.22(4H, s), 4.61(2H, s), 4.87(1H, s), 5.62(1H, s), 6.69(1H, s), 6.82'2H, d, J=8 Hz), 7.18(1H, s), 7.34(2H, d, J=8 Hz).

Solubility(in distilled water at 25° C.): 30% or higher.

EXAMPLE 26

Trisodium 7β-[D-2-(4-carboxymethoxyphenyl)-2-(6,7-dihydroxy-2-methyl-4-oxo-4H-1-benzopyran-3-carboxamido)acetamido]-3-(1-carboxymethyl-5-tetrazolyl)-thiomethyl-3-cephem-4-carboxylate 7β-[D-2-(4-carboxymethoxyphenyl)-2-(6,7-diacetoxy-2-methyl-4-oxo-4H-1-benzopyran-3-carboxamido)acetamido]-3-(1-carboxymethyl-5-tetrazolyl)thiomethyl-3-cephem-4-carboxylic acid (168 mg) was hydrolyzed in the same manner as in Example 25 to obtain the desired product (5 mg).

The infrared absorption spectrum and NMR spectrum of the thus-obtained compound were identical with those of the compound of Example 15.

EXAMPLE 27

Trisodium 7β-[D-2-(4-carboxymethoxyphenyl)-2-(7,8-dihydroxy-2-methyl-4-oxo-4H-1-benzopyran-3-carboxamido)acetamido]-3-(1-carboxymethyl-5-tetrazolyl)-thiomethyl-3-cephem-4-carboxylate 7β-[D-2-(4-Carboxymethoxyphenyl)-2-(7,8-diacetoxy-2-methyl-4-oxo-4H-1-benzopyran-3-carboxamido)acetamido]-3-(1-carboxymethyl-5-tetrazolyl)thiomethyl-3-cephem-4-carboxylic acid (264 mg) was hydrolyzed in the same manner as in Example 25 to obtain the desired product (122 mg).

Infrared absorption spectrum[cm$^{-1}$, Nujol(trade mark)]: 1755, 6145, 1600.

NMR spectrum(δ, DMSO-d$_6$-D$_2$O): 2.62(3H, s), 3.40(2H, m), 4.12(1H, d, J=12 Hz), 4.28(1H, d, J=12 Hz), 4.36(2H, s), 4.62(2H, s), 4.95(1H, d, J=5 Hz), 5.53(1H, d, J=5 Hz), 5.60(1H, s), 6.82(2H, d, J=8 Hz), 6.96(1H, d, J=8 Hz), 7.34(2H, d, J=8 Hz), 7.43(1H, d, J=8 Hz).

EXAMPLE 28

Trisodium 7β-[D-2-(4-carboxymethoxyphenyl)-2-(7,8-dihydroxy-2-methyl-4-oxo-4H-1-benzopyran-3-carboxamido)-acetamido]-7α-methoxy-3-(1-carboxymethyl-5-tetrazolyl)-thiomethyl-3-cephem-4-carboxylate 7β-[D-2-Carboxymethoxyphenyl)-2-(7,8-diacetoxy-2-methyl-4-oxo-4H-1-benzopyran-3-carboxamido)acetamido]-7α-methoxy-3-(1-carboxymethyl-5-tetrazolyl)thiomethyl-3-cephem-4-carboxylic acid (119 mg) was hydrolyzed in the same manner as in Example 25 to obtain the desired product (30 mg).

Infrared absorption spectrum[cm$^{-1}$, Nujol(trade mark)]:
1760, 1650, 1600.

NMR spectrum(δ, DMSO-d$_6$-D$_2$O): 2.95(3H, s), 3.40(3H, s), 4.17(4H, m), 4.60(2H, s), 4.88(1H, s), 5.63(1H, s), 6.80(2H, d, J=8 Hz), 6.87(2H, d, J=8 Hz), 7.34(2H, d, J=8 Hz), 7.35(1H, d, J=8 Hz).

EXAMPLE 29

Disodium 7β-[D-2-(4-carboxymethoxyphenyl)-2-(6,7-dihydroxy-2-methyl-4-oxo-4H-1-benzopyran-3-carboxamido)acetamido]-3-acetoxymethyl-3-cephem-4-carboxylate (a) 7β-[D-2-(4-Carboxymethoxyphenyl)-2-(6,7-diacetoxy-2-methyl-4-oxo-4H-1-benzopyran-3-carboxamido)acetamido]-3-acetoxymethyl-3-cephem-4-carboxylic acid:

Trifluoroacetic acid salt of 7β-[D-2-amino-2-(4-carboxymethoxyphenyl)acetamido]-3-acetoxymethyl-3-cephem-4-carboxylic acid (500 mg) was suspended in tetrahydrofuran (25 ml) and the thus-formed suspension was ice-cooled. After adding N,O-bis(trimethylsilyl)acetamide (1.15 ml) to the suspension and mixing the resulting mixture, 6,7-diacetoxy-2-methyl-4-oxo-4H-1-benzopyran-3-carbonyl chloride (285 mg) was added. The resulting mixture was stirred for 2 hours and 50 minutes with ice-cooling. Ethyl acetate (300 ml) was added to the liquid reaction mixture and the resultant mixture was washed successively with 1N-hydrochloric acid, water and a saturated aqueous solution of sodium chloride, followed by an addition of anhydrous sodium sulfate to dry the solution. The solution was concentrated under reduced pressure, to which ethyl ether (200 ml) was added dropwise. The resulting precipitate was collected by filtration and then dried to obtain the desired product (302 mg).

(b) Disodium 7β-[D-2-(4-carboxymethoxyphenyl)-2-(6,7-dihydroxy-2-methyl-4-oxo-4H-1-benzopyran-3-carboxamido)acetamido]-3-acetoxymethyl-3-cephem-4-carboxylate:

To the compound obtained in the above procedure (a) (100 mg), were added a 0.5N aqueous solution of sodium hydrogen-carbonate (1.02 ml) and ethanol (0.45 ml). The resulting mixture was stirred at 45° C. for 30 minutes. Ethyl acetate (30 ml) and 1N-hydrochloric acid (15 ml) were added to the liquid reaction mixture and the resulting mixture was agitated. The ethyl acetate layer was separated and then washed successively with water, a saturated aqueous solution of sodium chloride and water. Then, an aqueous solution of sodium acetate (21 mg) in water (0.8 ml) was added and the resulting mixture was agitated. The water layer was separated, to which ethanol (7 ml) was added dropwise. The resulting precipitate was collected by filtration and then dried to obtain the desired product (30 mg).

Infrared absorption spectrum[cm$^{-1}$, Nujol(trade mark)]: 1600, 1620, 1650, 1750.

NMR spectrum(δ, DMSO-d$_6$-D$_2$O): 1.99(3H, s), 2.60(3H, s), 3.12(1H, d, J=18 Hz), 3.40(1H, d, J=18 Hz), 4.75(2H, s), 4.82(2H, dd, J=13.5 Hz, 23 Hz), 4.83(1H, d, J=5 Hz), 5.52(1H, d, J=5 Hz), 5.63(1H, s), 6.57(1H, s), 6.77(2H, d, J-8.5 Hz), 7.16(1H, s), 7.30(2H, d, J=8.5 Hz).

EXAMPLE 30

Trisodium 7β-[D-2-(4-carboxymethoxyphenyl)-2-(6,7-dihydroxy-4-oxo-4H-1-benzopyran-3-carboxamido)-acetamido]-7α-methoxy-3-(1-carboxymethyl-5-tetrazolyl)-thiomethyl-3-cephem-4-carboxylate Trifluoroacetic acid salt of 7β-[D-2-amino-2-(4-carboxymethoxyphenyl)acetamido]-7α-methoxy-3-(1-carboxymethyl-5-tetrazolyl)thiomethyl-3-cephem-4-carboxylic acid (191 mg), N,O-bis(trimethylsilyl)acetamide (261 μl) and ethyl acetate (15 ml) were stirred for 20 minutes, followed by an addition of 6,7-dihydroxy-4-oxo-4H-1-benzopyran-3-carbonyl chloride (60 mg). After stirring for 1 hour, 1N-hydrochloric acid (10 ml) was added, followed by an extraction with ethyl acetate. The extract was washed first with water and then with a saturated aqueous solution of sodium chloride, and anhydrous magnesium sulfate was then added to the solution to dry the same. The solvent was evaporated and ethyl ether was added to the residue to solidify the same, and the solid was collected by filtration. It was purified by silica gel column chromatography (solvent: a 80:10:1 mixture of chloroform, methanol and formic acid). Sodium acetate (14 mg) and methanol (2 ml) were added to the thus-obtained solid (40 mg), and the insoluble matter was removed by filtration. The filtrate was concentrated under reduced pressure, followed by an addition of ethanol. The resulting precipitate was collected by filtration, washed with ethyl ether, and then dried to obtain the desired product (50 mg).

Infrared absorption spectrum[cm$^{-1}$, Nujol(trade mark)]: 1760, 1660, 1600.

NMR spectrum(δ, DMSO-d$_6$): 3.40(3H, s), 4.28(2H, s), 4.60(2H, s), 4.85(1H, s), 6.28(1H, s), 6.80(2H, d, J=8 Hz), 7.03(1H, s), 7.35(2H, d, J=8 Hz), 8.58(1H, s).

EXAMPLE 31

7β-[D-2-(4-Carboxymethoxyphenyl)-2-(6,7-dihydroxy-4-oxo-4H-1-benzopyran-3-carboxamido)acetamido]-7α-methoxy-3-acetoxymethyl-3-cephem-4-carboxylic acid (a) 7β-[D-2-(p-Methoxybenzyloxycarbonylamino)-2-[4-(p-methoxybenzyloxycarbonylmethoxy)phenyl]acetoamido]-7α-methoxy-3-acetoxymethyl-3-cephem-4-carboxylic acid:

55% Sodium hydride (349 mg) was added to a 1:1 liquid mixture of dimethylformamide and tetrahydrofuran (25 ml). The resulting mixture was agitated at −78° C. At the same temperature, 7β-[D-2-(4-hydroxyphenyl)-2-(p-methoxybenzyloxycarbonylamino)acetamido]-7α-methoxy-3-acetoxymethyl-3-cephem-4-carboxylic acid (2.46 g) in a 1:1 mixture of dimethylformamide and tetrahydrofuran (20 ml) was added dropwise over 20 minutes. After completion of the dropwise addition, the cooling bath was changed to an ice bath. One hour later, p-methoxybenzylbromoacetate (1.036 g) in tetrahydrofuran (3 ml) was added dropwise at 0° C. in the course of 5 minutes, and the resulting mixture was agitated at room temperature overnight. The liquid reaction mixture was diluted with ethyl acetate (150 ml), washed successively with 0.5N-hydrochloric acid (100 ml), water (three times; 100 ml in total), and a saturated aqueous solution of sodium chloride (50 ml), and dried over anhydrous magnesium sulfate. The solvent was thereafter evaporated. The residue was purified by silica gel column chromatography (eluent: a 9.5:0.8:0.2 mixture of chloroform, methanol and formic acid) to obtain the desired product as a solid (1.114 g).

Infrared absorption spectrum[cm$^{-1}$, Nujol(trade mark)]: 1770, 1660–1730, 1600

NMR spectrum(δ, DMSO-d$_6$-D$_2$O): 1.98(3H, s), 3.14(1H, d, J=19 Hz), 3.34(3H, s), 3.71(6H, s), 4.57(1H, d, J=14 Hz), 4.74(2H, brs.), 4.86(1H, d, J=19 Hz), 4.92(2H, s), 5.03(1H, s), 5.07(2H, s), 5.29(1H, s), 6.7–6.95(6H, m), 7.1–7.45(6H, m).

(b) Trifluoroacetic acid salt of 7β-[D-2-amino-2-(4-carboxymethoxyphenyl)-acetamido]-7α-methoxy-3-acetoxymethyl-3-cephem-4-carboxylic acid:

A 2.5:1 mixture of trifluoroacetic acid and anisole (6 ml) was cooled in an ice bath, to which the compound obtained in the above procedure (a) (600 mg) was added with stirring. The resulting mixture was stirred for 2 hours and 30 minutes. A 1:1 mixture of ethyl ether and n-hexane (60 ml) was added to the liquid reaction mixture. The resulting precipitate was collected by filtration, washed with ethyl ether, and then dried to obtain the desired product (440 mg).

Infrared absorption spectrum[cm$^{-1}$, Nujol(trade mark)]: 1770, 1670–1720, 1600

NMR spectrum(δ, DMSO-d$_6$): 1.99(3H, s), 3.42(3H, s), 4.57(1H, d, J=13 Hz), 4.66(2H, s), 4.88(1H, d, J=13 Hz), 4.95(1H, s), 5.15(1H, s), 6.92(1H, d, J=8.5 Hz), 7.42(1H, d, J=8.5 Hz).

(c) 7β-[D-2-(4-Carboxymethoxyphenyl)-2-(6,7-dihydroxy-4-oxo-4H-1-benzopyran-3-carboxamido)acetamido]-7α-methoxy-3-acetoxymethyl-3-cephem-4-carboxylic acid:

The compound obtained in the above procedure (b) (374 mg) was suspended in tetrahydrofuran (15 ml), followed by an addition at 0° C. of N,O-bis(trimethylsilyl)acetamide (593 μl). The resulting mixture was stirred for 15 minutes, to which 6,7-dihydroxy-4-oxo-4H-1-benzopyran-3-carbonyl chloride (144 mg) was added. The thus-formed mixture was agitated at 0° C. for 2 hours. Thereafter, it was treated in the same manner as in Example 1-e to obtain the desired product (250 mg).

Infrared absorption spectrum[cm$^{-1}$, Nujol(trade mark)]: 1770, 1690–1620, 1650, 1600

NMR spectrum(δ, DMSO-d$_6$): 2.00(3H, s), 3.41(3H, s), 4.66(2H, s), 5.09(1H, s), 5.73(1H, d, J=7 Hz), 6.91(2H, d, J=8 Hz), 6.99(1H, s), 7.41(2H, d, J=8 Hz), 7.41(1H, s), 8.86(1H, s), 9.70(1H, s), 10.21(1H, d, J=7 Hz).

EXAMPLE 32

7β-[D-2-(4-Carboxymethoxyphenyl)-2-(6,7-dihydroxy-2-methyl-4-oxo-4H-1-benzopyran-3-carboxamido)acetamido]-7α-methoxy-3-acetoxymethyl-3-cephem-4-carboxylic acid (a) 7β-[D-2-(p-Methoxybenzyloxycarbonylamino)-2-[4-(p-methoxybenzyloxycarbonylmethoxy)phenyl]acetamido]-7α-methoxy-3-acetoxymethyl-3-cephem-4-carboxylic acid:

55% Sodium hydride (349 mg) was added to a 1:1 liquid mixture of dimethylformamide and tetrahydrofuran (25 ml) and the resultant mixture was agitated at −78° C. At the same temperature, a solution of 7β-[D-2-(4-hydroxyphenyl)-2-(p-methoxybenzyloxycarbonylamino)acetamido]-7α-methoxy-3-acetoxymethyl-3-cephem-4-carboxylic acid (2.46 g) in a 1:1 mixture of dimethylformamide and tetrahydrofuran (25 ml) was added dropwise over 20 minutes. After completion of the dropwise addition, the cooling bath was replaced to an ice bath. One hour later, a solution of p-methoxybenzyl bromoacetate (1.036 g) in tetrahydrofuran (3 ml) was added dropwise at 0° C. over 5 minutes. The resultant mixture was then agitated overnight at room temperature. Ethyl acetate (150 ml) was added to the liquid reaction mixture, and the resultant mixture was washed successively with 0.5N-HCl (100 ml), water (3 times, 100 ml in total) and a saturated aqueous solution of sodium chloride (50 ml). It was then dried over anhydrous magnesium sulfate and the solvent was evaporated. The residue was purified by silica gel column chromatography (chloroform:methanol:formic acid=9.5:0.8:0.2) to obtain the desired product as a solid matter (1.114 g).

Infrared absorption spectrum[cm$^{-1}$, Nujol(trade mark)]: 1770, 1660–1730, 1600.

NMR spectrum(δ, DMSO-d$_6$-D$_2$O): 1.98(3H, s), 3.14(1H, d, J=19 Hz), 3.34(3H, s), 3.71(6H, s), 4.57(1H, d, J=14 Hz), 4.74(2H, br.s), 4.86(1H, d, J=19 Hz), 4.92(2H, s), 5.03(1H, s), 5.07(2H, s), 5.29(1H, s), 6.7–6.95(6H, m), 7.1–7.45(6H, m).

(b) Trifluoroacetic acid salt of 6β-[D-2-amino-2-(4-carboxymethoxyphenyl)acetamido]-7α-methoxy-3-acetoxymethyl-3-cephem-4-carboxylic acid:

A 2.5:1 mixture of trifluoroacetic acid and anisole (6 ml) was cooled over ice bath, to which the compound (600 mg) obtained in the above procedure (a) was added with stirring. The resultant mixture was agitated for further 2 hours and 30 minutes. A 1:1 mixture of ethyl ether and n-hexane (60 ml) was added to the liquid reaction mixture. The resultant precipitate was collected by filtration, washed with ethyl ether and then dried to obtain the desired product (440 mg).

Infrared absorption spectrum[cm$^{-1}$, Nujol(trade mark)]: 1770, 1670–1720, 1600.

NMR spectrum(δ, DMSO-d$_6$): 1.99(3H, s), 3.42(3H, s), 4.57(1H, d, J=3 Hz), 4.66(2H, s), 4.88(1H, d, J=13 Hz), 4.95(1H, s), 5.15(1H, s), 6.92(1H, d, J=8.5 Hz), 7.42(1H, d, J=8.5 Hz).

(c) 7β-[D-2-(4-Carboxymethoxyphenyl)-2-(6,7-diacetoxy-2-methyl-4-oxo-4H-1-benzopyran-3-carboxamido)acetamido]-7α-methoxy-3-acetoxymethyl-3-cephem-4-carboxylic acid:

A mixture of the compound (5.2 g) obtained in the above procedure (b), N,O-bis(trimethylsilyl)acetamide (8.2 ml) and tetrahydrofuran (200 ml) was stirred for 10 minutes, followed by an addition of 6,7-diacetoxy-2-methyl-4-oxo-4H-1-benzopyran-3-carbonyl chloride (2.69 g). After stirring the resultant mixture for 1 hour, 1N—HCl was added to the resultant mixture to make it acidic. The resultant acidic mixutre was extracted with ethyl acetate (400 ml). The organic layer was washed with water and a saturated aqueous solution of sodium chloride, followed by an addition of anhydrous sodium sulfate to dry the solution. The solvent was evaporated and the residue was taken up in ethyl acetate. The resultant solution was added to ethyl ether (400 ml). The resultant precipitate was collected by filtration and then dried to obtain the desired product (6.1 g). Infrared absorption spectrum[cm$^{-1}$, Nujol(trade mark)]: 1770, 1690–1760, 1650, 1620.

NMR spectrum(δ, DMSO-d$_6$): 2.00(3H, s), 2.32(3H, s), 2.34(3H, s), 2.57(3H, s), 3.44(3H, s), 4.59(1H, d, J=12 Hz), 4.66 (2H, s), 4.90(1H, d, J=12 Hz), 5.10(1H, s), 5.63(1H, d, J=8 Hz), 6.88(2H, d, J=8 Hz), 7.41(2H, d, J=8 Hz), 7.71(1H, s), 7.91(1H, s), 9.39(1H, d, J=8 Hz), 9.66(1H, s).

(d) 7β-[D-2-(4-Carboxymethoxyphenyl)-2-(6,7-dihydroxy-2-methyl-4-oxo-4H-1-benzopyran-3-carboxamido)acetamido]-7α-methoxy-3-acetoxymethyl-3-cephem-4-carboxylic acid:

The compound (6.1 g) obtained in the above procedure (c) was suspended in ethanol (100 ml), followed by an addition of a 0.5N aqueous solution (60 ml) of sodium hydrogencarbonate. The resultant mixture was stirred at 40° C. for 1 hour and 30 minutes. The liquid reaction mixture was made acidic with 1N-HCl and then extracted with ethyl acetate. The organic layer was washed with water and a saturated aqueous solution of sodium chloride. Anhydrous magnesium sulfate was then added to the thus-washed solution to dry the same. The solvent was evaporated and ethyl ether was added to the residue to solidify the same. The resultant solid matter was collected to give the desired product (3.28 g).

Infrared absorption spectrum[cm$^{-1}$, Nujol(trade mark)]: 1770, 1750, 1705, 1620.

NMR spectrum(δ, DMSO-d$_6$): 2.01(3H, s), 2.59(3H, s), 3.43(3H, s), 4.60(1H,d, J=12 Hz), 4.66(2H, s), 4.90(1H, d, J=12 Hz), 5.09(1H,s), 5.66(1H, d, J=8 Hz), 6.88(1H, s), 6.93(2H, d, J=8 Hz), 7.31(1H, s), 7.40(2H, d, J=8 Hz).

EXAMPLE 33

Disodium 7β-[D-2-(4-carboxymethoxyphenyl)-2-(6,7-dihydroxy-2-methyl-4-oxo-4H-1-benzopyran-3-carboxamido)acetamido]-7α-methoxy-3-acetoxymethyl-3-cephem-4-carboxylate Water (9.8 ml) was added to a mixture of the compound (3.28 g) obtained in Example 32 and sodium acetate (914 mg). The resultant mixture was agitated to dissolve the latter in the water. Methanol (20 ml) was added to the solution and the thus-formed solution was added to isopropyl alcohol (200 ml). The resultant precipitate was collected by filtration, and washed with isopropyl alcohol and ethyl ether to obtain the desired product (312 g).

Infrared absorption spectrum[cm$^{-1}$, Nujol(trade mark)]: 1750, 1610–1650.

NMR spectrum($\delta$, DMSO-d$_6$): 1.98(3H, s), 2.59(3H, s), 2.97(1H, d, J=17 Hz), 3.41(3H, s), 3.44(1H, d, J=17 Hz), 4.26(2H, s), 4.90(1H, s), 5.65(1H, d, J=8 Hz), 6.71(1H, s), 6.82(2H, d, J=8 Hz), 7.17(1H, s), 7.38(2H, d, J=8 Hz).

EXAMPLE 34

Disodium 7β-[D-2-(4-carboxymethoxyphenyl)-2-(6,7-dihydroxy-4-oxo-4H-1-benzopyran-3-carboxamido)acetamido]-7α-methoxy-3-acetoxymethyl-3-cephem-4-carboxylate Trifluoroacetic acid salt of 7β-[D-2-amino-2-(4-carboxymethoxyphenyl)acetamido]-7α-methoxy-3-acetoxymethyl-3-cephem-4-carboxylic acid (1.900 g) was suspended in tetrahydrofuran (95 ml) and the resultant suspension was ice-cooled.

After adding N,O-bis(trimethylsilyl)acetamide (3.77 ml) to the suspension and stirring the resultant mixture, 6,7-dihydroxy-4-oxo-4H-1-benzopyran-3-carbonyl chloride (806 mg) was added and the thus-obtained mixture was stirred at 0° C. for 2 hours and 10 minutes. Ethyl acetate (500 ml) was added to the liquid reaction mixture and the resultant mixture was washed with 1N-HCl, water and a saturated aqueous solution of sodium chloride. The thus-washed mixture was extracted with an aqueous solution of sodium acetate (550 mg/15.2 ml) and the water layer was then separated. Ethanol (70 ml) and isopropanol (70 ml) were added to the water layer. The resultant precipitate was collected by filtration, and then washed with isopropanol and ethyl ether to obtain the desired object (1.412 g).

Infrared absorption spectrum[cm$^{-1}$, Nujol(trade mark)]: 1755, 1720, 1650, 1595.

NMR spectrum($\delta$, DMSO-d$_6$-D$_2$O): 1.90(3H, s), 2.97(1H, d, J=18 Hz), 3.97(1H, d, J=18 Hz), 3.41(3H, s), 4.20(2H, s), 4.63(1H, d, J=13.5 Hz), 4.82(1H, d, J=13.5 Hz), 4.90(1H, s), 5.70(1H, s), 6.60(1H, s), 6.83(2H, d, J=8.5 Hz), 7.22(1H, s), 7.36(2H, d, J=8.5 Hz), 8.71(1H, s).

EXAMPLE 35

Disodium 7β-[D-2-(4-carboxymethoxyphenyl)-2-(6,7-dihydroxy-1-ethyl-1,4-dihydro-4-oxoquinoline-3-carboxamido)acetamido]-3-acetoxymethyl-3-cephem-4-carboxylate (a) 7β-[D-2-(4-Carboxymethoxyphenyl)-2-(6,7-diacetoxy-1-ethyl-1,4-dihydro-4-oxoquinoline-3-carboxamido)acetamido]-3-acetoxymethyl-3-cephem-4-carboxylic acid:

A mixture of trifluoroacetic acid salt of 7β-[D-2-amino-2-(4-carboxymethoxyphenyl)acetamido]-3-acetoxymethyl-3-cephem-4-carboxylic acid (5.26 g) N,O-bis(trimethylsilyl)acetamide (9.3 ml) and tetrahydrofuran (200 ml) was stirred for 20 minutes, followed by an addition of 6,7-diacetoxy-1-ethyl-1,4-dihydro-4-oxoquinoline-3-carbonyl chloride (2.7 g). The resultant mixture was stirred for 2 hours. Water (300 ml) and ethyl acetate (400 ml) were added to the liquid reaction mixture, and the resultant precipitate was removed by filtration. The organic layer was separated and, after washing it with water and a saturated aqueous solution of sodium chloride, anhydrous magnesium sulfate was added to the thus-washed organic solution to dry the same. The solvent was then removed and ethyl ether was added to the residue to solidify the same. The resultant solid matter was collected by filtration to obtain the desired product (3.01 g).

Infrared absorption spectrum[cm$^{-1}$, Nujol(trade mark)]: 1700–1780, 1600.

NMR spectrum($\delta$, DMSO-d$_6$): 1.38(3H, t, J=7 Hz), 2.00(3H, s), 2.33(3H, s), 2.35(3H, s), 3.33(1H, d, J=21 Hz), 3.58(1H, d, J=21 Hz), 4.1–4.60(2H, m), 4.62(2H, s), 4.63(1H, d, J=14 Hz), 4.97(1H, d, J=14 Hz), 5.00(1H, d, J=5 Hz), 5.6–5.9(2H, m), 6.84(2H, d, J=8 Hz), 7.34(2H, d, J=8 Hz), 7.90(1H, s), 8.16(1H, s), 8.82(1H, s).

(b) 7β-[D-2-(4-Carboxymethoxyphenyl)-2-(6,7-dihydroxy-1-ethyl-1,4-dihydro-4-oxoquinoline-3-carboxamido)acetamido]-3-acetoxymethyl-3-cephem-4-carboxylic acid:

The compound (2.91 g) obtained in the above procedure (a), sodium hydrogencarbonate (1.19 g), water (25 ml) and ethanol (50 ml) were agitated at 40° C. for 1 hour and 15 minutes. The liquid reaction mixture was made acidic by a dilute hydrochloric acid and then extracted with ethyl acetate. The extract was washed with water and a saturated aqueous solution of sodium chloride, and anhydrous magnesium sulfate was added to the thus-washed extract to dry the same. The solvent was evaporated and ethyl ether was added to the residue to solidify the same. The resultant solid matter was collected by filtration to obtain the desired product (2.146 g).

Infrared absorption spectrum[cm$^{-1}$, Nujol(trade mark)]: 1760, 1700, 1650, 1600.

(c) Disodium 7β-[D-2-(4-carboxymethoxyphenyl)-2-(6,7-dihydroxy-1-ethyl-1,4-dihydro-4-oxoquinoline-3-carboxamido)acetamido]-3-acetoxymethyl-3-cephem-4-carboxylate:

The compound (2.146 g) obtained in the above procedure (b) and sodium acetate (594 mg) were dissolved with stirring in water (14 ml), followed by an addition of ethanol (140 ml). The resultant precipitate was collected by filtration, washed with ethyl ether, and then dried to obtain the desired product (2.2 g).

Infrared absorption spectrum[cm$^{-1}$, Nujol(trade mark)]: 1750, 1630, 1600.

NMR spectrum($\delta$, DMSO-d$_6$-D$_2$O): 1.36(3H, t, J=6 Hz), 3.12(1H, d, J=17 Hz), 3.42(1H, d, J=17 Hz), 4.17(2H, s), 4.68(1H, d, J=10 Hz), 4.83(1H, d, J=5 Hz), 4.92(1H, d, J=10 Hz), 5.53(1H, d, J=5 Hz), 5.74(1H, d, J=10 Hz), 6.79(2H, d, J=8 Hz), 7.03(1H, s), 7.30(2H, d, J=8 Hz), 7.60(1H, s), 8.54(1H, s).

EXAMPLE 36

7β-[D-2-[6,7-Bis(ethoxycarbonyloxy)-2-methyl-4-oxo-4H-1-benzopyran-3-carboxamido]acetamido]-3-acetoxymethyl-3-cephem-4-carboxylic acid Trifluoroacetic acid salt of 7β-[D-2-amino-2-(4-carboxymethoxyphenyl)acetamido]-3-acetoxymethyl-3-cephem-4-carboxylic acid (1.187 g) was added with ice-cooling to a liquid mixture of tetrahydrofuran (24 ml) and N,O-bis(trimethylsilyl)acetamide (1.98 ml). The resulting mixture was then stirred to dissolve the salt in the liquid mixture.

A mixture of 6,7-dihydroxy-2-methyl-4-oxo-4H-1-benzopyran-3-carboxylic acid (472 mg) and tetrahydrofuran (20 ml) was cooled in an ice salt bath, followed by an addition of triethylamine (878 μl) and a further addition of ethyl chloroformate (600 μl) with stirring. The thus-obtained mixture was thereafter added to the above-prepared solution. The reactants were allowed to undergo a reaction for 20 minutes. After adding 0.4N—HCl (50 ml) to the liquid reaction mixture, the resulting mixture was extracted with ethyl acetate (150 ml). The extract was washed with water and, after adding anhydrous magnesium sulfate to the thus-washed extract to dry the same, the solvent was evaporated. Ethyl ether was added to the residue to solidify the same and to obtain the desired product (1.145 g).

Infrared absorption spectrum[cm$^{-1}$, Nujol(trade mark)]: 1760, 1730, 1640, 1610.

NMR spectrum (δ, DMSO-d$_6$): 1.29(6H, t, J=7.5 Hz), 2.00(3H, s), 2.57(3H, s), 4.27(2H, q, J=7.5 Hz), 4.29(2H, q, J=7.5 Hz), 4.63(2H, s), 4.63(2H, d, J=11 Hz), 4.95(2H, d, J=11 Hz), 4.99(1H, d, J=5 Hz), 5.6–5.8(2H, m), 6.87(2H, d, J=9 Hz), 7.37(2H, d, J=9 Hz), 7.88(1H, s), 8.05(1H, s).

EXAMPLE 37

Disodium 7β-[D-2-(4-carboxymethoxyphenyl)-2-(6,7-dihydroxy-2-methyl-4-oxo-4H-1-benzopyran-3-carboxamido)acetamido]-3-acetoxymethyl-3-cephem-4-carboxylate A mixture of the compound (944 mg) obtained in Example 36, sodium hydrogencarbonate (377 mg), water (8.8 ml) and ethanol (4.4 ml) was heated to 45° C.-50° C. and stirred for 1 hour and a half. After adding 0.5N—HCl (12 ml) to the liquid reaction mixture, the resulting mixture was extracted with ethyl acetate (50 ml). The extract was washed with an aqueous 15% methanol solution. The resulting organic layer was added and extracted with water (2.5 ml) containing sodium acetate (201 mg). Isopropyl alcohol (35 ml) was added to the resulting aqueous layer to cause a solid to precipitate. The solid was collected by filtration and washed first with ethanol and then with ethyl ether to obtain the desired product (590 mg).

The infrared absorption spectrum and NMR spectrum of the thus-obtained compound were identical with those of the compound obtained in Example 29.

EXAMPLE 38

Disodium 7β-[D-2-(4-carboxymethoxyphenyl)-2-(6,7-dihydroxy-2-methyl-4-oxo-4H-1-benzopyran-3-carboxamido)acetamido]-3-acetoxymethyl-3-cephem-4-carboxylate Trifluoroacetic acid salt of 7β-[D-2-amino-2-(4-carboxymethoxyphenyl)-acetamido]-3-acetoxymethyl-3-cephem-4-carobxylic acid (1.187 g) was dissolved with ice-cooling in acetonitrile (24 ml) which contained N,O-bis(trimethylsilyl)acetamide (1.98 ml).

A mixture of 6,7-dihydroxy-2-methyl-4-oxo-4H-1-benzopyran-3-carboxylic acid (472 mg) and acetonitrile (20 ml) was cooled in an ice salt bath, followed by an addition of triethylamine (878 μl) and a further addition of ethyl chloroformate (60 μl) with stirring. The resulting mixture was then reacted with the above-obtained solution. The reactants were allowed to undergo a reaction for 20 minutes. After adding 0.4N—HCl (50 ml) to the liquid reaction mixture, the resulting mixture was extracted with ethyl acetate (120 ml). The extract was washed first with water and then with a saturated solution of sodium chloride in water. The organic layer was extracted first with water (24 ml) containing sodium hydrogencarbonate (672 mg) and then with water (6 ml). Both water layers were combined together and then washed with ethyl acetate. Thereafter, the resulting mixture was heated for 1 hour and 20 minutes in an oil bath of 50° C. After allowing the resulting mixture to cool down, ethyl acetate (80 ml), 1N—HCl (10 ml) and methanol (10 ml) were added to the liquid reaction mixture. The resulting mixture was shaken well and the ethyl acetate layer was separated and collected. After washing the ethyl acetate layer with water, the ethyl acetate layer was extracted with water (3 ml) containing sodium acetate (345 mg). Isopropanol (30 ml) was then added to the resulting water layer to form a precipitate, which was then collected by filtration. The precipitate was washed first with ethanol and then with ethyl ether to obtain the desired product (552 mg).

The infrared absorption spectrum and NMR spectrum of the thus-obtained compound were identical with those of the compound obtained in Example 29.

EXAMPLE 39

Disodium 7β-[D-2-(4-carboxymethoxyphenyl)-2-(6,7-dihydroxy-2-methyl-4-oxo-4H-1-benzopyran-3-carboxamido)acetamido]-3-acetoxymethyl-3-cephem-4-carboxylate (a) N-Hydroxysuccinimide ester of 6,7-dihydroxy-2-methyl-4-oxo-4H-1-benzopyran-3-carboxylic acid:

Thionyl chloride (4.33 ml) was added with ice-cooling to a mixture of 6,7-dihydroxy-2-methyl-4-oxo-4H-1-benzopyran-3-carboxylic acid (4.72 g), N-hydroxysuccinimide (5.75 g), dimethylformamide (71 ml) and pyridine (4.85 ml). The resulting mixture was stirred at the same temperature for 10 minutes. The temperature of the liquid reaction mixture was allowed to rise to room temperature. After adding 0.2N—HCl (0.3 l), the resulting mixture was extracted with ethyl acetate (1 liter). The extract was washed with water and then added with methanol (5 ml). Activated carbon was added to the resulting mixture to decolorize the same, followed by an addition of anhydrous magnesium sulfate to dry the same. The solvent was evaporated. Ethyl ether was added to the residue to solidify the same and to obtain the desired product (3.662 g).

Infrared absorption spectrum[cm$^{-1}$, Nujol(trade mark)]: 1800, 1780, 1720, 1615, 1590.

NMR spectrum($\delta$, DMSO-d$_6$): 2.63(3H, s), 2.88(4H, s), 6.90(1H, s), 7.28(1H, s).

(b) Disodium 7$\beta$-[D-2-(4-carboxymethoxyphenyl)-2-(6,7-dihydroxy-2-methyl-4-oxo-4H-1-benzopyran-3-carboxamido)acetamido]-3-acetoxymethyl-3-cephem-4-carboxylate:

Trifluoroacetic acid salt of 7$\beta$-[D-2-amino-2-(4-carboxymethoxyphenyl)-acetamido]-3-acetoxymethyl-3-cephem-4-carboxylic acid (1.78 g) was added with ice-cooling to a liquid mixture of tetrahydrofuran (36 ml) and N,O-bis(trimethylsilyl)acetamide (3.37 ml). The resulting mixture was stirred to dissolve the former in the latter. To the resulting solution, was added the compound (1 g) obtained in the above procedure (a). The resulting mixture was stirred with ice cooling for 2 hours and then for further 2 hours at room temperature. After adding 0.2N—HCl (200 ml) to the liquid reaction mixture, the resulting mixture was extracted with ethyl acetate (300 ml). The extract was washed with water and then extracted with water (3 ml) which contained sodium acetate (541 mg). The organic layer was again extracted with water (1.5 ml). Both water layers were combined together and the resulting precipitate was collected by filtration. The precipitate was washed first with ethanol and then with ethyl ether to obtain the desired product (1.233 g). In addition, ethanol (15 ml) was added to the filtrate and the resulting precipitate was collected by filtration. It was washed with ethanol and ethyl ether to obtain the desired product (0.391 g). The total yield of the thus-obtained desired product was 1.624 g.

The infrared absorption spectrum and NMR spectrum of the thus-obtained compound were identical with those of the compound obtained in Example 29.

EXAMPLE 40

Sodium 7$\beta$-[D-2-(4-carboxymethoxyphenyl)-2-(6,7-dihydroxy-2-methyl-4-oxo-4H-1-benzopyran-3-carboxamido)acetamido]-3-pyridiniummethyl-3-cephem-4-carboxylate A mixture of the compound (2 g) obtained in Example 29, pyridine (1 g), sodium iodide (40 g) and water (20 ml) was stirred at 60° C. for 2 hours, and ethanol (200 ml) was added to the liquid reaction mixture. The resultant precipitate was collected by filtration and then washed with ethanol and ethyl ether. The thus-obtained solid matter was taken up in water (30 ml), followed by an addition of ethanol (200 ml). The thus-formed precipitate was collected by filtration. The resultant solid matter was dissolved in water (70 ml), followed by an addition of 1N—HCl (5 ml). The resultant precipitate was collected by filtration and then washed with acetone and ethyl ether. The thus-washed precipitate was dissolved in dimethylformamide (10 ml), to which acetone (20 ml) was added. The resultant precipitate was collected by filtration. The thus-obtained solid matter was dissolved in dimethylformamide (10 ml), to which acetone (30 ml) was added. The resultant precipitate was collected by filtration. Sodium acetate (71 mg) and water (8 ml) were added to the thus-obtained precipitate to dissolve the same precipitate. Ethanol (100 ml) was added to the resultant solution and the thus-formed precipitate was collected by filtration to obtain the desired product (377 mg).

Infrared absorption spectrum[cm$^{-1}$, Nujol(trade mark)]: 1760, 1610–1650.

NMR spectrum($\delta$, DMSO-d$_6$): 2.58(3H, s), 3.02(1H, d, J=18 Hz), 3.48(1H, d, J=18 Hz), 4.35(2H, s), 4.95(1H, d, J=5 Hz), 5.00(1H, d, J=11 Hz), 5.26(1H, d, J=11 Hz), 5.43–5.82(2H, m), 6.81(2H, d, J=8 Hz), 6.92(1H, s), 7.24(1H, s), 7.24(2H, d, J=8 Hz), 8.02–8.20(2H, m), 8.50–8.50(1H, m), 9.25(2H, d, J=8 Hz).

Solubility(in distilled water at 25° C.): 30% or higher.

EXAMPLE 41

Sodium 7$\beta$-[D-2-(4-carboxymethoxyphenyl)-2-(6,7-dihydroxy-2-methyl-4-oxo-4H-1-benzopyran-3-carboxamido)acetamido]-3-(4-carbamoylpyridinium)-methyl-3-cephem-4-carboxylate A mixture of the compound (2.93 g) obtained in Example 29, isonicotinic amide (14.6 g), sodium iodide (58.5 g) and water (44 ml) was stirred at 70° C. for 1 hour and 35 minutes. Ethanol (290 ml) was added to the liquid reaction mixture, and the resultant precipitate was collected by filtration and washed with ethanol, acetone and ethyl ether. The thus-washed precipitate was dissolved in water (83 ml), followed by an addition of 0.5N—HCl (12 ml). The resultant precipitate was collected by filtration, and washed successively with water, a 1:1 mixture of ethanol and ethyl ether and ethanol to obtain white powder (1.67 g). It was then dissolved in dimethylformamide (16.7 ml), followed by a dropwise addition of acetone (48 ml). The thus-formed precipitate was collected by filtration and washed first with a 1:1 mixture of dimethylformamide and acetone and then with acetone to obtain white powder (1.43 g). It was taken up in an aqueous solution of sodium acetate (185 mg/14.3 ml) and, after a dropwise addition of ethanol (13 ml), the resultant mixture was ice-cooled. The resultant precipitate was collected by filtration and washed with ethanol and ethyl ether to obtain the desired product (1.29 g).

Infrared absorption spectrum[cm$^{-1}$, Nujol(trade mark)]: 1760, 1680, 1590.

NMR spectrum($\delta$, DMSO-d$_6$-D$_2$O): 2.57(3H, s), 4.30(2H, s), 4.88(1H, d, J=5 Hz), 5.12(1H, d, J=14 Hz), 5.58(1H, s), 5.61(1H, d, J=5 Hz), 5.68(1H, d, J=14 Hz), 6.75(2H, d, J=8.5 Hz), 6.85(1H, s), 7.27(1H, s), 7.30(2H, d, J=8.5 Hz), 8.38(2H, d, J=7 Hz), 9.44(2H, d, J=7 Hz).

Solubility(in distilled water at 25° C.): 30% or higher.

EXAMPLE 42

Disodium 7$\beta$-[D-2-(4-carboxymethoxyphenyl)-2-(6,7-dihydroxy-2-methyl-4-oxo-4H-1-benzopyran-3-carboxamido)acetamido]-3-[4-(2-sulfoethyl)-pyridinium]methyl-3-cephem-4-carboxylate A mixture of the compound (1.50 g) obtained in Example 29, sodium iodide (25.5 g), 2-(4-pyridyl)ethanesulfonic acid (9.90 g), a 4N aqueous solution of sodium hydroxide (10.5 ml) and water (20 ml) was stirred at 70° C. for 1 hour and 45 minutes. The liquid reaction mixture was added to ethanol (120 ml) and the resultant precipitate was collected by filtration. It was then washed with ethanol, acetone and ethyl ether. The thus-washed precipitate was dissolved in water (25 ml), followed by an addition of 0.5N—HCl (9 ml). The resultant precipitate was collected by filtration, and washed with water, acetone and ethyl ether. Thereafter, the resultant precipitate was taken up in dimethylformamide (3.8 ml), followed by a dropwise addition of acetone (8 ml). The thus-formed precipitate was collected by filtration and then washed with acetone. It was dissolved in an aqueous solution of sodium acetate (59 mg/1.9 ml), to which ethanol was added. The resultant precipitate was collected by filtration to obtain the desired product (270 mg).

Infrared absorption spectrum[cm$^{-1}$, Nujol(trade mark)]: 1765, 1668, 1640, 1605.

NMR spectrum($\delta$, DMSO-d$_6$-D$_2$O): 2.61(3H, s), 2.93(4H, s), 4.20(2H, s), 4.94(1H, d, J=5 Hz), 4.8–5.7(2H), 5.59(1H, s), 5.65(1H, d, J=5 Hz), 6.78(2H, d, J=5 Hz), 6.83(1H, s), 7.32(1H, s), 7.34(2H, d, J=8 Hz), 8.01(2H, d, J=7 Hz), 9.12(2H, d, J=7 Hz).

Solubility(in distilled water at 25° C.): 30% or higher.

EXAMPLE 43

Disodium
7$\beta$-[D-2-(4-carboxymethoxyphenyl)-2-(6,7-dihydroxy-2-methyl-4-oxo-4H-1-benzopyran-3-carboxamido)acetamido]-3-(3-carboxymethylpyridinium)-methyl-3-cephem-4-carboxylate A mixture of the compound (1.50 g) obtained in Example 29, sodium iodide (25.5 g), 3-pyridylacetic acid hydrochloride (9.9 g), 4N-aqueous solution of sodium hydroxide (25.1 ml) and water(14.5 ml) was stirred at 69° C. for 2 hours and 30 minutes. The liquid reaction mixture was added to ethanol (150 ml), and the resultant precipitate was collected by filtration and washed with ethanol and ethyl ether. It was then dissolved in water (70 ml), followed by an addition of 0.5N—HCl (9.5 ml). The resulting precipitate was collected by filtration and washed with water, acetone and ethyl ether. It was then taken up in dimethylformamide (4.3 ml), to which acetone (9 ml) was added dropwise. The resultant precipitate was collected by filtration and washed with acetone and ethyl ether. It was then dissolved in an aqueous solution of sodium acetate (77 mg/2.7 ml), followed by an addition of ethanol. The resultant precipitate was collected by filtration to obtain the desired product (324 mg).

Infrared absorption spectrum[cm$^{-1}$, Nujol(trade mark)]: 1750, 1680, 1650, 1600.

NMR spectrum($\delta$, DMSO-d$_6$-D$_2$O): 2.60(3H, s), 4.23(2H, s), 4.92(1H, d, J=5 Hz), 5.05(1H, d, J=14 Hz), 5.6(1H, d, J=14 Hz), 5.58(1H, s), 5.62(1H, d, J=5 Hz), 6.76(2H, d, J=8 Hz), 6.85(1H, s), 7.30(1H, s), 7.30(2H, d, J=8 Hz), 7.8–8.1(1H, m), 8.21(1H, d, J=8 Hz), 9.05(1H, s), 9.20(1H, d, J=6 Hz).

Solubility(in distilled water at 25° C.): 30% or higher.

EXAMPLE 44

Sodium
7$\beta$-[D-2-(4-carboxymethoxyphenyl)-2-(6,7-dihydroxy-4-oxo-4H-1-benzopyran-3-carboxamido)-acetamido]-3-pyridiniummethyl-3-cephem-4-carboxylate A mixture of the compound (2.00 g) obtained in Example 1, potassium thiocyanate (10.7 g), water (4 ml), pyridine (2.2 ml) and 2N—HCl (3 ml) was stirred at 50° C. for 16 hours. The liquid reaction mixture was added to ethanol (100 ml), and the resultant precipitate was collected by filtration and washed with ethanol, acetone and ethyl ether. The thus-obtained solid matter was dissolved in water in an amount 8 times the weight of the solid matter, followed by an addition of ethanol in an amount 10 times the weight of the water. The resultant precipitate was collected by filtration. These dissolution, precipitation and filtration procedures were repeated again to obtain yellow powder. It was then dissovled in water (76 ml), followed by an addition of 1N—HCl (4.6 ml). The resultant precipitate was collected by filtration and then washed with water, ethanol and ethyl ether. The thus-obtained solid matter was dissolved in dimethylformamide in an amount 10 times the weight of the solid and the resultant solution was added dropwise in acetone in an amount 2.2 times the weight of the dimethylformamide. The resultant precipitate was collected by filtration. These procedures were repeated twice and the resultant solid matter was then dissolved in an aqueous solution of sodium acetate (40.7 mg/2.7 ml). The resultant solution was added with ethanol (27 ml) and the resultant precipitate was collected by filtration. The thus-obtained solid matter was dissolved in water, to which ethanol was added to form a precipitate. The precipitate was collected by filtration and then washed with ethanol and ethyl ether to obtain the desired product (259 mg).

Infrared absorption spectrum[cm$^{-1}$, Nujol(trade mark)]: 1770, 1655, 1605.

NMR spectrum($\delta$, DMSO-d$_6$): 4.50(2H, s), 4.93(1H, d, J=5 Hz), 5.4–5.8(2H, m), 6.79(2H, d, J=8 Hz), 6.93(1H, s), 7.30(2H, d, J=8 Hz), 7.38(1H, s), 8.1(2H, m), 8.55(1H, m), 8.78(1H, s), 10.28(1H, d, J=7 Hz).

Solubility(in distilled water at 25° C.): 30% or higher.

EXAMPLE 45

Sodium
7$\beta$-[D-2-(4-carboxymethoxyphenyl)-2-(6,7-dihydroxy-4-oxo-4H-1-benzopyran-3-carboxamido)-acetamido]-3-(4-carbamoylpyridinium)methyl-3-cephem-4-carboxylate A mixture of the compound (200 mg) obtained in Example 1, isonicotinamide (45 mg), sodium idodide (187 mg) and water (0.6 ml) was stirred at 60° C. for 3 hours. Water (3 ml) and a saturated aqueous solution of sodium hydrogencarbonate (3 ml) were added to the liquid reaction mixture. The resultant mixture was charged in a column packed with "Dia-Ion HP20" (300 ml; trade mark for a styrene/divinylbenzene copolymer produced and marketed by Mitsubishi Chemical Industries, Ltd.). Water (100 ml) was passed through the column. The column was eluted by the gradient method, using water (2 liters) and methanol (2 liters). Fractions, which contained the desired product, were collected. After evaporating methanol, the residue was lyophilized to obtain the desired product (19 mg).

Infrared absorption spectrum[cm$^{-1}$, Nujol(trade mark)]: 1760, 1655, 1605.

NMR spectrum($\delta$, DMSO-d$_6$-D$_2$O): 4.15(2H, s), 4.92(1H, d, J=5 Hz), 5.5–5.8(2H, m), 6.35(1H, s), 6.76(2H, d, J=8 Hz), 7.08(1H, s), 7.25(2H, d, J=8 Hz), 8.33(2H, d, J=7 Hz), 8.59(1H, s), 9.34(2H, d, J=7 Hz).

Solubility(in distilled water at 25° C.): 30% or higher.

EXAMPLE 46

Disodium
7β-[D-2-(4-carboxymethoxyphenyl)-2-(6,7-dihydroxy-4-oxo-4H-1-benzopyran-3-carboxamido)-acetamido]-3-[4-(2-sulfoethyl)pyridinium]methyl-3-cephem-4-carboxylate A 1N aqueous solution of sodium hydroxide was added to a mixture of the compound (100 mg) obtained in Example 1, 2-(4-pyridyl)ethanesulfonic acid (54 mg), sodium iodide (550 mg) and water (6 ml) to adjust the pH of the resultant solution to 7.0. After stirring it at 60° C. for 5 hours and 30 minutes, water (1.5 ml) and a saturated aqueous solution of sodium hydrogencarbonate (1.5 ml) were added to the liquid reaction mixture. It was then charged on a column packed with "Dia-Ion HP 20" (150 ml) and water (50 ml) was passed therethrough. The column was eluted by the gradient method, using water (1 liter) and methanol (1 liter). Fractions, which contained the desired product, were collected. After evaporating methanol, the residue was lyophilized to obtain the desired product (13 mg).

Infrared absorption spectrum[$cm^{-1}$, Nujol(trade mark)]: 1760, 1655, 1600.

NMR spectrum($\delta$, DMSO-$d_6$-$D_2O$): 4.12(2H, s), 4.93(1H, d, J=5 Hz), 5.5–5.8(2H, m), 6.43(1H, s), 6.75(2H, d, J=8 Hz), 8.00(2H, d, J=7 Hz), 8.62(1H, s), 9.16(2H, d, J=7 Hz).

Solubility(in distilled water at 25° C.): 30% or higher.

EXAMPLE 47

Sodium
7β-[D-2-(carboxymethoxyphenyl)-2-(6,7-dihydroxy-4-oxo-4H-1-benzopyran-3-carboxamido)-acetamido]-3-pyridiniummethyl-3-cephem-4-carboxylate (a) 7β-[D-2-(4-carboxymethoxyphenyl)-2-(6,7-dihydroxy-4-oxo-4H-1-benzopyran-3-carboxamido)acetamido]-3-benzoylthiomethyl-3-cephem-4-carboxylic acid:

Disodium 7β-[D-2-(4-carboxymethoxyphenyl)-2-(6,7-dihydroxy-4-oxo-4H-1-benzopyran-3-carboxamido)acetamido]-3-acetoxymethyl-3-cephem-4-carboxylate (946 mg) was dissolved in water (12 ml), to which thiobenzoic acid (551 μl) was added. Thereafter, a solution of sodium hydrogencarbonate (393 mg) in water (5 ml) was added. The resultant mixture was stirred at 55° C. for 14 hours. After cooling the liquid reaction mixture, it was added to ethyl acetate (500 ml). The resultant mixture was washed successively with 0.2N—HCl (100 ml) and water (100 ml×3 times) and magnesium sulfate was added to the thus-washed mixture to dry the same. The solvent was evaporated and the residue was washed with ether to obtain the desired product (695 mg).

Infrared absorption spectrum[$cm^{-1}$, Nujol(trade mark)]: 1760, 1720, 1660, 1630, 1605.

NMR spectrum($\delta$, DMSO-$d_6$): 3.95(1H, d, J=13 Hz), 4.31(1H, d, J=13 Hz), 4.64(2H, s), 5.04(1H, d, J=5 Hz), 5.6–5.9(2H, m), 6.88(1H, d, J=8.5 Hz), 6.99(1H, s), 7.36(1H, d, J=8.5 Hz), 7.43(1H, s), 7.5–8.0(5H, m), 8.85(1H, s), 9.44(1H, d, J=8 Hz), 10.32(1H, d, J=8 Hz).

(b) Disodium salt of the compound obtained in the above procedure (a):

The compound (668 mg) obtained in the above procedure (a) was dissolved in a 1:1:1 mixture of tetrahydrofuran, methanol and dimethylformamide, to which a 1M methanol solution of sodium acetate (1.84 ml) was added with stirring. Ten minutes later, most of tetrahydrofuran and methanol were evaporated, and ethanol (100 ml) was added with stirring to the residue. The precipitate was collected by filtration, and washed successively with ethanol and then with ethyl ether to obtain the desired product (530 mg). In addition, the desired product was also recovered from the above filtrate (49 mg).

Infrared absorption spectrum[$cm^{-1}$, Nujol(trade mark)]: 1760, 1660, 1605.

NMR spectrum($\delta$, DMSO-$d_6$): 4.17(2H, br.s), 4.28(2H, s), 4.90(1H, d, J=5 Hz), 5.57(1H, d, J=5 Hz), 5.72(1H, s), 6.84(2H, d, J=8.5 Hz), 6.96(1H, s), 7.34(2H, d, J=8.5 Hz), 7.41(1H, s), 7.5–8.0(5H, m), 8.81(1H, s).

(c) Sodium 7β-[D-2-(4-carboxymethoxyphenyl)-2-(6,7-dihydroxy-4-oxo-4H-1-benzopyran-3-carboxamido)acetamido]-3-pyridiniummethyl-3-cephem-4-carboxylate:

The compound (700 mg) obtained in the above procedure (b) was suspended in a liquid mixture of pyridine (7 ml) and dioxane (7 ml), to which a 40% aqueous solution of mercuric perchlorate (4.7 ml) was added. The resultant mixture was agitated at 55° C. for 45 minutes. The liquid reaction mixture was ice-cooled, followed by an addition of thiobenzoic acid (2.3 ml). The resultant mixture was stirred at room temperature for 10 minutes and the solution was then concentrated under reduced pressure. Water (50 ml) was added to the residue, and the resultant mixture was filtered using celite. The celite was then washed with water (120 ml). The filtrate was washing were combined and, after being washed with chloroform (once) and ethyl ether (twice), concentrated under reduced pressure. The residue was suspended in water (20 ml), followed by an addition with ice-cooling of a 1N aqueous solution of sodium hydroxide (1.8 ml) to dissolved the solid matter. The resultant solution was charged on a column packed with "Dia-Ion HP20" (1 liter) and water (200 ml) was passed through the column. The column was eluted by the gradient method, using water and methanol. Fractions, which contained the desired product, were collected. After evaporating methanol, the residue was lyophilized to obtain the desired product (84 mg).

The thus-obtained compound had the same infrared absorption spectrum and NMR spectrum as the compound of Example 44.

EXAMPLE 48

Sodium
7β-[D-2-(4-carboxymethoxyphenyl)-2-(6,7-dihydroxy-2-methyl-4-oxo-4H-1-benzopyran-3-carboxamido)acetamido]-7α-methoxy-3-pyridiniummethyl-3-cephem-4-carboxylate A mixture of the compound (2.59 g) obtained in Example 32, water (12.9 ml), pyridine (5.8 ml) and sodium iodide (3.88 g) was stirred at 75° C. for 1 hour and 30 minutes. The liquid reaction mixture was added to ethanol (100 ml) and the resultant precipitate was collected by filtration. The precipitate was washed with acetone and ethyl ether. It was then dissolved in water (80 ml), followed by an addition of 0.5N—HCl (8 ml). The resultant precipitate was collected by filtration, and then washed with water and ethyl ether. The thus-obtained solid matter was dissolved in dimethylformamide in an amount 10 times the weight of the solid matter, and the resultant solution was added dropwise to acetone in an amount twice the weight of the dimethylformamide.

The thus-formed precipitate was collected by filtration. These procedures were repeated again and the resultant solid matter was dissolved in an aqueous solution of sodium acetate (107 mg/6.5 ml). Ethanol (25 ml) was added to the resultant solution and the resultant precipitate was collected by filtration. The precipitate was then charged on a column containing "Sephadex G25 superfine" (trade mark, product of Pharmacia AB) (120 g), and then eluted with a 1:9 mixture of methanol and water. Fractions, which contained the desired product, were collected. Methanol was evaporated and the residue was lyophilized to obtain the desired product (106 mg).

Infrared absorption spectrum[cm$^{-1}$, Nujol(trade mark)]: 1760, 1655, 1600.

NMR spectrum($\delta$, DMSO-d$_6$-D$_2$O): 2.57(3H, s), 3.42(3H, s), 4.21(2H, s), 4.95(1H, s), 5.12(1H, d, J=14 Hz), 5.50(1H, d, J=14 Hz), 5.58(1H, s), 6.74(2H, d, J=9 Hz), 6.84(1H, s), 7.25(1H, s), 7.35(2H, d, J=9 Hz), 7.9–8.2(2H, m), 8.4–8.7(1H, m), 9.0–9.3(2H, m).

Solubility(in distilled water at 25° C.): 30% or higher.

EXAMPLE 49

7$\beta$-[D-2-(4-Carboxymethoxyphenyl)-2-(6,7-dihydroxy-2-methyl-4-oxo-4H-1-benzopyran-3-carboxamido)-acetamido]-7$\alpha$-methoxy-3-(4-carbamoylpyridinium)-methyl-3-cephem-4-carboxylate A mixture of the compound (2.8 g) obtained in Example 33, sodium iodide (56 g), isonicotinamide (14 g) and water (47.6 ml) was stirred at 70° C. for 4 hours. Ethanol (500 ml) was added to the liquid reaction mixture. The resultant precipitate was collected by filtration and washed with ethanol and ethyl ether. It was then taken up in water (10 ml) and the resultant aqueous solution was made acidic with dilute hydrochloric acid. The resultant precipitate was collected by filtration and washed with acetone and ethyl ether. It was thereafter dissolved in dimethylformamide (17 ml), followed by an addition of acetone (34 ml) to form a precipitate. The precipitate was collected by filtration and was again dissolved in dimethylformamide (4 ml). Acetone (8 ml) was added to form a precipitate, which was collected by filtration to obtain the desired product (360 mg).

Infrared absorption spectrum[cm$^{-1}$, Nujol(trade mark)]: 1760, 1680, 1650, 1620.

NMR spectrum($\delta$, DMSO-d$_6$): 2.58(3H, s), 3.42(3H, s), 4.60(2H, s), 4.99(1H, s), 5.22(1H, d, J=12 Hz), 5.50–5.70(2H, m), 6.80(2H, d, J=8 Hz), 6.89(1H, s), 7.27(1H, s), 7.38(2H, d, J=8 Hz), 8.38(2H, d, J=8 Hz), 9.38(2H, d, J=8 Hz).

EXAMPLE 50

Sodium 7$\beta$-[D-2-(4-carboxymethoxyphenyl)-2-(6,7-dihydroxy-2-methyl-4-oxo-4H-1-benzopyran-3-carboxamido)acetamido]-7$\alpha$-methoxy-3-(4-carbamoylpyridinium)methyl-3-cephem-4-carboxylate The compound (340 mg) obtained in Example 49 and sodium acetate (42 mg) were dissolved in water (4 ml) and the insoluble matter was filtered off. To the solution, methanol (5 ml) was added first, followed by an addition of ethanol (50 ml). The resultant precipitate was collected by filtration, washed with ethanol and ethyl ether, and dried to obtain the desired product (225 mg).

Infrared absorption spectrum[cm$^{-1}$, Nujol(trade mark)]: 1760, 1610–1660.

NMR spectrum($\delta$, DMSO-d$_6$): 2.57(3H, s), 3.42(3H, s), 4.20(2H, s), 4.96(1H, s), 5.18(1H, d, J=13 Hz), 6.75(2H, d, J=8 Hz), 6.80(1H, s), 7.24(1H, s), 7.34(2H, d, J=8 Hz), 8.37(2H, d, J=8 Hz), 9.30(2H, d, J=8 Hz).

Solubility(in distilled water at 25° C.): 30% or higher.

EXAMPLE 51

Sodium 7$\beta$-[D-2-(4-carboxymethoxyphenyl)-2-(6,7-dihydroxy-4-oxo-4H-1-benzopyran-3-carboxamido)-acetamido]-7$\alpha$-methoxy-3-(4-carbamoylpyridinium)-methyl-3-cephem-4-carboxylate A mixture of the compound (2.88 g) obtained in Example 34, isonicotinamide (14.4 mg), sodium iodide (57.6 g) and water (50 ml) was stirred at 73° C. for 2 hours and 15 minutes. The liquid reaction mixture was added to ethanol (400 ml), and the resultant precipitate was collected by filtation and washed with ethanol, acetone and ethyl ether. It was then dissolved in water (19 ml), to which ethanol (35 ml) was added. The resultant precipitate was collected by filtration. It was again dissolved in water (41 ml), followed by an addition of 0.5N—HCl (5.2 ml). The resultant precipitate was collected by filtration, and then washed successively with water, a liquid mixture of acetone and ethyl ether, and acetone. The thus-obtained solid matter was dissolved in dimethylformamide in an amount 10 times the weight of the solid matter. The resultant solution was added dropwise to acetone in an amount 2.8 times the weight of the dimethylformamide and the resultant precipitate was collected by filtration. These procedures were repeated twice, and the thus-obtained solid matter was taken up in an aqueous solution of sodium acetate (42 mg/3.3 ml). Ethanol (5.5 ml) was added dropwide to the solution and the resultant mixture ice-cooled. The resultant precipitate was washed with ethanol and ethyl ether to obtain the desired product (280 mg).

Infrared absorption spectrum[cm$^{-1}$, Nujol(trade mark)]: 1770,, 1720, 1690, 1660, 1630, 1610.

NMR spectrum($\delta$, DMSO-d$_6$-D$_2$O): 3.43(3H, s), 4.22(2H, s), 4.99(1H, s), 5.0–5.7(2H), 5.66(1H, s), 6.78(2H, d, J=8 Hz), 6.90(1H, s), 7.35(1H, s), 7.36(2H, d, J=8 Hz), 8.38(2H, d, J=7 Hz), 8.81(1H, s), 9.32(2H, d, J=7 Hz).

Solubility(in distilled water at 25° C.): 30% or higher.

EXAMPLE 52

7$\beta$-[D-2-(4-Carboxymethoxyphenyl)-2-(6,7-dihydroxy-1-ethyl-1,4-dihydro-4-oxoquinoline-3-carboxamido)-acetamido]-3-(4-carbamoylpyridinium)methyl-3-cephem-4-carboxylate A mixture of the compound (2.1 g) obtained in Example 35, isonicotinamide (10.5 g), sodium iodide (42 g) and water (35.7 ml) was stirred at 70° C. for 2 hours. Ethanol (300 ml) was added to the liquid reaction mixture and the resultant precipitate was collected by filtration, followed by washing with ethanol and ethyl ether. It was dissolved in water (60 ml), to which a dilute hydrochloric acid was added to make the solution acidic. The resultant precipitate was collected by filtration and washed first with water and then with acetone. The thus-obtained solid matter was taken up in dimethylformamide (8 ml), followed by an addition of acetone (16 ml). The resultant precipitate was collected by filtration and then washed with ethyl ether. These procedures were repeated again to obtain the desired product (857 mg).

Infrared absorption spectrum[cm$^{-1}$, Nujol(trade mark)]: 1765, 1680, 1650, 1630, 1600.

NMR spectrum($\delta$, DMSO-d$_6$): 1.36(3H, t, J=7 Hz), 4.60(2H, s), 4.93(1H, d, J=5 Hz), 5.13(1H, d, J=14 Hz), 5.50–5.90(3H, m), 6.81(2H, d, J=8 Hz), 7.13(1H, s), 7.32(2H, d, J=8 Hz), 7.62(1H, s), 8.42(2H, d, J=8 Hz), 8.58(1H, s), 9.53(2H, d, J=8 Hz)

EXAMPLE 53

Sodium 7$\beta$-[D-2-(4-carboxymethoxyphenyl)-2-(6,7-dihydroxy-1-ethyl-1,4-dihydro-4-oxoquinoline-3-carboxamido)acetamido]-3-(4-carbamoylpyridinium)-methyl-3-cephem-4-carboxylate The compound (845 mg) obtained in Example 52 sodium acetate (110 mg) and water (8 ml) were stirred to dissolve the same, followed by a dropwise addition of ethanol (100 ml). The resultant precipitate was collected by filtration, washed with ethanol and ethyl ether, and then dried to obtain the desired product (748 mg).

Infrared absorption spectrum[cm$^{-1}$, Nujol(trade mark)]: 1760, 1680, 1630, 1600.

NMR spectrum($\delta$, DMSO-d$_6$-D$_2$O): 1.38(3H, t, J=7 Hz), 3.24(1H, d, J=22 Hz), 4.22(2H, s), 4.95(1H, d, J=5 Hz), 5.18(1H, d, J=13 Hz), 5.45–5.80(3H, m), 6.82(2H, d, J=8 Hz), 7.12(1H, s), 7.32(2H, d, J=8 Hz), 7.63(1H, s), 8.34(2H, d, J=8 Hz), 8.58(1H, s), 9.30(1H, d, J=8 Hz).

Solubility(in distilled water at 25° C.): 30% or higher.

EXAMPLE 54

7$\beta$-[D-2-(4-Carboxymethoxyphenyl)-2-(6,7-dihydroxy-2-methyl-4-oxo-4H-1-benzopyran-3-carboxamido)-acetamido]-3-(4-carboxypyridinium)methyl-3-cephem-4-carboxylate Sodium oxide (40 g) and isonicotinic acid (5.7 g) were suspended in water (10 ml). The pH of the resulting suspension was adjusted to 6.5 with an aqueous 4N-sodium hydroxide solution. The mixture was heated to 70° C., followed by an addition of the compound (1.14 g) obtained in Example 29. The resulting mixture was stirred at the same temperature for 1 hour and 45 minutes. Ethanol (50 ml) was added to the liquid reaction mmixture to form a precipitate, which was then washed with ethanol and ethyl ether. The thus-washed precipitate was suspended in water (15 ml), to which an aqueous 1N-sodium acetate solution was thereafter added to dissolve the precipitate. The resulting solution was neutralized, under ice-cooled conditions, with 1N—HCl to form a precipitate. The precipitate was collected by filtration and then washed with water. It was dissolved in dimethylformamide (3 ml) and the resulting solution was added dropwise to acetone (14 ml). The resulting precipitate was collected by filtration and washed with a mixed solvent of dimethylformamide and acetone, acetone and ethyl ether to obtain the desired product (170 mg).

Infrared absorption spectrum[cm$^{-1}$, Nujol(trade mark)]: 1770, 1625.

NMR spectrum($\delta$, DMSO-d$_6$-D$_2$O): 2.60(3H, s), 4.62(2H, s), 5.03(1H, d, J=5 Hz), 5.1–5.8(2H), 5.62(1H, s), 5.75(1H, d, J=5 Hz), 6.87(2H, d, J=8.5 Hz), 6.92(1H, s), 7.33(1H, s), 7.37(2H, d, J=8.5 Hz), 8.32(2H, d, J=7 Hz), 9.10(2H, d, J=7 Hz).

EXAMPLE 55

Disodium 7$\beta$-[D-2-(4-carboxymethoxyphenyl)-2-(6,7-dihydroxy-2-methyl-4-oxo-4H-1-benzopyran-3-carboxamido)acetamido]-3-(4-carboxypyridinium)-methyl-3-cephem-4-carboxylate Chilled water (0.5 ml) was added to the compound (100 mg) obtained in Example 54 and sodium carbonate (15.3 mg) to dissolve the compound and carbonate. Ethanol (5 ml) was added to the resulting solution to form a precipitate, which was then collected by filtration. The precipitate was washed with ethanol and ethyl ether to obtain the desired product (106 mg).

Infrared absorption spectrum[cm$^{-1}$, Nujol(trade mark)]: 1760, 1605.

NMR spectrum($\delta$, DMSO-d$_6$-D$_2$O): 2.60(3H, s), 4.11(2H, s), 4.91(1H, d, J=5 Hz), 4.9–5.7(2H), 5.56(1H, s), 5.62(1H, d, J=5 Hz), 6.48(1H, s), 6.75(2H, d, J=8.5 Hz), 7.12(1H, s), 7.29(2H, d, J=8.5 Hz), 8.18(2H, d, J=7 Hz), 9.18(2H, d, J=7 Hz).

EXAMPLE 56

7$\beta$-[D-2-(4-Carboxymethoxyphenyl)-2-(6,7-diacetoxy-2-methyl-4-oxo-4H-1-benzopyran-3-carboxamido)acetamido]-3-(4-carbamoylpyridinium)methyl-3-cephem-4-carboxylate (a) 7$\beta$-Amino-3-(4-carbamoylpyridinium)methyl-3-cephem-4-carboxylate:

7$\beta$-Amino-3-acetoxymethyl-3-cephem-4-carboxylic acid (10.8 g) was added to a phosphate buffer (80 ml) which contained sodium hydrogencarbonate (3.2 g). Thereafter, isonicotinamide (21.2 g) and sodium iodide (40 g) were respectively added. The resulting mixture was stirred at 60° C. for 2 and a half hours. After allowing the liquid reaction mixture to cool down, the reaction mixture was added dropwise and with stirring to acetone (1 liter). The resulting mixture was allowed to stand to form an oily precipitate, which was thereafter collected and then taken up in water (80 ml). Methanol (30 ml) was added to the resulting aqueous solution and the insoluble matter was removed by filtration. Methanol was then evaporated under reduced pressure. The residue was charged on a column (diameter: 5.5 cm; length: 50 cm) packed with "DIA-ION HP 20" (trade mark). The column was eluted with water. Fractions, which contained the desired product, were collected and lyophilized to obtain the desired product (3.0 g).

Infrared absorption spectrum[cm$^{-1}$, Nujol(trade mark)]: 1740, 1650.

NMR spectrum($\delta$, DMSO-d$_6$): 3.01(1H, d, J=18 Hz), 3.46(1H, d, J=18 Hz), 4.62(1H, d, J=5 Hz), 4.88(1H, d, J=5 Hz), 5.16(1H, d, J=14 Hz), 5.65(1H, d, J=14 Hz), 8.38(2H, d, J=8 Hz), 9.44(2H, d, J=8 Hz).

(b) 7$\beta$-[D-2-[4-(p-Methoxybenzyloxycarbonylmethoxy)phenyl]-2-(p-methoxybenzyloxycarbonylamino)acetamido]-3-(4-carbamoylpyridinium)-methyl-3-cephem-4-carboxylate:

D-2-[4-(p-Methoxybenzyloxycarbonylmethoxy)-phenyl]-2-(p-methoxybenzyloxycarbonylamino)acetic acid (2 g) was dissolved in dimethylformamide (15 ml), followed by successive addition of N-methylmorpholine (400 $\mu$l) and ethyl chloroformate (420 $\mu$l) with cooling in an ice.salt bath. The resulting mixture was stirred for 30 minutes.

Separately, the compound (660 mg) obtained in the above procedure (a) was taken up in a liquid mixture of water (3 ml) and dimethylformamide (8 ml). To the resulting mixture, was added with ice-cooling the above-prepared solution. The resulting mixture was stirred for 1 hour. The liquid reaction mixture was added to a liquid mixture of methanol (80 ml) and isopropanol (200 ml) to form a precipitate, which was then collected by filtration and washed with isopropanol an isopropyl ether. The thus-washed precipitate was dissolved in a liquid mixture of water (150 ml) and tetrahydrofuran (150 ml) followed by evaporation of tetrahydrofuran under reduced pressure. The resulting precipitate was collected by filtrate to obtain the desired product (75 mg).

Infrared absorption spectrum[cm$^{-1}$, Nujol(trade mark)]: 1710–1750, 1620–1660.

NMR spectrum($\delta$, DMSO-d$_6$): 3.71(3H, s), 3.72(3H, s), 4.73(2H, s), 4.94(2H, s), 5.05(2H, s), 5.30(1H, d, J=10 Hz), 5.50–5.70(1H, m), 6.75–7.00(6H, m), 7.15–7.40(6H, m), 8.38(2H, d, J=8 Hz), 9.57(2H, d, J=8 Hz).

(c) Trifluoroacetic acid salt of 7$\beta$-[D-2-amino-2-(4-carboxymethoxyphenyl)-acetamido]-3-(4-carbamoylpyridinium)methyl-3-cephem-4-carboxylic acid:

The compound (70 mg) obtained in the above procedure (b), trifluoroacetic acid (0.4 ml) and anisole (0.8 ml) were stirred for 1 hour with ice-cooling. Isopropyl ether (50 ml) was then added to the resulting liquid reaction mixture to form a precipitate. The precipitate was collected by filtration to give the desired product (59 mg).

Infrared absorption spectrum[cm$^{-1}$, Nujol(trade mark)]: 1760, 1700, 1600–1650.

NMR spectrum($\delta$, DMSO-d$_6$): 4.62(2H, s), 4.92(1H, s), 5.03(1H, d, J=5 Hz), 5.32(1H, d, J=14 Hz), 5.63(1H, d, J=14 Hz), 5.7–5.9(1H, m), 6.90(2H, d, J=8 Hz), 7.36(2H, d, J=8 Hz), 8.42(2H, d, J=8 Hz), 9.22(2H, d, J=8 Hz).

(d) 7$\beta$-[D-2-(4-Carboxymethoxyphenyl)-2-(6,7-diacetoxy-2-methyl-4-oxo-4-H-1-benzopyran-3-carboxamido)acetamido]-3-(4-carbamoylpyridinium)methyl-3-cephem-4-carboxylate:

The compound (71 mg) obtained in the above procedure (c) was suspended in acetonitrile (5 ml), followed by an addition of N,O-bis(trimethylsilyl)acetamide (107 $\mu$l). The resulting mixture was stirred, to which 6,7-diacetoxy-2-methyl-4-oxo-4H-1-benzopyran-3-carbonyl chloride (35 mg) was added. The thus-obtained mixture was stirred for 1 hour. Methanol (2 ml) and isopropyl ether (50 ml) were successively added to the liquid reaction mixture to form a precipitate. The precipitate was collected by filtration to obtain the desired product (70 mg).

Infrared absorption spectrum[cm$^{-1}$, Nujol(trade mark)]: 1750–1780, 1610–1660.

NMR spectrum($\delta$, DMSO-d$_6$): 1.30(3H, s), 1.32(3H, s), 1.57(3H, s), 4.60(2H, s), 5.05(1H, d, J=5 Hz), 5.4–5.9(3H, m), 6.82(2H, d, J=8 Hz), 7.36(2H, d, J=8 Hz), 7.70(1H, s), 7.90(1H, s), 8.48(2H, d, J=8 Hz), 9.16(2H, d, J=8 Hz).

EXAMPLE 57

7$\beta$-[D-2-(4-Carboxymethoxyphenyl)-2-(6,7-dihydroxy-2-methyl-4-oxo-4H-1-benzopyran-3-carboxamido)acetamido]-3-(4-carbamoylpyridinium)methyl-3-cephem-4-carboxylate To the compound (50 mg) obtained in Example 56 and sodium hydrogencarbonate (15 mg) were added water (650 $\mu$l) and ethanol (500 $\mu$l). The resulting mixture was agitated fro 1 hour. Isopropanol (15 ml) was added to the liquid reaction mixture to form a precipitate, which was then collected by filtration. It was dissolved in water (650 $\mu$l) and the insoluble matter was removed by filtration. 1N—HCl (32 $\mu$l) was then added to the filtrate and the resulting precipitate was collected by filtration. The precipitate was washed successively with water, ethyl ether, ethanol and ethyl ether to obtain the desired product (17 mg).

Infrared absorption spectrum[cm$^{-1}$, Nujol(trade mark)]: 1760, 1670, 1620.

NMR spectrum($\delta$, DMSO-d$_6$): 2.58(3H, s), 3.08(1H, d, J=18 Hz), 3.45(1H, d, J=18 Hz), 4.58(2H, s), 4.92(1H, d, J=5 Hz), 5.17(1H, d, J=14 Hz), 5.5–5.8(3H), 6.80(2H, d, J=8.5 Hz), 6.87(1H, s), 7.28(1H, s), 7.34(2H, d, J=8.5 Hz), 8.20(1H, s), 8.42(2H, d, J=7 Hz), 8.66(1H, s), 9.28(1H, d, J=8 Hz), 9.45(2H, d, J=7 Hz), 10.04(1H, d, J=7 Hz).

Antibacterial activities and excretion rates into urine of certain compounds according to this invention will next be described.

(1) Antibacterial activities (MIC):

| | MIC ($\mu$g/ml) | | | | | | |
|---|---|---|---|---|---|---|---|
| | Test bacteria | | | | | | |
| Test compound | Staph. aureus 209-P | Escher. coli NIHJ | Kleb. pneumoniae EK-6 | Proteus morganii EP-14 | Pseud. aeruginosa EP-01 | Ser. marcescens ES-75 | Proteus vulgaris E-18* |
| Example 1 | 25 | 0.2 | ≦0.05 | 6.25 | ≦0.05 | 0.2 | — |
| Example 4 | 6.25 | 0.8 | ≦0.05 | 0.8 | ≦0.05 | 0.2 | — |
| Example 6 | 3.13 | 0.8 | ≦0.05 | 1.56 | ≦0.05 | 0.2 | — |
| Example 8 | 50 | 0.8 | ≦0.05 | 1.56 | 0.1 | 0.2 | — |
| Example 9 | 25 | 0.4 | ≦0.05 | 1.56 | ≦0.05 | 0.2 | — |
| Example 10 | 12.5 | 0.4 | ≦0.05 | 3.13 | ≦0.05 | 0.1 | — |
| Example 11 | 12.5 | 0.2 | ≦0.05 | 0.4 | 0.1 | ≦0.05 | — |
| Example 12 | 50 | 0.4 | ≦0.05 | 1.56 | 0.1 | ≦0.05 | — |
| Example 14 | 25 | 0.4 | ≦0.05 | 3.13 | 0.1 | 0.2 | — |
| Example 15 | 100 | 0.2 | ≦0.05 | 3.13 | 0.2 | 0.1 | — |
| Example 16 | 100 | 0.8 | 0.2 | 6.25 | 0.8 | 0.8 | — |
| Example 17 | 50 | 0.8 | ≦0.05 | 12.5 | 0.8 | 1.56 | — |
| Example 20 | 100 | 0.8 | 0.1 | 6.25 | 0.8 | 0.8 | — |
| Example 21 | 100 | 0.4 | ≦0.05 | 3.13 | 0.2 | 0.1 | 0.4 |
| Example 22 | 100 | 0.2 | ≦0.05 | 3.13 | 0.2 | 0.1 | — |
| Example 23 | 100 | 0.4 | ≦0.05 | 6.25 | 0.8 | 0.8 | — |
| Example 24 | 100 | 0.8 | ≦0.05 | 12.5 | 0.8 | 0.8 | 3.13 |
| Example 25 | 100 | 0.4 | ≦0.05 | 3.13 | 0.4 | 0.1 | 0.4 |
| Example 27 | 100 | 0.4 | ≦0.05 | 6.25 | 0.8 | 0.8 | — |
| Example 28 | 100 | 0.8 | ≦0.05 | 6.25 | 0.8 | 0.8 | 3.13 |

-continued

| Test compound | Staph. aureus 209-P | Escher. coli NIHJ | Kleb. pneumoniae EK-6 | Proteus morganii EP-14 | Pseud. aeruginosa EP-01 | Ser. marcescens ES-75 | Proteus vulgaris E-18* |
|---|---|---|---|---|---|---|---|
| Example 29 | 50 | 0.4 | ≦0.05 | 12.5 | 0.2 | 0.4 | — |
| Example 30 | 100 | 0.8 | ≦0.05 | 6.25 | 0.4 | 0.2 | 0.8 |
| Example 31 | 50 | 0.8 | ≦0.05 | 6.25 | 0.4 | 0.4 | 1.56 |
| Example 33 | 50 | 0.8 | ≦0.05 | 12.5 | 0.2 | 0.8 | 1.56 |
| Example 35 | 50 | 0.8 | ≦0.05 | 12.5 | 0.2 | 1.56 | — |
| Example 36 | 25 | 0.8 | ≦0.05 | 12.5 | 0.1 | 0.8 | — |
| Example 40 | 100 | 0.8 | 0.1 | 12.5 | 0.2 | 0.6 | — |
| Example 41 | 50 | 0.4 | ≦0.05 | 6.25 | 0.2 | 0.4 | — |
| Example 42 | 100 | 0.2 | ≦0.05 | 3.13 | 0.2 | 0.2 | — |
| Example 43 | 100 | 0.8 | ≦0.05 | 12.5 | 0.1 | 0.2 | — |
| Example 44 | 25 | 0.8 | ≦0.05 | 25 | 0.1 | 0.8 | — |
| Example 45 | 25 | 0.8 | ≦0.05 | 6.25 | 0.1 | 0.8 | — |
| Example 46 | 50 | 0.4 | ≦0.05 | 25 | 0.4 | 0.8 | — |
| Example 48 | 100 | 0.2 | ≦0.05 | 6.25 | 0.2 | 0.1 | 1.56 |
| Example 50 | 100 | 1.56 | 0.1 | 12.5 | 0.4 | 0.8 | 3.13 |
| Example 51 | 50 | 1.56 | ≦0.05 | 25 | 0.4 | 0.8 | 3.13 |
| Example 53 | 50 | 0.4 | ≦0.05 | 6.25 | 0.2 | 0.8 | — |
| Example 55 | 100 | 0.4 | ≦0.05 | 6.25 | ≦0.05 | 0.4 | — |
| Example 56 | 25 | 0.8 | ≦0.05 | 6.25 | 0.2 | 0.8 | — |
| Example 57 | 50 | 0.4 | ≦0.05 | 6.25 | 0.2 | 0.4 | — |

*β-Lactamase producing bacteria.

(2) Urinary Excretion rates:

ICR male mice (body weight: 20-30 g) were used. Each compound was dissolved in an M/15 phosphate buffer (pH 7.0) and administered in an amount of 20 mg/kg by the subcutaneous route. Urine was collected up to 6 hours after the administration. The concentration of the compound was determined by the bioassey technique (the agar-well method) using *Pseudomonas aeruginosa* as a test microorganism. On the basis of the thus-determined concentration, its excreted amount was obtained. The urinary excretion rate was then calculated from the excreted amount based on the amount administered.

| Compound | Urinary excretion rate (%) in mice |
|---|---|
| Example 8 | 20 |
| Example 15 | 32 |
| Example 20 | 16 |
| Example 25 | 20 |
| Example 27 | 30 |
| Example 28 | 24 |
| Example 40 | 39 |
| Example 41 | 74 |
| Example 42 | 46 |
| Example 43 | 25 |
| Example 44 | 40 |
| Example 45 | 38 |
| Example 46 | 62 |
| Example 48 | 45 |
| Example 49 | 35 |
| Example 51 | 16 |
| Example 53 | 13 |

What is claimed is:

1. A compound of the formula

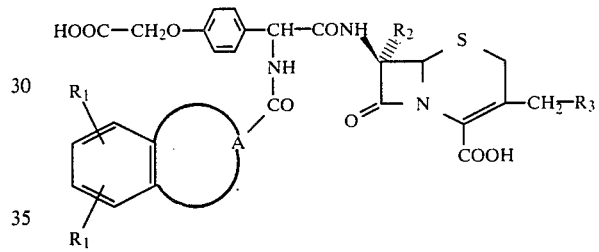

wherein $R_1$ represents hydroxy, $C_1$-$C_4$ alkanoyloxy or $C_1$-$C_4$ alkoxycarbonyloxy, $R_2$ represents hydrogen or methoxy, $R_3$ repesents (1) $C_1$-$C_4$ alkanoyloxy or (2) pyridinium which is unsubstituted or substituted by $C_1$-$C_4$ alkyl, carboxyalkyl, sulfoalkyl, carboxyl, sulfo, amino, N,N-dialkylaminoalkyl, carbamoyl, alkylcarbamoyl, alkoxycarbonyl, cyano, hydroxycarbamoyl, N-hydroxycarbamoylalkyl, carbamoylalkyl, dialkylcarbamoyl, N-hydroxy-N-alkylcarbamoyl, hydroxy, hydroxyalkyl and alkoxycarbonylalkyl with the proviso that, when $R_3$ denotes the substituted or unsubstituted pyridinium, $R_3$ forms an intramolecular salt with the carboxy at the 4-position of the cephem nucleus, And A is a group of the formula:

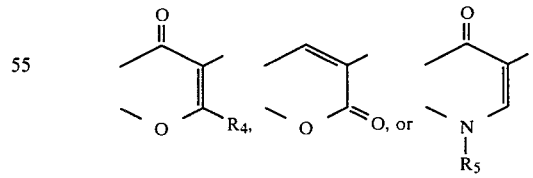

in which $R_4$ and $R_5$ are individually hydrogen or $C_1$-$C_4$ alkyl, or a pharmaceutically acceptable salt thereof, wherein undefined alkyl and alk are lower alkyl and lower alk.

2. A compound according to claim 1, wherein $R_3$ represents $C_1$-$C_4$ alkanoyloxy or pyridinium, the said pyridinium being optionally substituted by one or more substituents selected from $C_1$-$C_4$ alkyl, carboxyalkyl, sulfoalkyl, carboxyl, sulfo, amino, N,N-dialkylaminoalkyl, carbamoyl, alkylcarbamoyl, alkoxycarbonyl, cyano, hydroxycarbamoyl, N-hydroxycarbamoylalkyl, carbamoylalkyl, dialkylcarbamoyl, N-hydroxy-N-alkylcarbamoyl, hydroxy, hydroxyalkyl and alkoxycarbonylalkyl, or a pharmaceutically acceptable salt thereof.

3. A compound according to claim 1, wherein $R_3$ is acetoxy pyridinium, 4-carbamoylpyridinium, 4-(2-sulfoethyl)-pyridinium, 3-carbamoylpyridinium or 4-carboxypyridinium, or a pharmaceutically acceptable salt thereof.

4. A compound according to claim 1, wherein A is a group of the following formula:

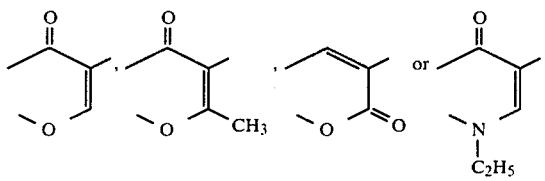

or a pharmaceutically acceptable salt thereof.

5. A compound according to claim 1, wherein $R_1$ is hydroxy, acetoxy or ethoxycarbonyloxy, or a pharmaceutically acceptable salt thereof.

6. A compound according to claim 1, which is 7β-[D-2-(4-carboxymethoxyphenyl)-2-(6,7-dihydroxy-2-methyl-4-oxo-4H-1-benzopyran-3-carboxamido)-acetamido]-3-(4-carbamoylpyridinium)methyl-3-cephem-4-carboxylate or a pharmaceutically acceptable salt thereof.

7. A compound according to claim 1, which is 7β-[D-2-(4-carboxymethoxyphenyl)-2-(6,7-dihydroxy-4-oxo-4H-1-benzopyran-3-carboxamido)acetamido]-3-[4-(2-sulfoethyl)pyridinium]methyl-3-cephem-4-carboxylate or a pharmaceutically acceptable salt thereof.

8. A compound according to claim 1 which is 7β-[D-2-(carboxymethoxyphenyl)-2-(6,7-dihydroxy-2-methyl-4-oxo-4H-1-benzopyran-3-carboxamido)acetamido]-3-[4-(2-sulfoethyl)pyridinium]methyl-3-cephem-4-carboxylate or a pharmaceutically acceptable salt thereof.

9. A compound according to claim 1, which is 7β-[D-2-(4-carboxymethoxyphenyl)-2-(6,7-dihydroxy-2-methyl-4-oxo-4H-1-benzopyran-3-carboxamido)acetamido]-7α-methoxy-3-pyridiniummethyl-3-cephem-4-carboxylate or a pharmaceutically acceptable salt thereof.

10. A compound according to claim 1, which is 7β-[D-2-(4-carboxymethoxyphenyl)-2-(6,7-dihydroxy-2-methyl-4-oxo-4H-1-benzopyran-3-carboxamido)acetamido]-7α-methoxy-3-(4-carbamoylpyridinium)methyl-3-carboxylate or a pharmaceutically acceptable salt thereof.

11. A compound according to claim 1, which is 7β-[D-2-(4-carboxymethoxyphenyl)-2-(6,7-dihydroxy-2-methyl-4-oxo-4H-1-benzopyran-3-carboxamido)acetamido]-3-pyridiniummethyl-3-cephem-4-carboxylate or a pharmaceutically acceptable salt thereof.

12. A compound according to claim 1, which is 7β-[D-2-(4-carboxymethoxyphenyl)-2-(6,7-dihydroxy-2-methyl-4-oxo-4H-1-benzopyran-3-carboxamido)acetamido]-3-(4-carboxypyridinium)methyl-3-cephem-4-carboxylate or a pharmaceutically acceptable salt thereof.

13. A compound according to claim 1, which is 7β-[D-2-(4-carboxymethoxyphenyl)-2-(6,7-dihydroxy-2-methyl-4-oxo-4H-1-benzopyran-3-carboxamido)acetamido]-3-acetoxymethyl-3-cephem-4-carboxylic acid or a pharmaceutically acceptable salt thereof.

14. An antibacterial composition which comprises an antibacterially effective amount of a compound according to claim 1 or a pharmaceutically acceptable salt thereof and a pharmaceutically acceptable carrier therefor.

* * * * *